United States Patent
Damodaran

(10) Patent No.: US 11,634,462 B2
(45) Date of Patent: Apr. 25, 2023

(54) METHODS OF PROCESSING β-LACTOGLOBULIN-CONTAINING COMPOSITIONS WITH THERMOLYSIN AND TRANSGLUTAMINASE

(71) Applicant: WISCONSIN ALUMNI RESEARCH FOUNDATION, Madison, WI (US)

(72) Inventor: Srinivasan Damodaran, Middleton, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 775 days.

(21) Appl. No.: 16/416,744

(22) Filed: May 20, 2019

(65) Prior Publication Data
US 2019/0352352 A1 Nov. 21, 2019

Related U.S. Application Data

(60) Provisional application No. 62/674,186, filed on May 21, 2018.

(51) Int. Cl.
*C07K 14/47* (2006.01)
*A23J 3/08* (2006.01)

(52) U.S. Cl.
CPC .............. *C07K 14/47* (2013.01); *A23J 3/08* (2013.01)

(58) Field of Classification Search
None
See application file for complete search history.

(56) References Cited

PUBLICATIONS

Lohmanderetal, The Release of Crosslinked Peptides From Type II Collagen Into Human Synovial Fluid Is Increased Soon After Joint Injury and in Osteoarthritis. Arthritis & Rheumatism vol. 48, No. 11, Nov. 2003, pp. 3130-3139.*
Babiker et al, E-ect of transglutaminase treatment on the functional properties of native and chymotrypsin-digested soy protein. Food Chemistry 70 (2000) 139-145.*
Chen et al, 2009 Preparing protein foaming agent used for food processing, by hydrolyzing protein e.g. lactalbumin with Alcalase, ultrafiltering to obtain peptide fragments, and freeze drying transglutaminase cross-linked fragments to form agent. English translation of CN 101361532 abstract.*
ExPASy—PeptideCutter albumin-ABF57425_cutting by thermolysin. Performed Feb. 24, 2022.*
Otte eta l, Fractionation and identification of ACE-inhibitory peptides from a-lactalbumin and b-casein produced by thermolysin-catalysed hydrolysis. International Dairy Journal 17 (2007) 1460-1472.*
O'Sullivan et al, Physicochemical properties and residual antigenicity of transglutaminase cross-linked sodium caseinate hydrolysates. International Dairy Journal 23 (2012) 18-23.*
Wroblewska etal,Influence of Alcalase and Transglutaminase on Immunoreactivity of Cow Milk Whey Proteins. Czech J. Food Sci. (2008) vol. 26, No. 1: 15-23.*
Hsieh et al., Isolation of prolyl endopeptidase inhibitory peptides from a sodium caseinate hydrolysate. Food Funct., 2016, 7, 565.*
Adjonu R, Doran G, Torley P, Agboola S. Screening of whey protein isolate hydrolysates for their dual functionality: influence of heat pre-treatment and enzyme specificity. *Food Chemistry*. Feb. 15, 2013. 136(3-4):1435-43.
Agyare, K.K., & Damodaran, S. pH-stability and thermal properties of microbial transglutaminase-treated whey protein isolate. *Journal of Agricultural and Food Chemistry*. 2010. 58, 1946-1953.
Ahn, K. M., Han, Y. S., Nam, S. Y., Park, H. Y., Shin, M. Y., & Lee, S. I. Prevalence of soy protein hypersensitivity in cow's milk protein-sensitive children in Korea. *Journal of Korean Medical Science*. 2003. 18, 473-478.
Baudon, J.J., Mougenot, J.F., & Didry, J.R. Lymphoblastic stimulation test with food proteins in digestive intolerance to cow's milk and in infant diarrheas. *Journal of Pediatric Gastroenterology and Nutrition*. 1987. 6, 244-251.
Bindels, J.G., & Boerma, J.A. Hydrolysed cow's milk formulae. *Pediatric Allergy and Immunology*. 1994. 5, 189-190.
Binks, B.P. Particles as surfactants—similarities and differences. *Current Opinion in Colloid and Interface Science*. 2002. 7, 21-41.
Binks, B.P., BOA, A.N., Kibble, M.A., Mackenzie, G., & Rocher, A. Sporopollenin capsules at fluid interfaces: particle-stabilized emulsions and liquid marbles. *Soft Matter*. 2011. 4017-4024.
Breiteneder H, Chapman MD. Allergen Nomenclature. "Allergens and Allergen Immunotherapy: Subcutaneous, sublingual and oral." 5th Edition. Editors Richard F. Lockey, Dennis K. Ledford, CRC Press, Taylor and Francis Group, Boca Raton, Florida, USA. 2014. pp. 37-49.
Buchert, J., Selinheimo, E., Kruus, K., Mattinen, M.L., Lantto, R., Autio, K., & Rastall, R. Using crosslinking enzymes to improve textural and other properties of food. "Novel enzyme technology for food applications." Editor Rastall, R. Woodhead Publishing, Cambridege, UK. 2008. pp. 101-139.

(Continued)

*Primary Examiner* — Tekchand Saidha
(74) *Attorney, Agent, or Firm* — Daniel A. Blasiole; DeWitt LLP

(57) ABSTRACT

Methods of processing protein, methods of generating products with the processed protein, and products comprising and/or made with the processed protein. The methods of processing protein include hydrolyzing the protein with a proteolytic agent such as thermolysin to generate hydrolyzed peptides and, optionally, crosslinking the hydrolyzed peptides with a transglutaminase to generate crosslinked peptides. The methods reduce the allergenicity of allergenicity proteins such as β-lactoglobulin and casein. The methods of generating products with the processed protein include methods of making foams, emulsions, and/or food products with the processed protein. The products comprising and/or made with the processed protein accordingly include foams, emulsions, and food products. The foams, emulsions, and food products have decreased allergenicity compared to corresponding products made with non-processed proteins.

20 Claims, 25 Drawing Sheets
Specification includes a Sequence Listing.

(56) References Cited

PUBLICATIONS

Burks, A.W., Casteel, H.B., Fiedorek, S.C., Williams, L.W., & Pumphrey, C.L. Prospective oral food challenge study of two soybean isolates in patients with possible milk or soy protein enterocolitis. *Pediatric Allergy and Immunology*. 1994. 5, 40-45.

Businco, L., Dreborg, S., Einarsson, R., Giampietro, P.G., Host, A., Keller, K.M., Strobel, S, Wahn, U., Bjorksten, B., & Kjellman, M.N. Hydrolysed cow's milk formulae. Allergenicity and use in treatment and prevention: an ESPACI position paper. *Pediatric Allergy and Immunology*. 1993. 4, 101-111.

Chapman MD, Pomés A, Breiteneder H, Ferreira F. Nomenclature and structural biology of allergens. *The Journal of Allergy and Clinical Immunology*. 2007. 119:414-20.

Chapman MD. Allergen nomenclature. "Allergens and Allergen Immunotherapy" 3rd Edition. Editors RF Lockey, SC Bukantz & J Bousquet. Marcel Decker. 2004. pp. 51-64.

Chapman Md. Allergen nomenclature. "Allergens and Allergen Immunotherapy" 4th. Edition. Editors Richard F. Lockey, Dennis K. Ledford. Informa Healthcare, New York. 2008. pp. 47-58.

Chen A, Tanidjaja I, Damodaran S. Nanostructure and functionality of enzymatically repolymerized whey protein hydrolysate. *Food Chemistry*. Aug. 1, 2018. 256:405-412.

Damodaran S, Li Y. A two-step enzymatic modification method to reduce immuno-reactivity of milk proteins. *Food Chemistry*. Dec. 15, 2017. 237:724-732.

Damodaran, S. Protein Stabilization of Emulsions and Foams. *Journal of Food Science*. 2005. 70, 54-65.

Damodaran, S., & Anand, K. Sulfhydryl-disulfide interchange-induced interparticle polymerization in whey protein-stabilized emulsions and its relation to emulsion stability. *Journal of Agricultural and Food Chemistry*. 1997. 45, 3813-3820.

Dejong, G. A. H., & Koppelman, S. J. Transglutaminase catalyzed reactions: impact on food applications. *Journal of Food Science and Technology*. 2002. 67, 2798-2806.

Dickinson, E. Food emulsions and foams: stabilization by particles. *Current Opinion in Colloid and Interface Science*. 2010. 15, 40-49.

Docena, G.H., Fernandez, R., Chirdo, F.G., & Fossati, C.A. Identification of casein as the major allergenic and antigenic protein of cow's milk. *Allergy*. 1996. 51, 412-416.

Dupont, D., Mandalari, G., Molle, D., Jardin, J., Léonil, J., Faulks, R. M., Wickham, M. S. J., Mills, E. N. C., & Mackie, A. R. Comparative resistance of food proteins to adult and infant in vitro digestion models. *Molecular Nutrition and Food Research*. 2010. 54, 767-780.

Exl, B. M., Fritsché, R. Cow's milk protein allergy and possible means for its prevention. *Nutrition*. 2001. 17, 642-651.

Fu, T. J., Abbott, U. R., & Hatzos, C. Digestibility of food allergens and nonallergenic proteins in simulated gastric fluid and simulated intestinal fluid A comparative study. *Journal of Agricultural and Food Chemistry*. 2002. 50, 7154-7160.

Halken, S., Hansen, K.S., Jacobsen, H.P., Estmann, A., Faelling, A.E., Hansen, L.G., Kier, S.R., Lassen, K., Lintrup, M., Mortensen, S., Ibsen, K.K., Osterballe, O., & Host, A. Comparison of a partially hydrolyzed infant formula with two extensively hydrolyzed formulas for allergy prevention: A prospective, randomized study. *Pediatric Allergy and Immunology*. 2000. 11, 149-161.

Han, X-Q., & Damodaran, S. Thermodynamic compatibility of substrate proteins affects their crosslinking by transglutaminase. *Journal of Agricultural and Food Chemistry*. 1996. 44, 1211-1217.

Hunter, T.N., Pugh, R.J., Franks, G.V. & Jemeson, G.J. The role of particles in stabilizing foams and emulsions. *Advances in Colloid and Interface Science*. 2008. 137, 57-81.

King TP, Hoffman D, Lowenstein H, Marsh DG, Platt-Mills TA, Thomas WR. Allergen Nomenclature. *Bulletin of the World Health Organization*. 1994, 72:797-800.

King TP, Hoffman D, Lowenstein H, Marsh DG, Platts-Mills TA, Thomas W. Allergen nomenclature. *WHO/IUIS Allergen Nomenclature Subcommittee. International Archives of Allergy and Immunology*. 1994. 105:224-33.

King TP, Hoffman D, Lowenstein H, Marsh DG, Platts-Mills TA, Thomas W. Allergen nomenclature. *Allergy*. 1995. 50:765-74.

Larsen JN. Allergen nomenclature: a need for the scientific community. *Arb Paul Ehrlich Inst Bundesamt Sera Impfstoffe Frankf A M*. 2006. 95:5-9.

Lee, H., Yildiz, G., Dos Santos, L.C., Jiang, S., Andrade, J.E., Engeseth, N.J., & Feng, H. Soy protein nano-aggregates with improved functional properties prepared by sequential pH treatment and ultrasonication. *Food Hydrocolloids*. 2016. 55, 200-209.

Leszczyńska, J., Łącka, A., & Bryszewska, M. The use of transglutaminase in the reduction of immunoreactivity of wheat flour. *Food and Agriculture Immunology*. 2006. 17, 105-113.

Li, Y., & Damodaran, S. In vitro Digestibility and IgE Reactivity of Enzymatically Cross-linked Heterologous Protein Polymers. *Food Chemistry*. 2016. 221, 1151-1157.

Marsh DG, Goodfriend L, King TP, Lowenstein H, Platts-Mills TA. Allergen nomenclature. *Bulletin of the World Health Organization*. 1986. 64:767-74.

Matalanis, A., Jones, O.G., & McClements, D.J. Structures biopolymer-based delivery systems for encapsulation, protection, and release of lipophilic compounds. *Food Hydrocolloids*. 2011. 25, 1865-1880.

Matoba, T., Hata, H. Relationship between bitterness of peptides and their chemical structures. *Agricultural Biological Chemistry*. 1972. 36, 1423-31.

Miller, K., Meredith, C., Selo, I., & Wal, J.M. Allergy to bovine β-lactoglobulin: specificity of immunoglobulin E generated in the Brown Norway rat to tryptic and synthetic peptides. *Clinical and Experimental Allergy*. 1999. 29, 1696-1704.

Ney, K. H. Prediction of bitterness of peptides from their amino acid composition. *Z Lebensm Unters Forsch*. 1971. 147:64-8.

O'Loughlin, I.B., Murray, B.A., Kelly, P.M., Fitzgerald, R.J., Brodkorb, A. Enzymatic hydrolysis of heat-induced aggregates of whey protein isolate. *Journal of Agricultural and Food Chemistry*. 2012. 60, 4895-4904.

O'Sullivan, D., & Fitzgerald, R. J. Physicochemical properties and residual antigenicity of transglutaminase cross-linked sodium caseinate hydrolysates. *International Dairy Journal*. 2012. 23, 1823.

Oldaeus, G., Anjou, K., Bjorksten, B., Moran, J.R., & Kjellman, N.I.M. Extensively and partially hydrolysed infant formulas for allergy prophylaxis. *Archives of Disease in Childhood*. 1997. 77, 4-10.

Olivier, C.E., Villas-Boas, M.B., Netto, F.M., & Zollner, R.D.L. Allergenicity of Bos d 5 in children with cow's milk allergy is reduced by transglutaminase polymerization. *Pediatric Allergy, Immunology, and Pulmonology*. 2012. 25, 30-33.

Pahud, J.J., Monti, J.C., & Jos, R. Allergenicity of whey-protein—its modification by tryptic invitro hydrolysis of the protein. *Journal of Pediatric and Gastroentrology Nutrition*. 1985. 4,408-413.

Palosuo, K., Varjonen, E., Nurkkala, J., Kalkkinen, N., Harvima, R., Reunala, T., & Alenius, H. Transglutaminase-mediated cross-linking of a peptic fraction of omega-5 gliadin enhances IgE reactivity in wheat-dependent, exercise-induced anaphylaxis. *Journal of Allergy and Clinical Immunology*. 2003. 111, 1386-1392.

Pedersen, M.H., Hansen, T.K., Sten, E., Seguro, K., Ohtsuka, T., Morita, A., Poulsen, L.K. Evaluation of the potential allergenicity of the enzyme microbial transglutaminase using the 2001 FAO/WHO Decision Tree. *Molecular Nutrition and Food Research*. 2004. 48, 434-440.

Pichot, R., Spyropoulos, F., & Norton, I.T. Mixed emulsifier stabilized emulsions: investigation of the effect of monoolein and hydrophilic silica particle mixtures on the stability against coalescence. *Journal of Colloid and Interface Science*. 2009. 329, 284-291.

Radauer C, Nandy A, Ferreira F. Goodman RE, Larsen JN, Lidholm J, Pomés A, Raulf-Heimsoth M, Rozynek P, Thomas WR, Breiteneder H. Update of the WHO/IUIS Allergen Nomenclature Database based on analysis of allergen sequences. *Allergy*. 2014. 69(4):413-419.

Ragno, V., Giampietro, P.G., Bruno, G., Businco, L. Allergenicity of milk protein hydrolysate formulas in children with cow's milk allergy. *European Journal of Pediatrics*. 1993. 152, 760-762.

(56) References Cited

PUBLICATIONS

Reddy, I.M., Kella, K.D., Kinsella, J.E. Structural and conformation basis of the resistance of beta-lactoglobulin to peptic and chymotryptic digestion. *Journal of Agricultural and Food Chemistry*. 1988. 36, 737-741.

Rosendal, A., & Barkholt, V. Detection of potentially allergenic material in 12 hydrolyzed milk formulas. *Journal of Dairy Science*. 2000. 83, 2200-2210.

Sampson, H.A., Bernhisel-Broadbent, J., Yang, E. & Scanlon, S.M. Safety of casein hydrolysate formula in children with cow milk allergy. *Journal of Pediatrics*. 1991. 118, 520-525.

Santipanichwong, R., Suphantharika, M., Weiss, J., & McClements, D.J. Core-shell biopolymer nanoparticles produced by electrostatic deposition of beet pectin onto heat-denatured □-lactoglobulin aggregates. *Journal of Food Science*. 2008. 73, N23-N30.

Schägger, H., & Von Jagow, G. Tricine-sodium dodecyl sulfate-polyacrylamide gel electrophoresis for the separation of proteins in the range from 1 to 100 kDa. *Analytical Biochemistry*. 1987. 166, 368-379.

Silvestre et al., Degree of Hydrolysis and peptide profile of whey proteins using pancreatin, Nutrie: rev. Soc. Bras. Alim. Nutr.—J. Brazilian Soc. Food Nutr., Sao Paulo, SP, 2013, v. 38, p. 278-290.

Stanic, D., Monogioudi, E., Dilek, E., Radosavljevic, J., Atanaskovic-Markovic, M., Vuckovic, O., Raija, L., Mattinen, M., Buchert, J., & Velickovic, T.C. Digestibility and allergenicity assessment of enzymatically crosslinked β-casein. *Molecular Nutrition and Food Research*. 2010. 54, 1273-1284.

Turgeon, S.L., Schmitt, C., & Sanchez, C. Protein-polysaccharide complexes and conjugates. *Current Opinion in Colloid and Interface Science*. 2007. 12, 166-178.

Tzoumaki, M.V., Moschakis, T., Kiosseoglou, V., & Biliaderis, C.G. Oil-in-w2ater emulsions stabilized by chitin nanocrystal particles. *Food Hydrocolloids*. 2011. 25, 1521-1529.

Wróblewska, B., Karamać, M., Amarowicz, R., Szymkiewicz, A., Troszyńska, A., & Kubicka, E. Immunoreactive properties of peptide fractions of cow whey milk protein after enzymatic hydrolysis. *International Journal of Food Science and Technology*. 2004. 39, 839-850.

Yu, M-A., & Damodaran, S. Kinetics of protein foam destabilization: evaluation of a method using bovine serum albumin. *Journal of Agricultural and Food Chemistry*. 1991a. 39, 1555-1562.

Yu, M-A., & Damodaran, S. Kinetics of destabilization of soy protein foams. *Journal of Agricultural and Food Chemistry*. 1991b. 39, 1563-1567.

Yusoff, A., & Murray, B.S. Modified starch granules as particle-stabilizers of oil-in-water emulsions. *Food Hydrocolloids*. 2011. 25, 42-55.

Zeiger RS, Sampson HA, Bock SA, Burks W, JR, Harden K, Noone S, Martin D, Leung S, Wilson G. Soy allergy in infants and children with IgE-associated cow's milk allergy. *Journal of Pediatrics*. 1999. 134, 614-622.

Zhu, H.; Damodaran, S. Heat-induced conformational changes in whey protein isolate and its relation to foaming properties. *Journal of Agricultural and Food Chemistry*. 1994a. 42, 846-855.

Zhu, H. and Damodaran, S. Proteose peptones and physical factors affect foaming properties of whey protein isolate. *Journal of Food Science*. 1994b. 59, 554-560.

Kalashnikova, I., Bizot, H., Cathala, B., & Capron, I. New Pickering emulsions stabilized by bacterial cellulose nanocrystals. *Langmuir*. 2011. 27, 7471-7479.

Larsen JN, Lowenstein H. *Allergen nomenclature*. The Journal of Allergy and Clinical Immunology. 1996. 97:577-8.

Malandain H. Transglutaminases: a meeting point for wheat allergy, celiac disease, and food safety. *European Annals of Allergy and Clinical Immunology*. 2005. 36, 1423-31.

* cited by examiner

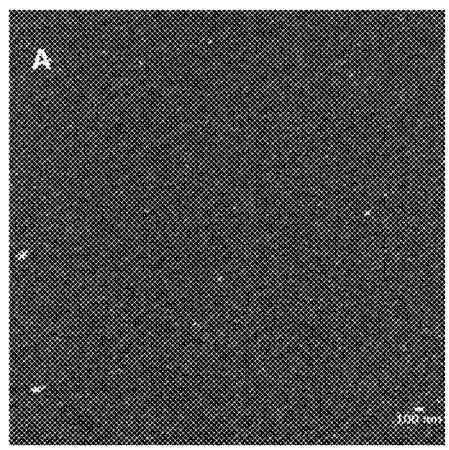
FIG. 10A
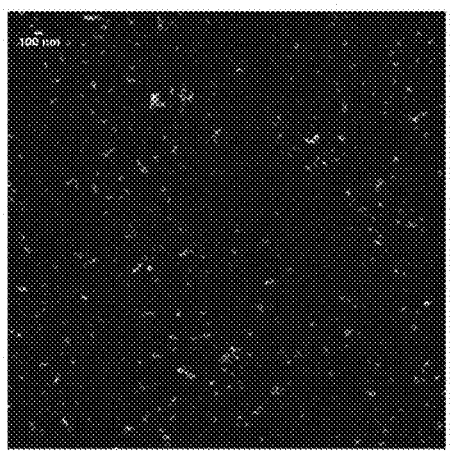
FIG. 10B1
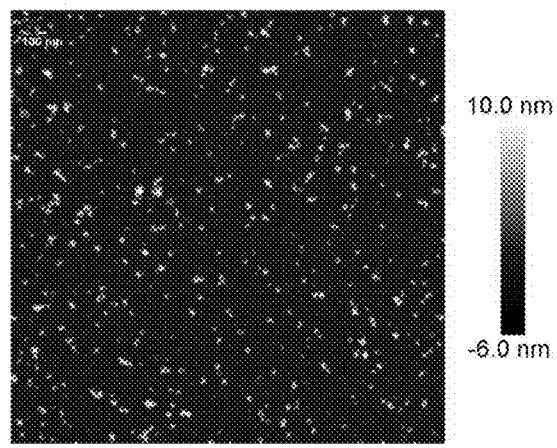
FIG. 10C1
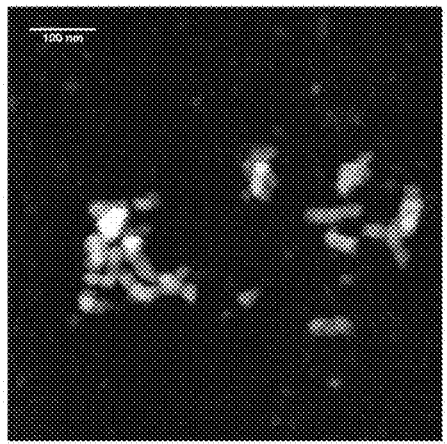
FIG. 10B2
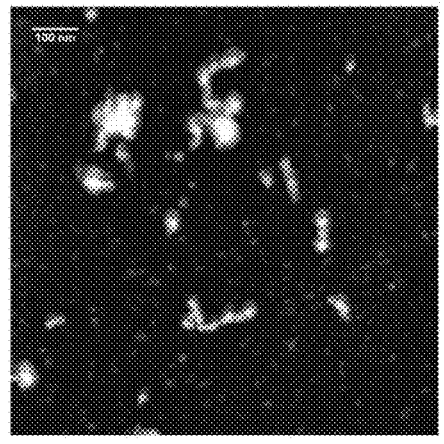
FIG. 10C2

Native WPI – Day 1

Native WPI – Day 27

WPIH – Day 1

WPIH – Day 27

US 11,634,462 B2

METHODS OF PROCESSING ß-LACTOGLOBULIN-CONTAINING COMPOSITIONS WITH THERMOLYSIN AND TRANSGLUTAMINASE

CROSS-REFERENCE TO RELATED APPLICATIONS

Priority is claimed to U.S. Application 62/674,186, filed May 21, 2018, which is incorporated herein by reference in its entirety.

FEDERAL FUNDING STATEMENT

This invention was made with government support under 2012-67017-30153 and 14-CRHF-0-6055 awarded by the USDA/NIFA. The government has certain rights in the invention.

BACKGROUND

Food allergies continue to be a growing problem. Food allergies are highly prevalent in children. Many children outgrow the allergies, but for some, the milk allergies continue into adulthood.

Most people who suffer from food allergies have immune reactions to certain proteins in the food. Strategies for reducing the allergenicity of such proteins include processing the protein with certain proteases to destroy the allergenic epitopes on the proteins. In order to ensure that these epitopes are disrupted enough to escape recognition from the immune system, however, the proteins are very heavily processed, leaving small peptides that can only be incorporated in formulas and protein drinks. These very small peptides also possess off flavors and smells.

Strategies for reducing the allergenicity of proteins that avoid the aforementioned problems are needed.

SUMMARY OF THE INVENTION

The invention is directed to methods of processing proteins. The invention comprises methods of hydrolyzing the protein with a proteolytic agent to generate hydrolyzed peptides and, optionally, crosslinking the hydrolyzed peptides with a transglutaminase to generate crosslinked peptides. A preferred proteolytic agent is thermolysin, which is unexpectedly effective at reducing the allergenicity of proteins, even with only partial hydrolysis of the protein. Crosslinking the hydrolyzed peptides further reduces allergenicity while generating polymerized structures suitable for incorporating into food products. The combination of hydrolyzing protein with thermolysin and crosslinking with transglutaminase can synergistically reduce allergenicity with respect to the either step used alone. The thermolysin-hydrolyzed and crosslinked peptides can be used to generate emulsions that are more stable than other protein- or peptide-based emulsions. The thermolysin-hydrolyzed and crosslinked peptides can also be used to generate foams. The resulting emulsions and foams are hypoallergenic. It is predicted that the crosslinked peptides of the invention, and the food products made therewith, have reduced off-flavors, smells, and allergenicity with respect to the non-crosslinked peptides.

The invention is also directed to products comprising the hydrolyzed peptides and/or the crosslinked peptides made using the methods described herein. The products include food products that comprise the hydrolyzed peptides and/or the crosslinked peptides, emulsions that comprise the hydrolyzed peptides and/or the crosslinked peptides, foams that comprise the hydrolyzed peptides and/or the crosslinked peptides, and/or food products that comprise the emulsions and/or foams.

The objects and advantages of the invention will appear more fully from the following detailed description of the preferred embodiment of the invention made in conjunction with the accompanying drawings.

BRIEF DESCRIPTION OF THE DRAWINGS

FIG. 9A: Lane 1, MW standard; Lane 2, WPI; Lane 3, WPI-TG; Lane 4, WPIH; Lane 5, WPIH-TG. FIG. 9B: Lane 1, MW standard; Lane 2, WPI; Lane 3, WPI-TG; Lane 4, WPIH; Lane 5, WPIH-TG.

FIGS. 10A-10C2. Topographical AFM images of (FIG. 10A) native WPI, (FIGS. 10B1 and 10B2), WPI-TG, and (FIGS. 10C1 and 10C2) WPIH-TG at pH 7. FIGS. 10B2 and 10C2 show expanded portions of FIGS. 10B1 and 10C1, respectively.

DETAILED DESCRIPTION OF THE INVENTION

Figure 1A:
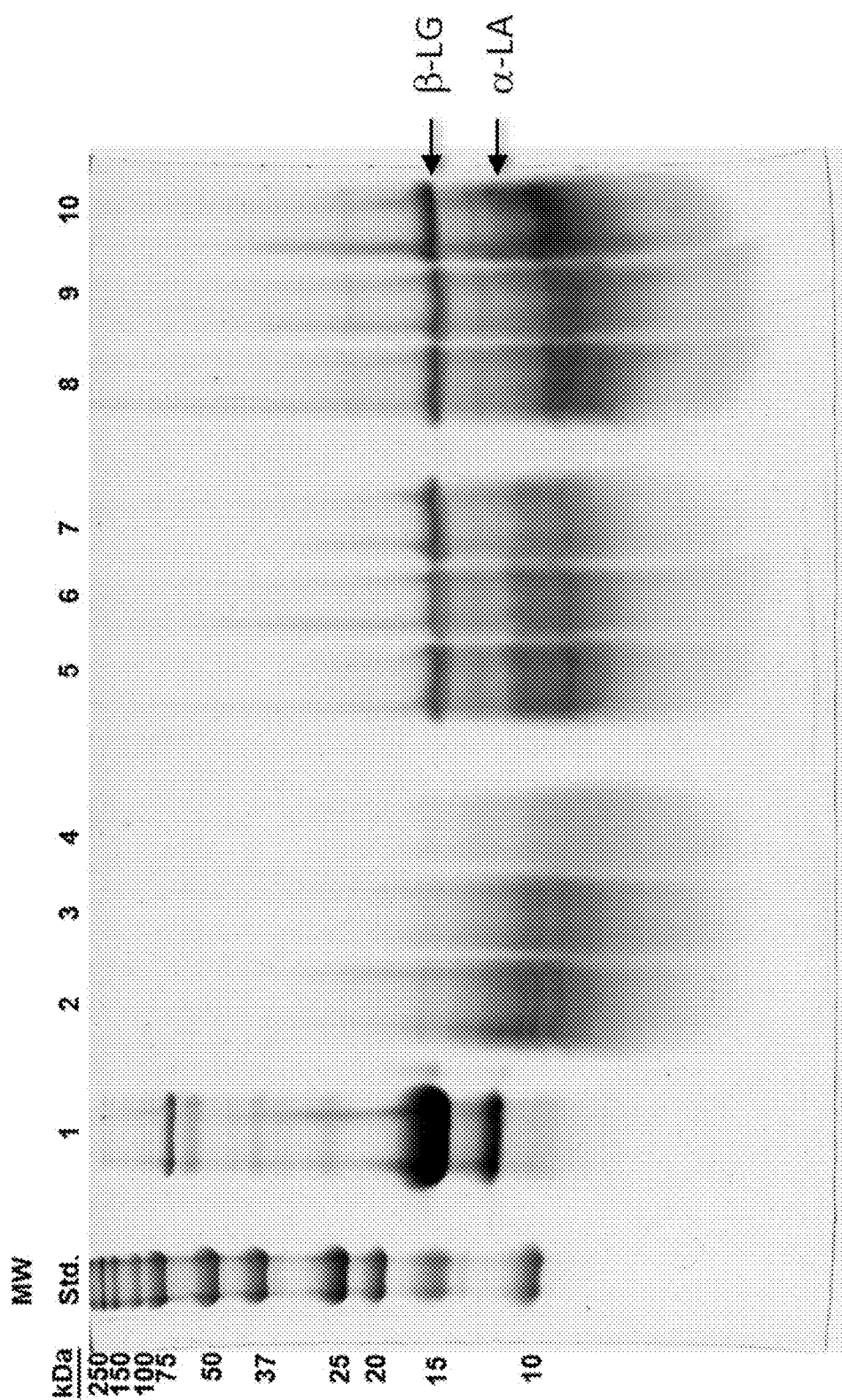
FIG. 1A. Tricine-SDS-PAGE of WPI (whey protein isolate) and WPI hydrolysates produced under various substrate-to-enzyme ratios and hydrolysis times: Lane 1, WPI control; Lane 2, WPI+thermolysin, 2000:1, 5 min; Lane 3, WPI+thermolysin, 1500:1, 5 min; Lane 4, WPI+thermolysin, 400:1, 5 min; Lane 5, WPI+trypsin, 200:1, 30 min; Lane 6, WPI+trypsin, 100:1, 30 min; Lane 7, WPI+trypsin, 100:1, 60 min; Lane 8, WPI+chymotrypsin, 200:1, 30 min; Lane 9, WPI+chymotrypsin, 100:1, 30 min; Lane 10, WPI+chymotrypsin, 100:1, 60 min.

The invention, in part, is directed methods of processing proteins. The proteins processed in the method can comprise any polypeptide, whether purified, semi-purified, or unpurified. The protein can comprise any wholly intact natural, recombinant, or synthetic polypeptide; any processed forms thereof, including any denatured, cleaved, partially digested, or partially hydrolyzed forms; and/or any compositions comprising same.

In some versions, the protein comprises an allergenic protein. "Allergenic protein" refers to any polypeptide capable of eliciting an immune response, such as an IgE response, in an animal. Allergenic proteins include any protein approved and officially recognized as an allergen by the Allergen Nomenclature Sub-Committee of the World Health Organization and International Union of Immunological Societies (WHO/IUIS), or any processed form thereof. See, e.g., Marsh et al. (Marsh D G, Goodfriend L, King T P, Lowenstein H, Platts-Mills T A. Allergen nomenclature. *Bull World Health Organ* 1986; 64:767-74), King et al. (King T P, Hoffman D, Lowenstein H, Marsh D G, Platt-Mills T A, Thomas W R. *Allergen Nomenclature*. 1994; 72:797-800. Bulletin World Health Organization), King et al. (King T P, Hoffman D, Lowenstein H, Marsh D G, Platts-Mills T A, Thomas W. Allergen nomenclature. WHO/IUIS Allergen Nomenclature Subcommittee. *Int Arch Allergy Immunol* 1994; 105:224-33), King et al. (King T P, Hoffman D, Lowenstein H, Marsh D G, Platts-Mills T A, Thomas W. Allergen nomenclature. *Allergy* 1995; 50:765-74), Larsen et al. (Larsen J N, Lowenstein H. Allergen nomenclature. *J Allergy Clin Immunol* 1996; 97:577-8), Chapman et al. (Chapman M D. *Allergen Nomenclature*. In "Allergens and Allergen Immunotherapy" 3rd Edition. Editors, R F Lockey, S C Bukantz & J Bousquet, pp 51-64, 2004. Marcel Decker), Chapman (Chapman M D. *Allergen Nomenclature*. In "Allergens and Allergen Immunotherapy" 4th Edition. Editors, Richard F. Lockey, Dennis K. Ledford, pp 47-58. 2008. Informa Healthcare, New York), Larsen (Larsen J N. Allergen nomenclature: a need for the scientific community. Arb Paul Ehrlich Inst Bundesamt Sera Impfstoffe Frankf A M 2006; 95:5-9), Chapman et al. (Chapman M D, Pomés A, Breiteneder H, Ferreira F. Nomenclature and structural biology of allergens. *J Allergy Clin Immunol* 2007; 119:414-20), Breiteneder H, Chapman M D. Allergen Nomenclature. In Allergens and Allergen Immunotherapy: Subcutaneous, sublingual and oral. 5th Edition. Edited by Richard F. Lockey and Dennis K. Ledford. CRC Press, Taylor and Francis Group, Boca Raton, Fla., USA, 2014, pp 37-49), Radauer et al. (Radauer C, Nandy A, Ferreira F, Goodman R E, Larsen J N, Lidholm J, Pomés A, Raulf-Heimsoth M, Rozynek P, Thomas W R, Breiteneder H. Update of the WHO/IUIS Allergen Nomenclature Database based on analysis of allergen sequences. *Allergy*, 2014, 69(4):413-419). Such allergenic proteins can be found in the WHO/IUIS database, accessible via www.allergen.org.

Examples of allergenic protein include milk protein, legume protein, tree nut protein, and grain protein. "Milk protein," "legume protein," "tree nut protein," and "grain protein" refer to protein purified from, extracted from, obtained from, or contained in milk, legume, and grain, respectively. Examples of milk protein include whey protein isolate, which includes β-lactoglobulin, and casein, which includes β-casein. Examples of legume protein include soy protein and peanut protein, which include allergenic cupins (Ara h 1), prolamins (Ara h 2, 6, 7, 9), profilins (Ara h 5), and Bet v-1-related proteins (Ara h 8). Commercially relevant forms of soy protein include soy protein isolate and soy protein concentrate. Examples of tree nut protein include Brazil nut protein, almond protein, chestnut protein, hazelnut protein, pine nut protein, and walnut protein, which comprise allergenic seed storage proteins (vicilins, legumins, albumins), plant defense-related proteins, and profilins. Examples of grain protein include wheat protein, barley protein, rye protein, triticale protein, and oat protein, which comprise gluten (variously also referred to as gliadin in wheat, hordein in barley, secalin in rye, and avenin in oats).

The methods of processing proteins comprise a step of hydrolyzing the protein with a proteolytic agent to generate hydrolyzed peptides. As used herein, "hydrolyzing" broadly refers to any mechanism of cleaving a given protein (polypeptide) into smaller polypeptides, regardless of whether or not water is consumed in the reaction. "Polypeptide" and "peptide" are used interchangeably herein.

In some versions, the protein comprises an allergenic protein, and the hydrolyzing is performed under conditions effective for the hydrolyzed peptides to have reduced allergenicity with respect to the protein. Such conditions include suitable enzyme concentrations, reaction time, reaction temperature, and solvent conditions (pH, salt concentration, etc.) all of which are ascertainable from a practitioner in the art in view of the following examples. "Reduced allergenicity" as used herein refers to a reduction in the ability to induce an immune response and can occur through a reduction in IgE reactivity among other mechanisms.

The proteolytic agent may comprise any agent capable of cleaving a given protein into smaller polypeptides. Suitable proteolytic agents include non-enzymatic proteolytic agents and enzymatic proteolytic agents. Non-enzymatic proteolytic agents include mineral acids such as hydrochloric acid, cyanogen bromide, BNPS-skatole, formic acid, hydroxylamine ($NH_2OH$), iodosobenzoic acid, trifluoroacetic acid, NTCB (2-nitro-5-thiocyanobenzoic acid), and others. Enzymatic proteolytic agents include proteases. Suitable proteases include any serine proteases, cysteine proteases, threonine proteases, aspartic proteases, glutamic proteases, metalloproteases, and asparagine peptide lyases. Exemplary suitable proteases include aeromonolysin, arg-C proteinase, asp-N endopeptidase, aureolysin, caspases (e.g., caspase 1, caspase 2, caspase 3, caspase 4, caspase 5, caspase 6, caspase 7, caspase 8, caspase 9, caspase 10), chymotrypsin, clostripain (clostridiopeptidase B), enterokinase, factor Xa, glutamyl endopeptidase, granzyme B, lysC lysyl endopeptidase (Achromobacter proteinase I), lysN peptidyl-lys metalloendopeptidase, mycolysin, neutrophil elastase, pepsin, proline-endopeptidase, proteinase K, pseudolysin, Staphylococcal peptidase I, tobacco etch virus protease, thrombin, and trypsin.

Particularly preferred proteases include thermolysins. "Thermolysin" refers to enzymes falling under Enzyme Commission (EC) number 3.4.24.27. Various thermolysins include the neutral proteinases from *Bacillus thermoproteolyticus* and *Geobacillus stearothermophilus*, and recombinant versions thereof. The terms "thermoase," "thermoase Y10," and "TLN" are also used to refer to thermolysins. Thermolysins specifically catalyze the hydrolysis of peptide bonds containing hydrophobic amino acids. An exemplary thermolysin is commercially available from Sigma-Adrich (St. Louis, Mo.) under catalog number P1512.

Thermolysins are particularly effective in reducing the allergenicity of protein such as whey protein and other types of protein, both when used alone and when used in combination with a translglutaminase. In certain versions of the invention, for example, thermolysins are capable of hydrolyzing the protein into hydrolyzed peptides having an IgE immunoreactivity less than 29% of the IgE immunoreactivity of the protein, such as less than 28% of the IgE immunoreactivity of the protein, less than 27% of the IgE immunoreactivity of the protein, less than 26% of the IgE immunoreactivity of the protein, less than 25% of the IgE immunoreactivity of the protein, less than 24% of the IgE immunoreactivity of the protein, less than 23% of the IgE immunoreactivity of the protein, less than 22% of the IgE immunoreactivity of the protein, less than 21% of the IgE immunoreactivity of the protein, less than 20% of the IgE immunoreactivity of the protein, or less than 19% of the IgE immunoreactivity of the protein.

In some versions of the invention, the hydrolyzing comprises only partially hydrolyzing the protein such that the resulting hydrolyzed peptides are partially hydrolyzed peptides. "Partially hydrolyzing" refers to hydrolysis of protein with a given proteolytic agent to a degree of hydrolysis (DH) of less than 95% of the maximal degree of hydrolysis obtainable with the given proteolytic agent. In various versions of the invention, the protein is hydrolyzed to a degree of hydrolysis of less than 90%, less than 80%, less than 70%, less than 60% less than 50%, less than 40%, less than 30%, less than 20%, less than 10%, less than 1% of the maximal degree of hydrolysis obtainable with the proteolytic agent used in the hydrolysis step. "Degree of hydrolysis" as used herein refers to the proportion of cleaved peptide bonds in a protein hydrolysate and is determined according to the pH-Stat method (Adler-Nissen, J. (1986). Enzymatic hydrolysis of food proteins. New York; Elsevier Applied Science Publishers).

In various versions of the invention, the hydrolyzing comprises partially hydrolyzing the protein to a degree of hydrolysis of from about 0.001%, 0.01%, 0.1%, 1%, 2%, 5%, 10%, 20%, 30%, 40%, 50%, 60%, 70%, 80%, 90%, 95% or more to less than about 1%, 2%, 5%, 10%, 20%, 30%, 40%, 50%, 60%, 70%, 80%, 90%, 95% or more. Exemplary ranges include a degree of hydrolysis of from about 0.1% to about 10%, such as from about 0.5% to about 5%, or from about 1% to about 3%.

In various versions of the invention, the hydrolyzing comprises partially hydrolyzing the protein to generate partially hydrolyzed peptides wherein a proportion of the total mass of the hydrolyzed peptides comprise peptides having a particular size. For example, at least about 5%, 10%, 15%, 25%, 30%, 35%, 40%, 45%, 50%, 55%, 60%, 65%, 70%, 75%, 80%, 90%, 95%, or more of the total mass of the partially hydrolyzed peptides may comprises peptides having a size of from about 0.5 kDa, 1 kDa, 2 kDa, 3 kDa, 4 kDa, 5 kDa, 10 kDa, 15 kDa, or 20 kDa to about 5 kDa, 10 kDa, 25 kDa, 50 kDa, 75 kDa, or 100 kDa. In some versions, about 5%, 10%, 15%, 25%, 30%, 35%, 40%, 45%, 50%, 55%, 60%, 65%, 70%, 75%, 80%, 90%, 95%, or more of the total mass of the partially hydrolyzed peptides comprises of from about 3 kDa to about 10 kDa. The proportion of the total mass of the hydrolyzed peptides comprising peptides having a particular size is determined for the purposes herein according to the size exclusion chromatography method of Adjonu et al. (Adjonu R, Doran G, Torley P, Agboola S. Screening of whey protein isolate hydrolysates for their dual functionality: influence of heat pre-treatment and enzyme specificity. *Food Chem.* 2013 Feb. 15; 136(3-4):1435-43).

An optional but preferred step in the methods described herein include crosslinking the hydrolyzed peptides with a transglutaminase to generate crosslinked peptides. A transglutaminase is an enzyme that catalyzes the formation of an isopeptide bond between a free amine group (e.g., protein- or peptide-bound lysine) and the acyl group at the end of the side chain of protein- or peptide-bound glutamine. Such enzymes are classified as EC 2.3.2.13. Transglutaminases are commercially available from Sigma-Aldrich (St. Louis, Mo.) under catalog number T5398 and Ajinomoto Food Ingredients (Eddyville, Iowa, USA).

In some versions, the protein originally hydrolyzed comprises an allergenic protein, the hydrolyzed peptides retain at least some allergenicity, and the crosslinking of the hydrolyzed peptides is performed under conditions effective for the crosslinked peptides to have reduced allergenicity with respect to the hydrolyzed peptides. Such conditions include suitable enzyme concentrations, substrates, reaction time, reaction temperature, and solvent conditions (pH, salt concentration, etc.) all of which are ascertainable from a practitioner in the art in view of the following examples.

Crosslinking with a transglutaminase is particularly effective in reducing the allergenicity of hydrolyzed peptides generated from hydrolyzing whey protein and other types of protein with a thermolysin. In certain versions of the invention, for example, transglutaminases are capable of crosslinking hydrolyzed peptides to generate crosslinked peptides having an IgE immunoreactivity less than 53% of the IgE immunoreactivity of the hydrolyzed peptides, such as less than 50% of the IgE immunoreactivity of the hydrolyzed peptides, less than 45% of the IgE immunoreactivity of the hydrolyzed peptides, less than 45% of the IgE immunoreactivity of the hydrolyzed peptides, less than 40% of the IgE immunoreactivity of the hydrolyzed peptides, less than 35% of the IgE immunoreactivity of the hydrolyzed peptides, or less than 30% of the IgE immunoreactivity of the hydrolyzed peptides.

In some versions of the invention, the protein comprises an allergenic protein, and the hydrolyzing and the crosslinking are performed under conditions effective for the crosslinked peptides to have reduced allergenicity with respect to the protein. Such conditions include suitable enzyme concentrations, substrates, reaction time, reaction temperature, and solvent conditions (pH, salt concentration, etc.) all of which are ascertainable from a practitioner in the art in view of the following examples.

The combination of hydrolyzing with a thermolysin and crosslinking with a transglutaminase is particularly effective in reducing the allergenicity of whey protein and other types of protein. In various versions of the invention, for example, the combination of hydrolyzing with a thermolysin and crosslinking with a transglutaminase, is capable of generating crosslinked peptides having an IgE immunoreactivity less than 31% of the IgE immunoreactivity of the protein, such as less than 30% of the IgE immunoreactivity of the protein, less than 25% of the IgE immunoreactivity of the protein, less than 20% of the IgE immunoreactivity of the protein, less than 15% of the IgE immunoreactivity of the protein, less than 10% of the IgE immunoreactivity of the protein, or less than 7% of the IgE immunoreactivity of the protein.

Hydrolyzing with a thermolysin and crosslinking with a transglutaminase in some versions is synergistically effective in reducing allergenicity compared to the additive effects of each step taken individually.

The hydrolyzed and crosslinked peptides can be used in further steps to generate certain products, such as food products, emulsions, and/or emulsions included in food products. The hydrolyzed and/or crosslinked peptides, for example, can be used to make emulsions by mixing the hydrolyzed peptides and/or the crosslinked peptides in an aqueous phase with an oil phase to generate the emulsion. The emulsion can be an oil-in-water emulsion or a water-in-oil emulsion. As shown in the examples, emulsions made with the hydrolyzed and/or crosslinked peptides of the present invention have better storage stability then emulsions made with other types of polypeptides.

Various examples of food products that can include the hydrolyzed and/or crosslinked peptides of the invention (either directly or in the form of an emulsion) comprise protein shakes, infant formulas, soymilk, bread, and solid meat substitutes, such as tofu, tempeh, seitan, textured vegetable protein, etc. It is predicted that the food products of the invention will be less allergic than corresponding food products made with other protein sources. It is predicted that the food products of the invention will possess less potent or off flavors and smells than corresponding food products made with other protein sources or will avoid them altogether. It is predicted that the structure of the crosslinked peptides of the invention will permit the generation of more highly structured food products (such as solid food products) than hydrolyzed peptides.

The elements and method steps described herein can be used in any combination whether explicitly described or not.

All combinations of method steps as used herein can be performed in any order, unless otherwise specified or clearly implied to the contrary by the context in which the referenced combination is made.

As used herein, the singular forms "a," "an," and "the" include plural referents unless the content clearly dictates otherwise.

Numerical ranges as used herein are intended to include every number and subset of numbers contained within that range, whether specifically disclosed or not. Further, these numerical ranges should be construed as providing support for a claim directed to any number or subset of numbers in that range. For example, a disclosure of from 1 to 10 should be construed as supporting a range of from 2 to 8, from 3 to 7, from 5 to 6, from 1 to 9, from 3.6 to 4.6, from 3.5 to 9.9, and so forth.

All patents, patent publications, and peer-reviewed publications (i.e., "references") cited herein are expressly incorporated by reference to the same extent as if each individual reference were specifically and individually indicated as being incorporated by reference. In case of conflict between the present disclosure and the incorporated references, the present disclosure controls. The incorporation by reference specifically includes but is not limited to U.S. Application 62/674,186, filed May 21, 2018; Damodaran et al. 2017 (Damodaran S, Li Y. A two-step enzymatic modification method to reduce immuno-reactivity of milk proteins. *Food Chem.* 2017 Dec. 15; 237:724-732); and Chen et al. 2018 (Chen A, Tanidjaja I, Damodaran S. Nanostructure and functionality of enzymatically repolymerized whey protein hydrolysate. *Food Chem.* 2018 Aug. 1; 256:405-412).

It is understood that the invention is not confined to the particular construction and arrangement of parts herein illustrated and described, but embraces such modified forms thereof as come within the scope of the claims.

EXAMPLES

Example 1

A Two-Step Enzymatic Modification Method to Reduce Immunoreactivity of Milk Proteins

Summary

A two-step enzymatic approach to reduce immunoreactivity of whey protein isolate and casein has been studied. The method involves partial hydrolysis of proteins with proteases, followed by repolymerization with microbial transglutaminase. Whey protein isolate partially hydrolyzed with chymotrypsin, trypsin, or thermolysin retained about 80%, 30%, and 20% of the original immunoreactivity, respectively. After repolymerization the immunoreactivity was about 45%, 35%, and 5% of the original immunoreactivity, respectively. The immunoreactivity of hydrolyzed and repolymerized casein was negligible compared to native casein. The repolymerized products were partially resistant to in vitro digestion. Peptides released during digestion of repolymerized thermolysin-whey protein hydrolysate had less than 5% immunoreactivity, whereas those of whey protein control exhibited a sinusoidal immunoreactivity ranging from 5-20%. Peptides released during digestion of repolymerized thermolysin-casein hydrolysates had no immunoreactivity. These results indicated that it is possible to produce hypoallergenic milk protein products using the two-step enzymatic modification method involving thermolysin and transglutaminase.

Introduction

Cow's milk allergy is very prevalent among children under the age of three. A significant number of infants allergic to cow's milk protein also develop allergy to other food proteins (Zeiger et al., 1999; Ahn et al 2003; Burks et al., 1994). Protein allergy in children is mainly attributed to IgE-mediated hypersensitivity (Exl & Fritsche 2001). Elicitation of allergenic response of a protein could be either due to a sequence-specific epitope or conformational epitope. Studies have shown that partial enzymatic hydrolysis significantly reduced the allergenicity of proteins (Pahud et al., 1985; Businco et al., 1993; Bindels & Boerma, 1994; Oldaeus et al., 1997; Halken et al., 2000; Rosendal & Barkholt, 2000). However, the definition of 'partial' hydrolysis is quite arbitrary in terms of the peptide length profile. As a consequence, some partially hydrolyzed protein products have been shown to cause severe allergic reactions in some children (Rosendal & Barkholt, 2000; Ragno et al., 1993) due to presence of intact linear epitopes in hydrolysates. Furthermore, protein hydrolysates generally taste bitter (Wróblewska et al., 2004; Matoba & Hata, 1972; Ney, 1971) and lack desirable functional properties, particularly gelation and texturization, essential for improving sensorial properties of hypoallergenic food products.

A promising enzymatic approach to reduce the allergenicity of proteins is enzymatic crosslinking using enzymes such as transglutaminase (Pedersen et al., 2004; Malandain 2005; Buchert et al., 2008; O'Sullivan & FitzGerald, 2012; Li & Damodaran, 2016). Transglutaminase (TGase) catalyzes a crosslinking reaction between glutamine and lysine residues in proteins. (Han & Damodaran, 1996; DeJong & Kippelman, 2002; Agyare & Damodaran, 2010). This crosslinking reaction could be inter-molecular and intra-molecular. When inter-molecular crosslinking occurs, which is the predominant route, the reaction produces branched-chain protein polymers (Han & Damodaran, 1996). It is likely that this crosslinking reaction might alter both conformational and linear epitopes and thus render the modified protein to be less responsive to IgE binding. However, studies have shown that polymerization of milk proteins, viz., β-casein and β-lactoglobulin using microbial transglutaminase resulted only in marginal decrease in their immunoreactivity (Stanic et al., 2010; Olivier et al., 2012; Li & Damodaran, 2016). On the other hand, transglutaminase crosslinking of wheat flour caused a 70% reduction in glutenin immune reactivity, whereas that of ω-gliadin actually increased in non-competitive ELISA (Leszczynska et al 2006; Palosuo et al 2003). In a recent study, Li and Damodaran (2016) reported that immunoreactivity of protein components in heterologous crosslinked protein polymers was significantly lower than in homologous crosslinked protein polymers. However, a significant fraction of conformational and linear epitopes were still intact and were readily accessible to antibody binding in some heterologous protein conjugates, such as crosslinked whey protein-casein, soy protein-casein, and soy protein-whey protein polymers.

The hypothesis of the present study is that a combination of initial partial hydrolysis of protein using a suitable protease followed by TGase-catalyzed repolymerization of the hydrolysate could produce hypo-immune-reactive protein polymers. This two-step enzymatic approach would completely disrupt both the integrity and accessibility of allergenic epitopes to IgE in proteins. This is predicted also to eliminate the bitter flavor often associated with protein hydrolysates. To test this hypothesis, we used trypsin, chymotrypsin, and thermolysin to partially hydrolyze whey protein isolate (WPI) and sodium caseinate (CN) under controlled conditions and repolymerized the resulting hydrolysate using TGase to produce branched chain polymers. The immunoreactivity of these hydrolysates and polymers were investigated using protein specific ELISA. The digestibility of these branched chain polymers under simulated gastric-duodenal conditions and the immunoreactivity of the digests were also studied.

Materials and Methods

Materials

Commercial sodium caseinate was from Agroupur Ingredients (Product No. SR:9710; La Crosse, Wis., USA) and whey protein isolate (WPI) was from Davisco Foods International Inc., (BiPRO, Lot No. JE045-5-420, Eden Prairie, Minn., USA). Thermolysin (Type X, 30-175 units/mg protein), trypsin (from porcine pancreas, type 2, 1600 BAEE units/mg solid; 1800 ATEE units/mg solid), α-chymotrypsin (from bovine pancreas, 83.9 units/mg solid; 96 units/mg protein), porcine stomach mucosa pepsin (EC 3.4.23.1, activity: 2100 units/mg solid, 2600 units/mg protein), and porcine pancreatin (P7545) were from Sigma-Aldrich (St. Louis, Mo., USA). Microbial TGase (Activa-TI, 99% maltodextrin and 1% TGase; 100 units/g of solid) was from Ajinomoto Food Ingredients (Eddyville, Iowa, USA). The enzyme was used without further purification.

AgraQuant® F.A.S.T Casein ELISA test kit was purchased from Romer Labs Inc. (Union, Mo., USA). RIDASCREEN® β-lactoglobulin test kit was purchased from R-Biopharm AG (Darmstadt, Germany).

WPI Hydrolysis and Repolymerization

For digestion with thermolysin, a 10% (w/w) solution of WPI at pH 7.0 was treated with thermolysin at enzyme-to-substrate weight ratios of 1/400, 1/1500 and 1/2000 and incubated at 37° C. for 5 min. The hydrolysis was stopped by heating in a boiling water bath for 8 min.

It is known that whey proteins are partly resistant to proteolysis by trypsin and chymotrypsin. Therefore, to facilitate proteolysis with chymotrypsin and trypsin, first a 1% (w/w) solution of WPI was heat denatured in a boiling water bath for 30 min, cooled and lyophilized. A 5% (w/w) solution of this denatured WPI in water at pH 7.0 was treated with trypsin or chymotrypsin at various enzyme-to-substrate ratios and incubation time combinations, i.e., 1:200 for 30 min; 1:100 for 30 min, and 1:100 for 1 h at 37° C. The hydrolysis reaction was stopped by heating in boiling water bath for 8 min and then lyophilized.

Repolymerization of the WPI hydrolysates using TGase was performed as follows: A 10% thermolysin hydrolysate, and 5% trypsin and chymotrypsin hydrolysates were incubated separately with TGase (100 units/g of substrate) in the presence of 5 mM β-mercaptoethanol for 24 h at 37° C. Heating the mixture in a boiling water bath for 8 min stopped the reaction.

Casein Hydrolysis and Repolymerization

Aliquots of a 5% w/w solution of sodium caseinate in deionized water at pH 7.0 were incubated with thermolysin at an enzyme to substrate weight ratio of 1:1500 for 5 min, 10 min, and 15 min at 37° C. and hydrolysis was terminated by heating in a boiling water bath for 8 min and then lyophilized. Casein was hydrolyzed with chymotrypsin and trypsin at an enzyme-to-substrate weight ratio of 1:200 under conditions similar to thermolysin hydrolysis. Timepoint samples were taken after 5 min, 10 min, and 15 min followed by heat inactivation of the enzyme in boiling water for 8 min and then the samples were lyophilized. TGase-catalyzed repolymerization of the above hydrolysates was performed as described for WPI hydrolysate.

Soy Protein Isolate (SPI) Hydrolysis and Repolymerization

Thermolysin hydrolysis: 1:200 enzyme to SPI weight ratio, 37 C for 30 min, hydrolysis terminated by boiling at 100° C. for 8 min.

Trypsin and chymotrypsin hydrolysis: A 5% SPI solution was first heat denatured in boiling water for 30 min, cooled down to 37° C. and then treated with trypsin or chymotrypsin at an enzyme to SPI ratio (w/w) of 1:100 for 30 min. Hydrolysis was stopped by incubating in boiling water bath for 8 min.

Transglutaminase reaction: The hydrolysate was treated with transglutaminase at an enzyme to substrate weight ratio of 100 Units/g substrate at 37° C. for 24 h, followed by inactivation of the enzyme in boiling water for 8 min.

In Vitro Digestion of Repolymerized Protein Polymers

In vitro digestion of repolymerized-protein polymers under simulated gastro-intestinal conditions was performed as described elsewhere (Dupont et al, 2010; Fu, Abbott, & Hatzos, 2002; Li & Damodaran, 2016). Briefly, protein samples were dissolved (2%) in 0.15 M NaCl and the pH was adjusted to 2.5 with 1N HCl to simulate the gastric fluid conditions. Porcine stomach mucosa pepsin was added at a 1:20 enzyme-to-protein weight ratio and the mixtures were incubated at 37° C. for 1 h. To create the intestinal condition, the pH of the gastric digest was raised to 6.5 using 1N NaOH and bile salt and bile-Tris were added so that the final concentrations of these components were 1.85 mM and 26.1 mM, respectively. To this mixture was added porcine pancreatin at a 1:20 enzyme-to-protein ratio and the mixture was incubated at 37° C. Samples withdrawn at various time intervals during the intestinal phase of digestion were placed in a boiling water bath for 10 min to terminate digestion. The immunoreactivity of the digests was analyzed using protein-specific ELISA kits.

Electrophoresis

Sodium dodecyl sulfate-polyacrylamide gel electrophoresis (SDS-PAGE) of protein samples under reducing conditions was carried out as described previously (Agyare & Damodaran, 2010) using a 12.5% acrylamide separating and a 4.5% acrylamide stacking slab gel in a Mini-PROTEAN 3 apparatus (Bio-Rad Laboratories, Hercules, Calif., USA). A mixture of molecular weight standards (11-170 kDa) (Sigma-Aldrich Co., St. Louis, Mo., USA) was also run along with the samples.

To better resolve low molecular weight peptides in some cases, tris/tricine polyacrylamide gel electrophoresis was also performed according to Schagger & Von Jalow (1987) using a 16.5% acrylamide separating and a 4% acrylamide stacking slab gel. A mixture of molecular weight standards (6-180 kDa) (NOVEX, Life technologies, CA, USA) was also run along with the samples.

ELISA

Immunoreactivity of control and treated protein samples were studied using commercially available protein-specific ELISA kits. The experiments were performed as described elsewhere (Li & Damodaran, 2016). In the case of WPI, which is a mixture of β-lactoglobulin and α-lactalbumin, the immune-reactivity of WPI was determined using a β-lactoglobulin-specific competitive ELISA kit. In all ELISA experiments, the intensity of color products released in the titer wells was measured at 450 nm in an automated Spectra MAX plus ELISA plate reader (Molecular Devices Inc., Sunnyvale, Calif., USA). These experiments were done in duplicate and statistical analyses (analysis of variance) of the results were performed using Excel.

Results and Discussion

Figure 1B:
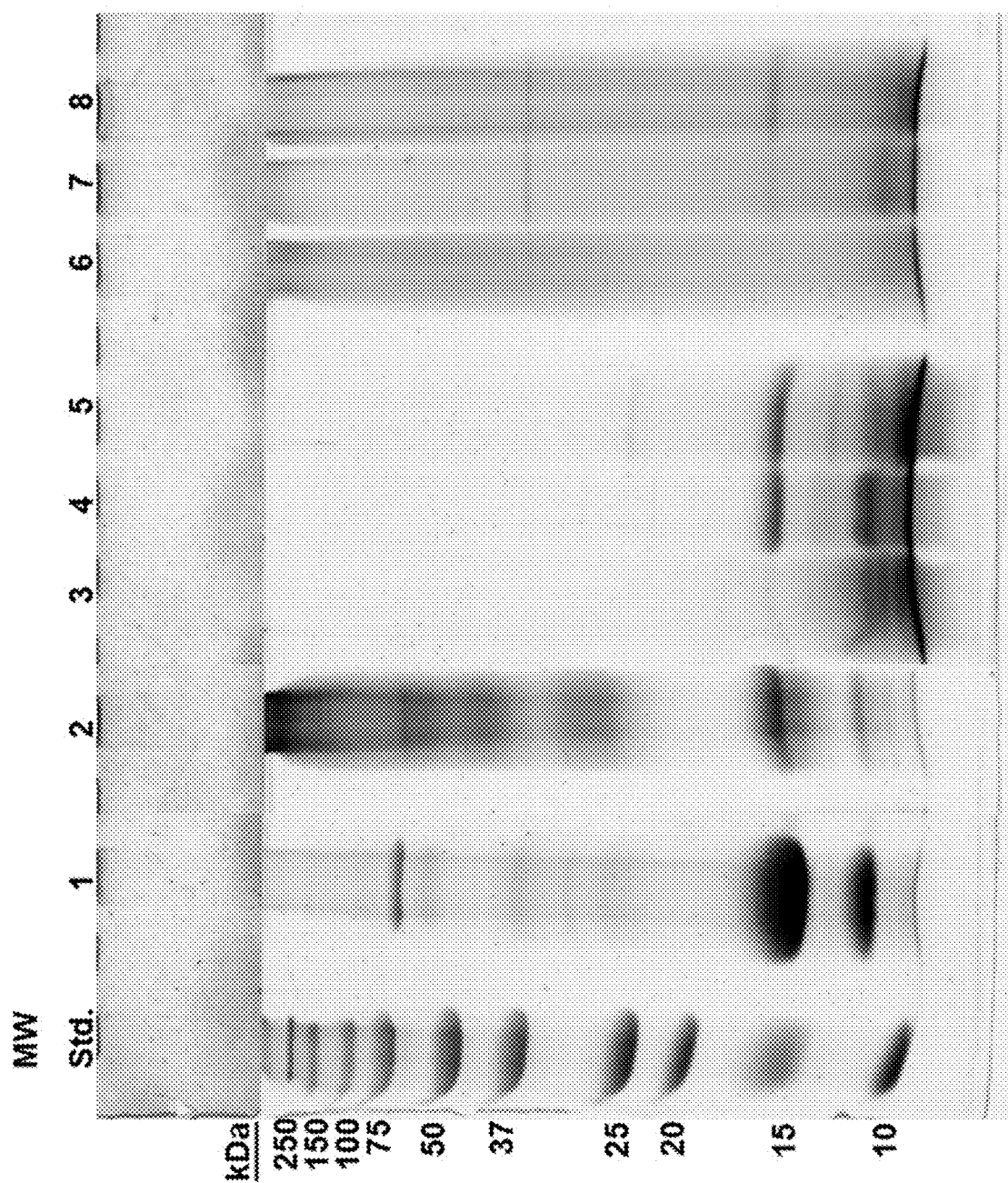
FIG. 1B. SDS-PAGE of WPI, WPI hydrolysates produced under specified optimum substrate-to-enzyme ratios and hydrolysis times, and WPI hydrolysates repolymerized using transglutaminase (TGase). Lane 1, WPI control; Lane 2, WPI+TGase; Lane 3, WPI+thermolysin, 1500:1, 5 min; Lane 4, WPI+trypsin, 100:1, 30 min; Lane 5, WPI+chymotrypsin, 100:1, 30 min; Lane 6, WPI+thermolysin+TGase; Lane 7, WPI+trypsin+TGase; Lane 8 WPI+chymotrypsin+TGase.
Figure 1C:
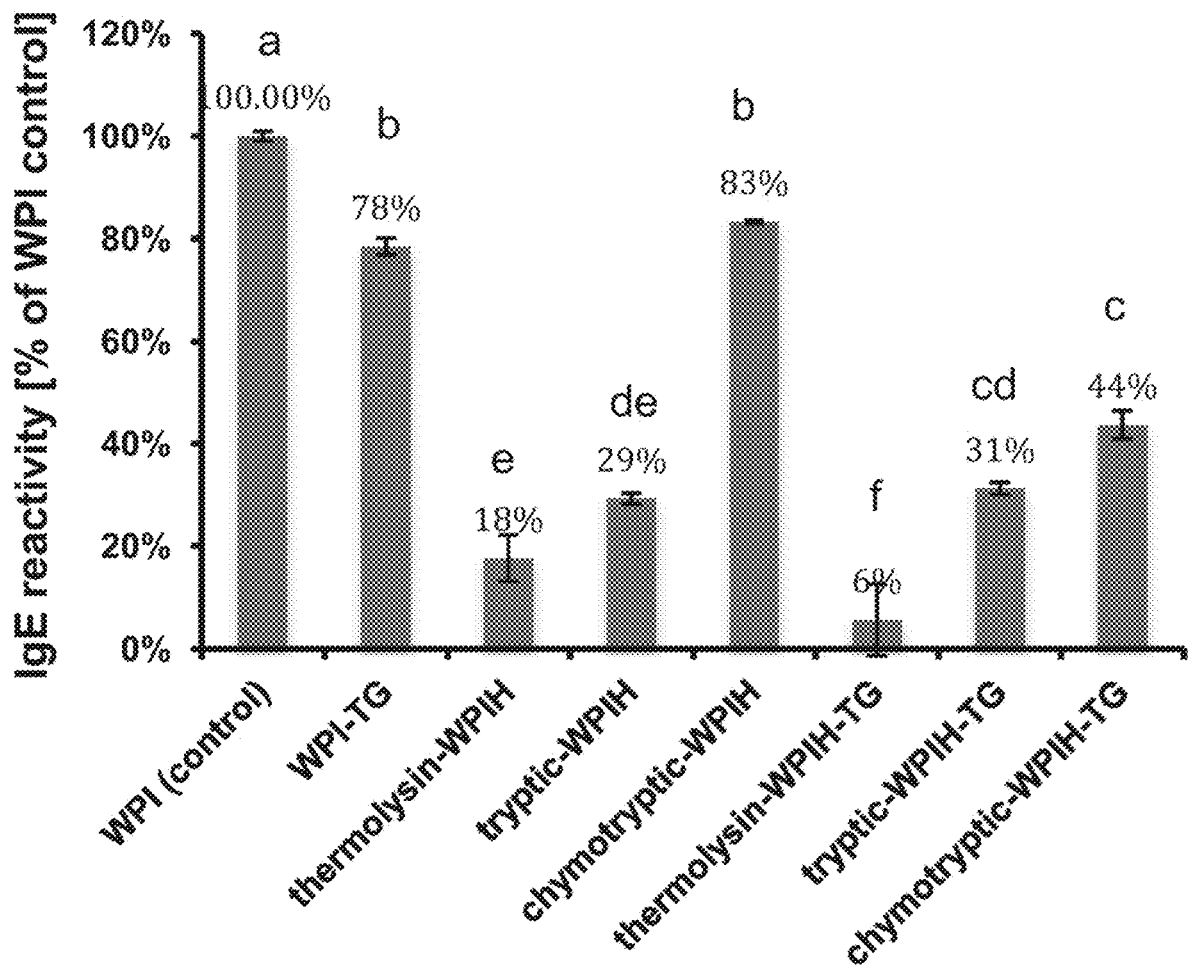
FIG. 1C. IgE reactivity of various enzyme-treated WPI products expressed on the basis of the immune-reactivity of WPI control. Statistical analysis was performed using Tukey HSD test. a-e: Mean values of columns with different letters imply that they are significantly different ($p>0.05$).

WPI Hydrolysis

β-LG is known to be very resistant to digestive enzymes, especially trypsin and chymotrypsin, but its susceptibility improves upon thermal denaturation (Reddy et al., 1988; O'Loughlin et al., 2012). Therefore, a pre-heat treatment (see methods) was employed to improve the susceptibility of WPI to proteolysis. Hydrolysis of WPI by trypsin, chymotrypsin, and thermolysin under various conditions is shown in FIGS. 1A-1C. It should be noted that even after thermal denaturation in a boiling water bath for 30 min, β-LG in WPI was not completely hydrolyzed by trypsin and chymotrypsin even when hydrolyzed at an enzyme-to-substrate ratio of 1:100 for 1 h, whereas α-LA was completely hydrolyzed to smaller peptides (FIG. 1A, lanes 7 and 10). On the other hand, thermolysin was very effective in hydrolyzing both β-LG and α-LA in native WPI to about 3-12 kDa peptides even at an enzyme-to-substrate ratio of 1:2000 for 5 min (FIG. 1A, lane 2). WPI was completely hydrolyzed to small peptides at a thermolysin-to-substrate weight ratio of 1:400, as is evident from faint staining of bands in the SDS-PAGE profile (FIG. 1A, lane 4). Extensive hydrolysis of WPI may release significant amounts of short peptides with no glutamine residue. Such peptides would not participate in TGase-mediated repolymerization reaction. Thus, limited proteolysis that results in release of peptides in the MW range of 3-10 kDa is desirable to increase the yield of crosslinked polymers during TGase-catalyzed repolymerization of hydrolysates. Accordingly, the following hydrolysis conditions were selected for the three proteases: An enzyme-to-substrate ratio of 1:1500 and 5 min was used for thermolysin and an enzyme-to-substrate ratio of 1:100 and 30 min was used for trypsin and chymotrypsin.

Immunoreactivity of WPI Hydrolysates and Their Repolymerized Products

The native WPI and hydrolyzed WPI formed large polymers when treated with TGase (FIG. 1B). The polymerized native WPI showed new smeared bands in the molecular weight range of ~30 to ~400 kDa (FIG. 1B, lane 2). However, some (~10%) monomeric β-LG and α-LA were present in the polymerized sample even after 24 h of treatment with TGase. A similar observation had been made in previous studies (Han & Damodaran, 1996; Li & Damodaran, 2016). In the case of hydrolysates, thermolysin was very effective in hydrolyzing β-LG and α-LA (FIG. 1B, lane 3), whereas a small amount of intact β-LG and α-LA was left unhydrolyzed in tryptic and chymotryptic hydrolysates (FIG. 1B, lanes 4 and 5). When these hydrolysates were treated with TGase, the intensities of residual β-LG and α-LA bands were greatly reduced, indicating that they along with other peptides in the hydrolysates were copolymerized to high molecular weight polymers by TGase (FIG. 1B, lanes 7 and 8); however, it has to be noted that some residual amount of β-LG was still present along with appearance of a β-LG dimer band (FIG. 1B, lanes 7 and 8). The molecular weight of the heterogeneous crosslinked polymers ranged from approximately 6 kDa to well over 400 kDa as evident from the continuous smeared bands in SDS-PAGE. This wide molecular size distribution might be the result of limited availability of glutamine and lysine residues in peptides of the hydrolysates. Whey proteins contain a low glutamine-to-lysine ratio. For instance, β-LG contains 10 glutamine and 15 lysine residues, whereas α-LA contains 5 glutamine and 12 lysine residues. As a result, depending on their distribution in the primary sequence and the sites of cleavage by the proteases, it is theoretically possible that some of the peptides released in the hydrolysates might be devoid of glutamine residues. It would not be possible for such peptides to take part in the TGase-catalyzed polymerization reaction. The low molecular weight polymers in FIG. 1B, Lanes 6-8 might be such polypeptides.

The immunoreactivity of β-LG in WPI and its fragments containing allergenic epitopes in various enzyme treated WPI samples is shown in FIG. 1C. TGase polymerization of native WPI (WPI-TG) decreased its immunoreactivity to 78% of that of native WPI control. Since according to the SDS-PAGE profile only a small amount (~10%) of intact β-LG was present in the WPI-TG sample (FIG. 1B, lane 2), only a 22% reduction in immunoreactivity of the WPI-TG polymers suggests that most of the antigenic epitopes of native β-LG were not disrupted during the polymerization reaction and they were still easily accessible to antibody binding. Among the WPI hydrolysates, the immunoreactivity of the chymotryptic hydrolysate (chymotryptic-WPIH) was 83% and that of the tryptic-WPIH was about 29% of the WPI control.

The high immune-reactivity of chymotryptic-WPIH cannot be totally due to residual β-LG in the sample, because this residual amount was less than 10% of the control WPI whereas the immune reactivity of the sample was 83% (FIG. 1B, lanes 1 and 5). This is also true of the tryptic-WPIH. Therefore, these greater than expected immunoreactivity of tryptic and chymotryptic hydrolysates might be due to presence of intact linear epitopes in the peptide fragments, especially in chymotryptic-WPIH. On the other hand, the thermolysin hydrolysate (thermolysin-WPIH) exhibited the lowest (18%) immunoreactivity, suggesting that among the three proteases thermolysin was more effective in disrupting allergenic epitopes in WPI. Miller et al (1999) reported that the IgE binding epitopes of β-LG are found in segments 21-40, 41-60, 107-117, and 148-162 of the protein. The amino acid sequences of these segments are SLAMA-ASDISLLDAQSAPLR (SEQ ID NO:1), VYVEELKPT-PEGDLEILLQK (SEQ ID NO:2), MENSAEPEQS (SEQ ID NO:3), and RLSFNPTQLEEQCHI (SEQ ID NO:4), respectively. It should be noted that the interior parts of segments 21-40, 107-117, and 148-162 do not contain lysine, arginine, tyrosine, tryptophan, and phenylalanine residues and therefore it is more likely that these IgE binding epitopes might remain intact in a partially hydrolyzed tryptic-WPIH and chymotryptic-WPIH hydrolysates. On the other hand, however, since thermolysin cleaves on the N-side of peptide bonds of hydrophobic residues, the segments 21-40, 41-60, and 148-162, which contain several hydrophobic residues, would be disrupted by thermolysin hydrolysis and thus peptides containing these allergenic epitopes would not be present in the thermolysin-WPIH hydrolysate. The low immunoreactivity of thermolysin-WPIH compared to tryptic-WPIH and chymotryptic-WPIH hydrolysates (FIG. 1C) substantiates these arguments.

Upon repolymerization using TGase, the immunoreactivity of the TG polymers of thermolysin WPI hydrolysate (thermolysin-WPIH-TG) decreased from 18% to 6%, and that of the TG polymers of chymotryptic WPI hydrolysate (chymotryptic-WPIH-TG) decreased from 83% to 44%, indicating that the immunoreactive epitopes were further disrupted and/or have become masked by the crosslinking reaction. In contrast, repolymerization of tryptic hydrolysate (tryptic-WPIH-TG) did not significantly change its immunoreactivity, which remained at 29-31%. (FIG. 1C), suggesting that the configuration of the branched-chain polymers in tryptic-WPIH-TG was different from those of the thermolysin-WPIH-TG and chymotryptic-WPIH-TG polymers and the epitopes were as easily accessible in the repolymerized sample as in the hydrolysate to antibody binding. Since trypsin cleaves proteins at the C-end of lysine (and arginine) residues, lysine would be at the C-terminal of the peptides in the hydrolysate. As a result, when treated with TGase, the crosslinking would occur between the amine group of C-terminal (exo) lysine residues (or the N-terminal amino group of peptides) and the amide group of endo-glutamine residues, resulting in an exo-endo type only crosslinking between peptides. In contrast, in the cases of chymotryptic and thermolysin hydrolysates, which do not cleave at lysine and glutamine residues, endo-endo type would be major crosslinking between endo-lysine and endo-glutamine residues along with some exo-endo crosslinking between exo N-terminal amine and endo glutamine residues of peptides. These differences in the mode of crosslinking might create branched-chain polymer structures in which accessibility of allergenic epitopes to IgE binding may vary. Nevertheless, the data in FIG. 1C clearly indicate that initial hydrolysis of WPI with thermolysin, followed by repolymerization of the hydrolysate with TGase drastically reduces the immunoreactivity of the neo-protein polymers.

Immunoreactivity of In Vitro Digested TG-Polymers of WPI Hydrolysate

Since trypsin is site specific for lysine and arginine residues, and chymotrypsin is specific for tryptophan, tyrosine, and phenylalanine, the repolymerized tryptic-WPIH-TG and chymotryptic-WPIH-TG samples would not contain cleavage sites for trypsin and chymotrypsin, respectively, during the duodenal phase of digestion. Therefore, we limited our studies only to examining the immunoreactivity of the thermolysin-WPIH-TG polymers.

Figure 2A:
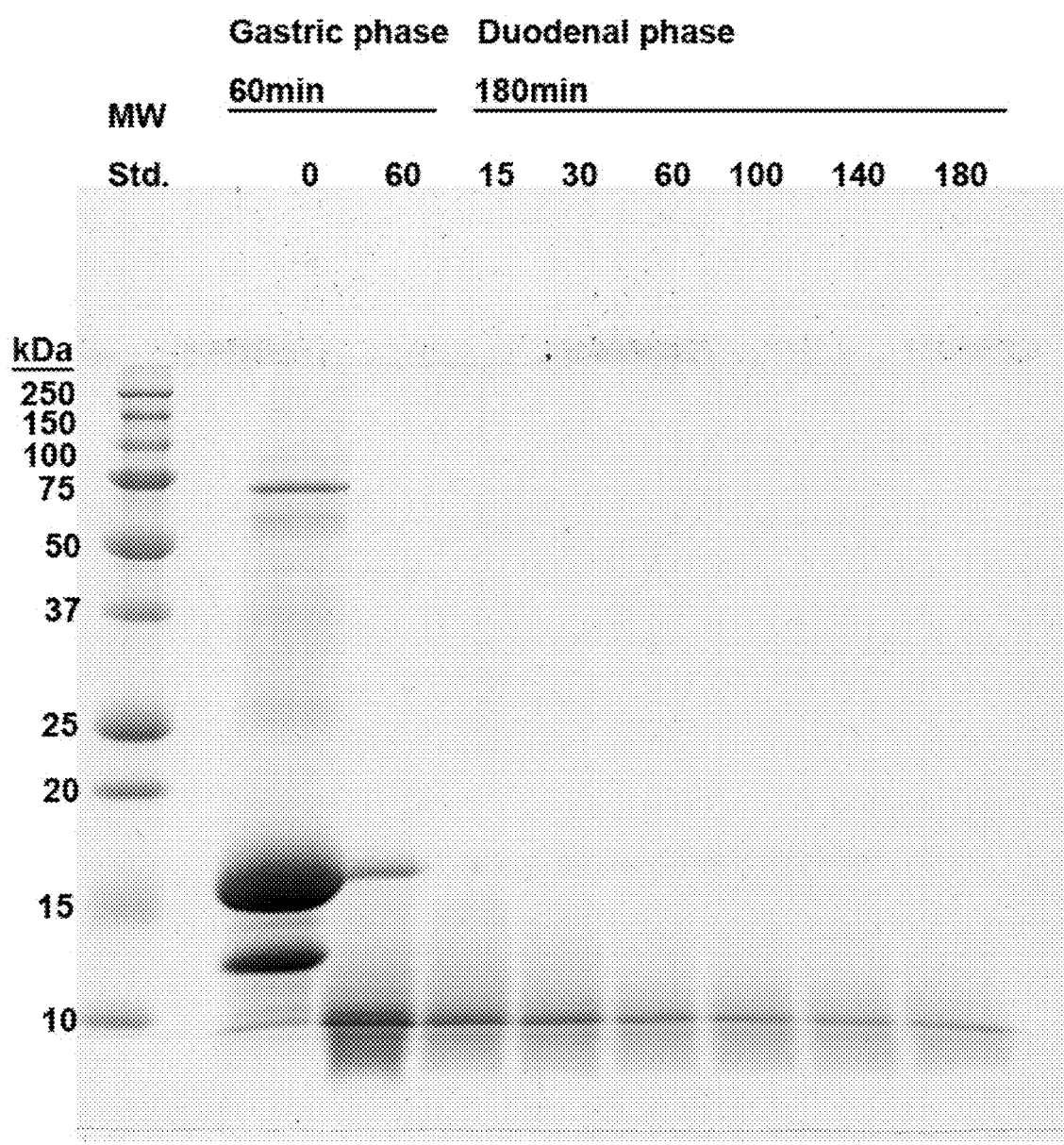
FIG. 2A. SDS-PAGE profiles of peptides released from native WPI during time course of in vitro digestion under simulated gastric and duodenal digestion conditions. The gastric digestion was performed for 60 min, followed by 180 min of duodenal phase digestion.
Figure 2B:
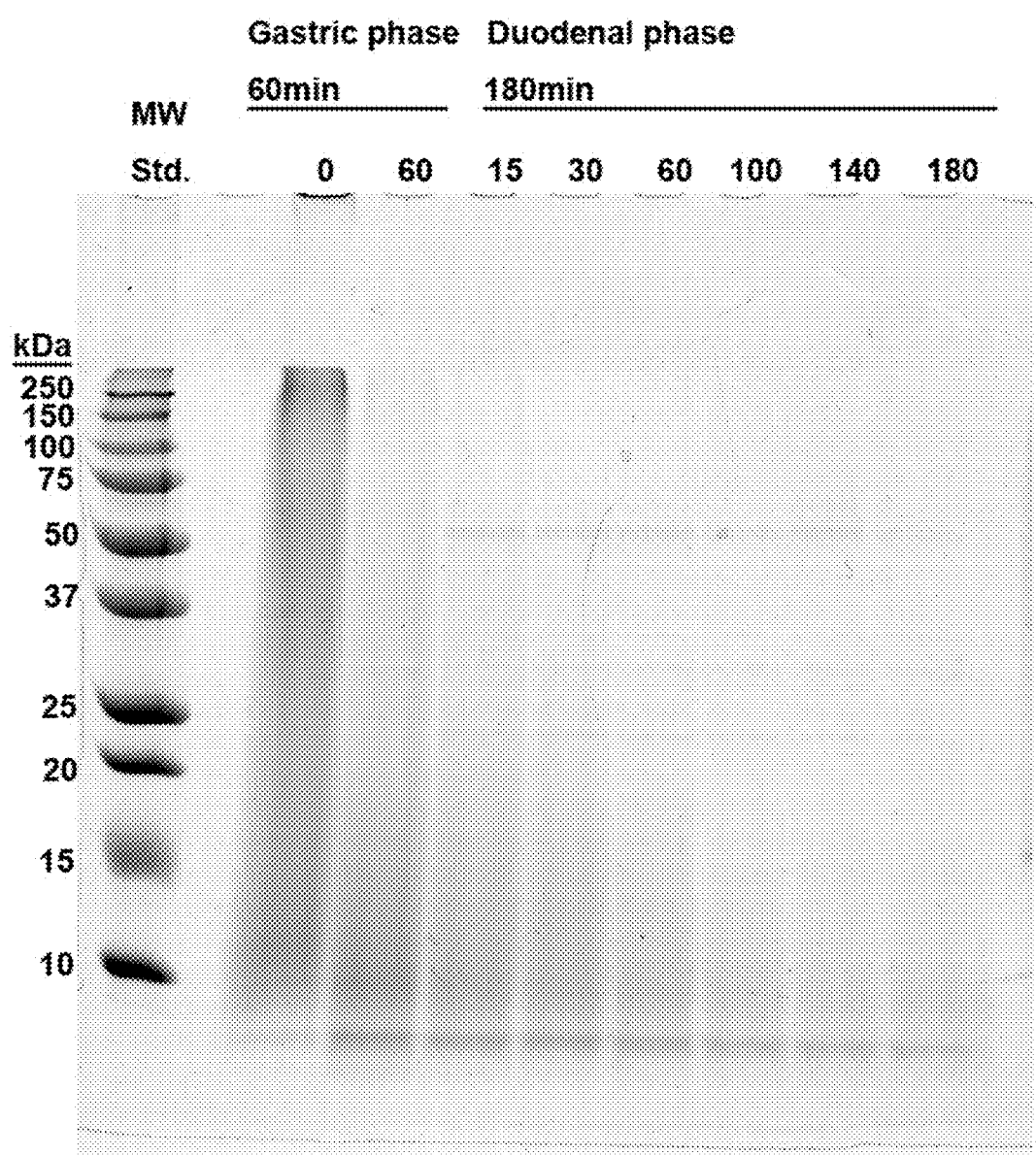
FIG. 2B. SDS-PAGE profiles of peptides released from thermolysin-WPIH-TG polymers during time course of in vitro digestion under simulated gastric and duodenal digestion conditions.
Figure 2C:
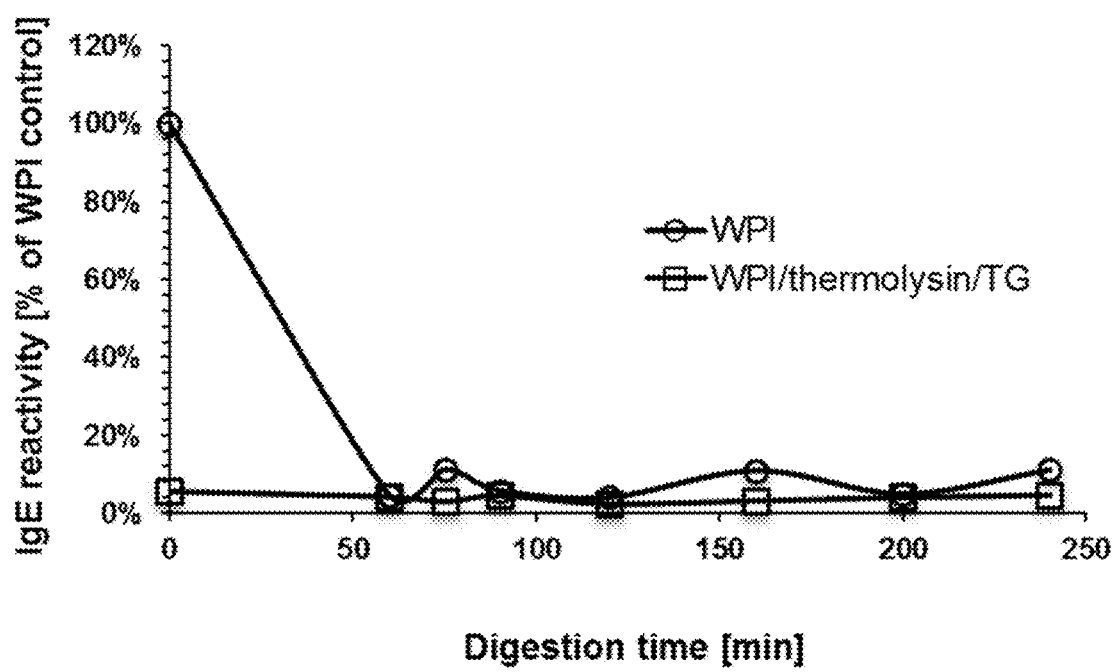
FIG. 2C. Immunoreactivity of peptides released during time course of simulated gastric and duodenal phase digestion of thermolysin-WPIH-TG polymers.

The extent of hydrolysis as a function of time of native WPI and thermolysin-WPIH-TG polymers under simulated gastric and duodenal conditions is shown in FIGS. 2A-C. The native WPI was rapidly hydrolyzed to small peptides with only a small amount of β-LG left undigested after the first 60 min of gastric phase digestion. The digest contained a ~10 kDa polypeptide as the major component (FIG. 2A). Digestion of polypeptides continued during the duodenal phase digestion, however this ~10 kDa polypeptide appeared to be resistant to digestion, as evidenced from its very slow disappearance during 180 min of duodenal phase digestion. In contrast, although most of the thermolysin-WPIH-TG polymers were digested during 60 min of gastric phase digestion, the digest still contained some high molecular weight polymers, as evidenced from a smeared band in the molecular weight range of 5-100 kDa after 60 min of gastric digestion (FIG. 2B). During the duodenal phase of digestion, these remaining high molecular weight polymers were very slowly digested down to lower molecular weight polymers. However, a smeared band in the range of 5-10 kDa molecular weight was still present even after 180 min of hydrolysis (FIG. 2B). These seemingly un-digestible peptides might be remnants of branched-chain polymers that could not be further digested because of blocked lysine residues and/or inaccessibility of the remaining peptide bonds to proteases and peptidases of pancreatin due to steric constraints imposed by branched chains.

The immunoreactivity of peptides released during the time course of in vitro digestion is shown in FIG. 2C. While the immunoreactivity of the native WPI digests exhibited a sinusoidal pattern, i.e., rising and falling with digestion time, within the range of 5% to 20% reactivity, the immunoreactivity of the thermolysin-WPIH-TG polymer digest was constant at ~5% throughout the 240 min digestion period, indicating that gastro-duodenal digestion of thermolysin-WPIH-TG polymers did not release any IgE reactive peptides. Previously, it has been shown that when WPI-TG polymers (i.e., intact WPI polymerized with TGase) were subjected to simulated gastro-duodenal digestion, its digest also exhibited a sinusoidal immunoreactivity pattern similar to native WPI ranging from 5% to 20% as a function of digestion time (Li & Damodaran, 2016). The absence of this pattern with the thermolysin-WPIH-TG polymers indicates that all potential linear antigenic epitopes were effectively eliminated/disrupted in this two-step enzymatically modified WPI. The allergenicity of WPI and partially hydrolyzed WPI often observed in patients might be due to this residual 20% immunoreactivity of the digested products, and this level of immunoreactivity might be sufficient enough to trigger a strong gut immune response. However, it is possible that the low (<5%) immunoreactivity of thermolysin-WPIH-TG polymers digests is predicted not to elicit a strong response from the gut immune system of patients allergic to milk proteins.

Casein Hydrolysate and its Repolymerized Products

Figure 3A:
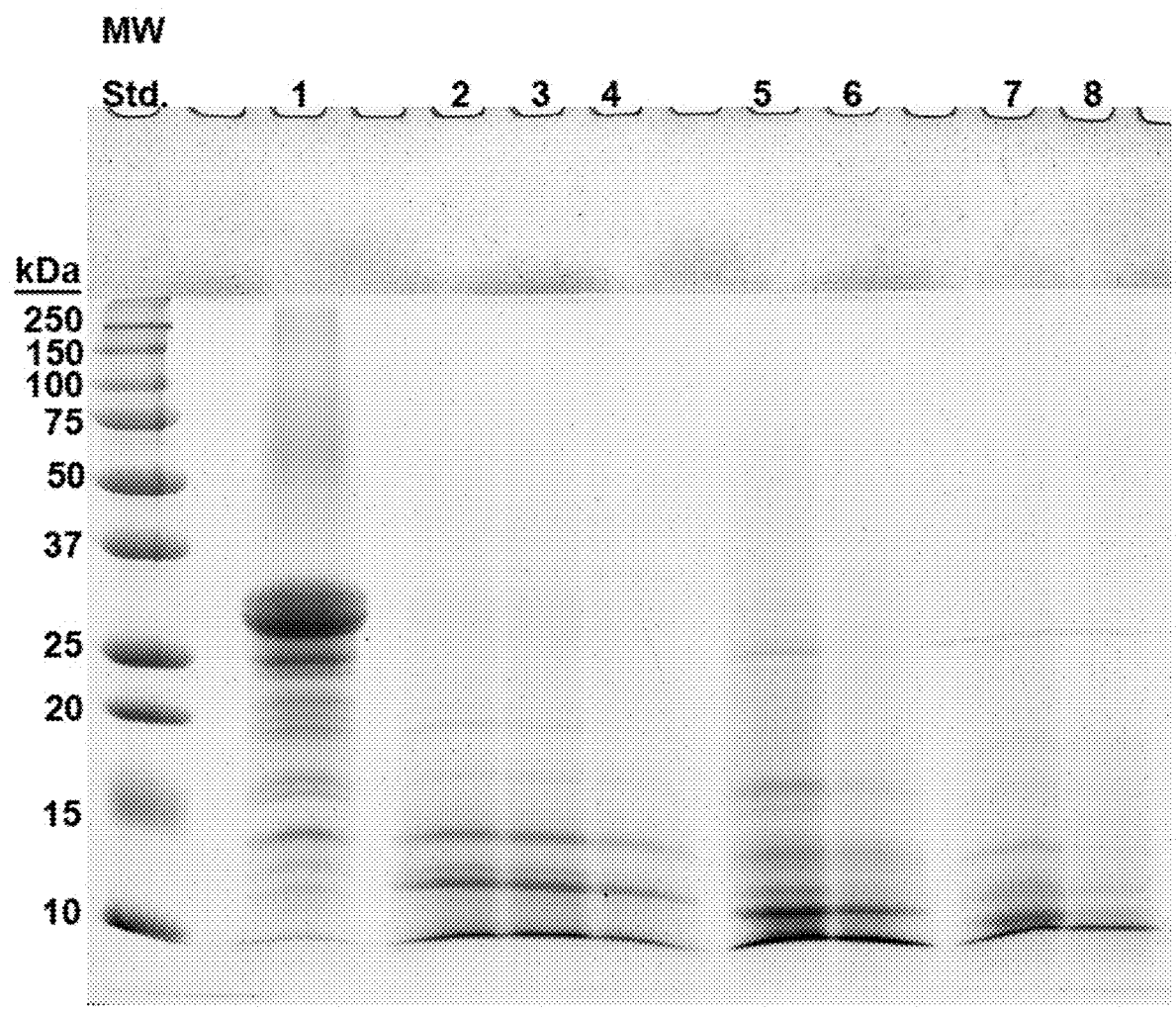
FIG. 3A. SDS-PAGE of casein and casein hydrolysates produced under various substrate-to-enzyme ratios and hydrolysis times: Lane 1, Casein control; Lane 2, casein+thermolysin, 2000:1, 5 min; Lane 3, casein+thermolysin, 1500:1, 5 min; Lane 4, casein+thermolysin, 800:1, 5 min; Lane 5, casein+trypsin, 400:1, 10 min; Lane 6, casein+trypsin, 200:1, 10 min; Lane 7, casein+chymotrypsin, 200:1, 10 min; Lane 8, casein+chymotrypsin, 100:1, 10 min.

Caseins are highly flexible proteins and, as a result, are readily digested by proteases. Therefore, optimization of partial hydrolysis conditions to produce peptide fragments in the MW range of 3-10 kDa was necessary for the subsequent TGase-catalyzed repolymerization reaction. FIG. 3A shows the SDS-PAGE profile of casein digested with thermolysin, trypsin, and chymotrypsin at various enzyme-to-substrate ratios and hydrolysis times. Among the three thermolysin hydrolysates, those corresponding to 1:2000 and 1:1500 enzyme-to-substrate ratios showed no noticeable difference in the SDS-PAGE profile, while the 1:800 sample was over hydrolyzed as seen from the reduced intensity of the coomassie blue staining. To choose between 1:2000 and 1:1500 enzyme-to-substrate ratios, the immunoreactivity of both these hydrolysates were tested using casein-specific ELISA. The result showed that both these samples had very low immunoreactivity (data not shown). However, the one hydrolyzed at 1:1500 enzyme-to-substrate ratio had lower activity than the one at 1:2000 enzyme-to-substrate ratio. Therefore, the 1:1500 enzyme-to-substrate ratio was chosen for subsequent steps. Similarly, the 1:400 enzyme-to-substrate ratio/10 min and the 1:200 enzyme-to-substrate ratio/10 min hydrolysis conditions were chosen as optimum conditions for tryptic and chymotryptic digestions, respectively.

Figure 3B:
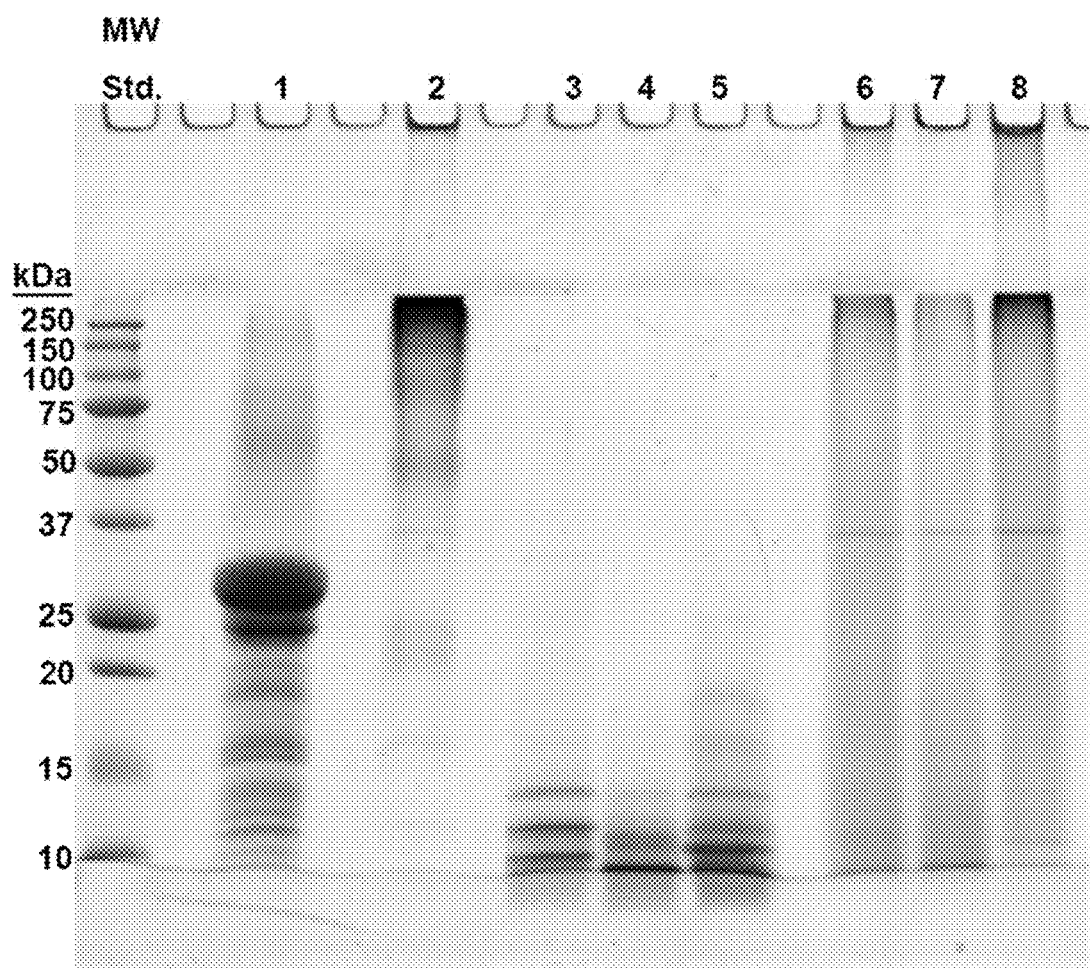
FIG. 3B. SDS-PAGE of casein, casein hydrolysates produced under specified optimum substrate-to-enzyme ratios and hydrolysis times, and casein hydrolysates repolymerized using TGase. Lanes 1, casein control; Lane 2, casein+TGase; Lane 3, casein+thermolysin, 1500:1, 5 min; Lane 4, casein+trypsin, 400:1, 10 min; Lane 5, 5% casein+chyomotrypsin, 200:1, 10 min; Lane 6, casein+thermolysin+TGase; Lane 7, casein+trypsin+TGase; Lane 8, casein+chyomotrypsin+TGase.

The SDS-PAGE profiles of thermolysin, tryptic, and chymotryptic hydrolysates of casein (CNH) and their repolymerized polymers (CNH-TG) are shown in FIG. 3B. Under the hydrolysis condition used, the molecular weights of peptides in all the three hydrolysates were in the range of about 10 to 20 kDa (FIG. 3B, lanes 3-5). Upon treatment with TGase, casein and its hydrolysates were able to form large MW polymers (FIG. 3B, lanes 2, 6-8). Some of these polymers could not pass through the stacking and separating gels. In the cases of repolymerized hydrolysates, the smeared bands from 10 kDa to top of the separating and stacking gels (FIG. 3B, lanes 6-8) indicated that they contained a heterogeneous mixture of crosslinked polymer with wide ranging molecular weights. As in the case of WPIH-TG polymers (FIG. 1B, lanes 6-8), this wide molecular size distribution might be the result of limited availability of glutamine and lysine residues in peptides of the hydrolysates. Caseins contain approximately equal amount of glutamine and lysine residues. However, depending on their distribution in the primary structure and the sites of cleavage by the proteases, it is likely that some of the peptides in the hydrolysate might not contain or contain only a limited number of glutamine residues, which would limit their participation in the polymerization reaction. The wide molecular size distribution of CN-TG polymers (FIG. 3B, lanes 6-8) might be a reflection of this phenomenon.

Immunoreactivity of Casein Hydrolysates and their TG-Polymers

Figure 3C:
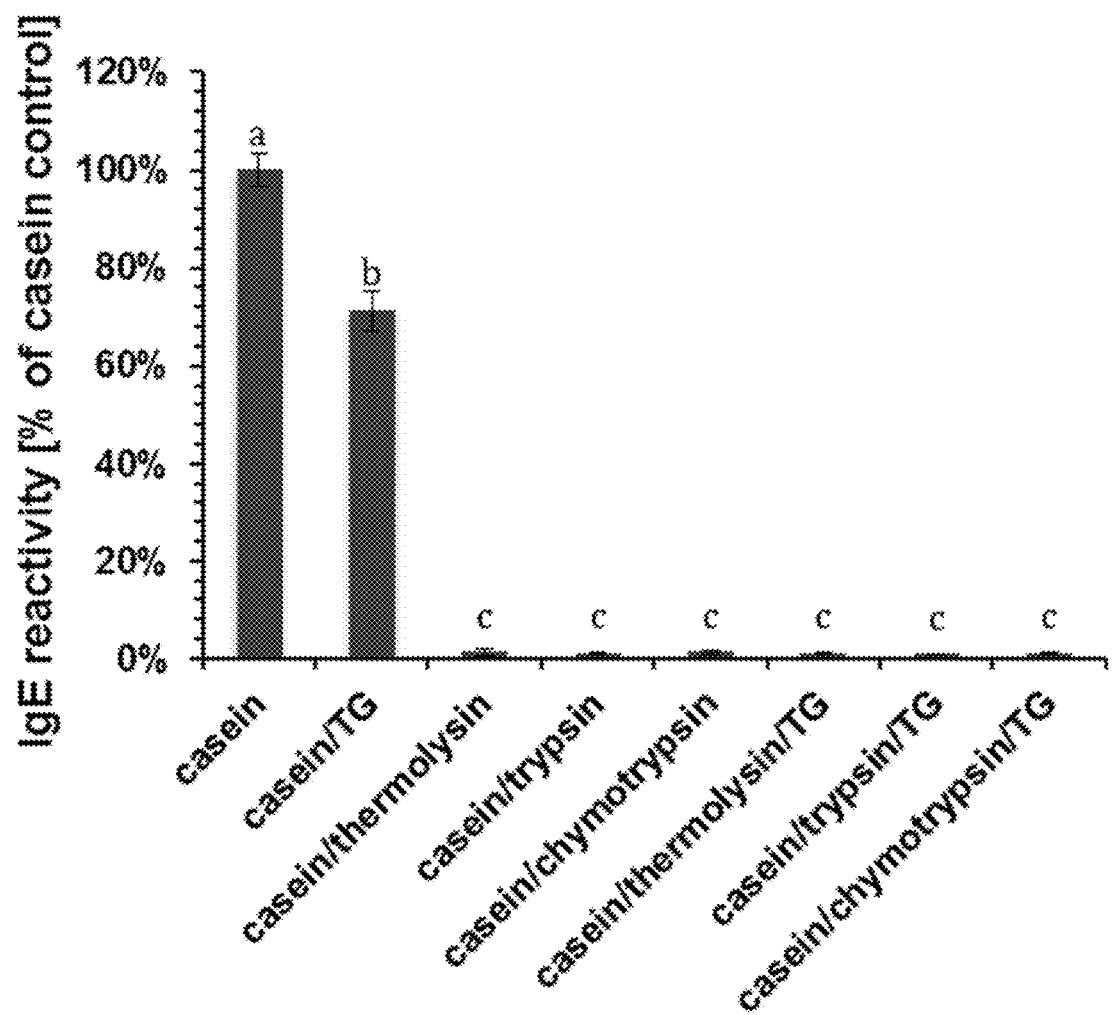
FIG. 3C. Immunoreactivity of enzyme-treated caseinate products. Statistical analysis was performed using Tukey HSD test. a-c: Mean values of columns with different letters imply that they are statistically significantly different (p>0.05).

Polymerization of intact casein (CN) using TGase decreased its immunoreactivity to about 70% of the control (FIG. 3C), indicating that a majority of antigenic epitopes (both conformational and linear epitopes) was still accessible to IgE binding in CN-TG polymers. On the other hand, the thermolysin, tryptic, and chymotryptic hydrolysates of CN showed no immunoreactivity. In addition, the TG-polymers of these CN hydrolysates (CNH-TG) also showed no immunoreactivity, indicating that almost all antigenic epitopes in casein were disrupted by hydrolysis; repolymerization of the peptides in the hydrolysate to large MW polymers did not result in reformation of any conformational epitopes.

Figure 4A:
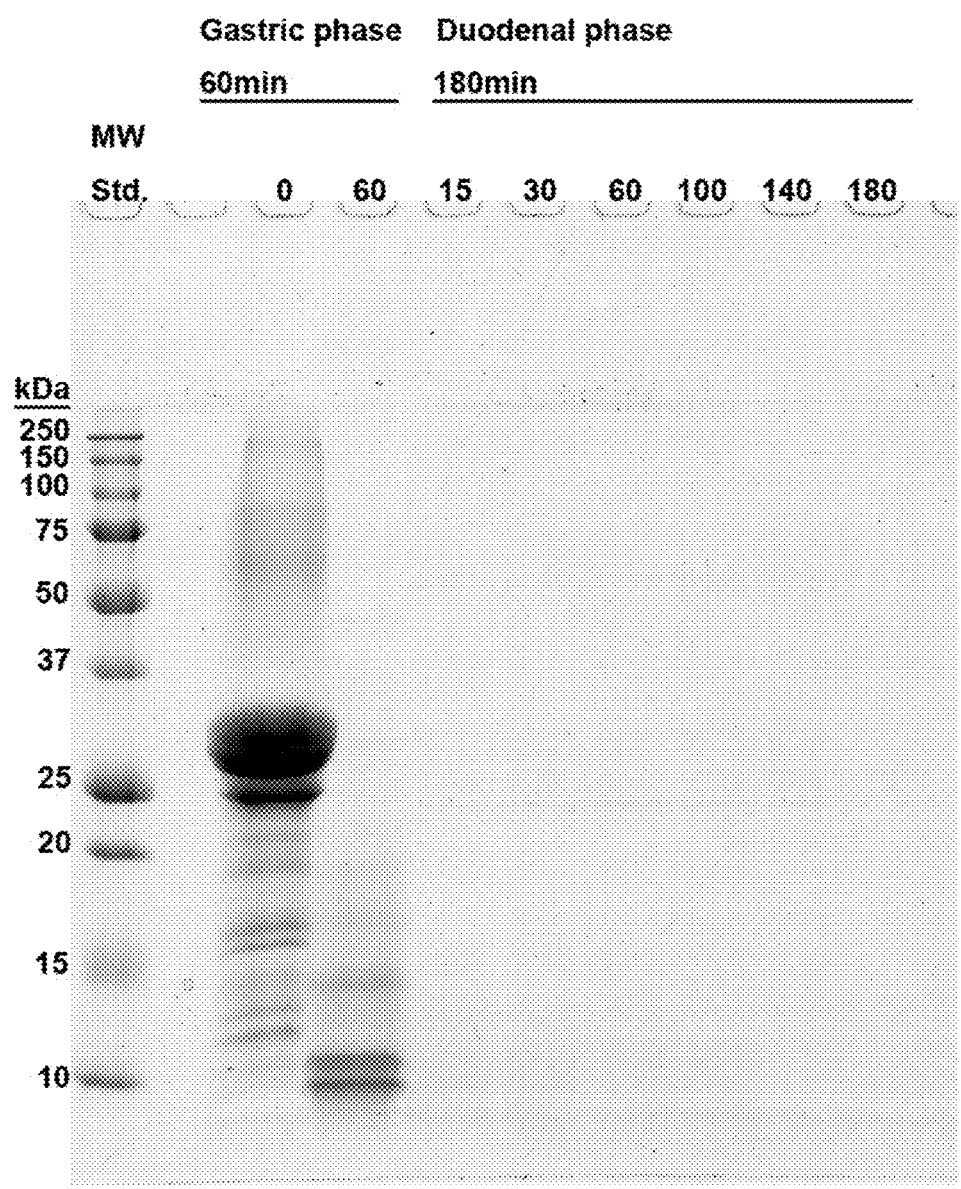
FIG. 4A. SDS-PAGE of peptides released from native casein during time course of in vitro digestion under simulated gastric and duodenal digestion conditions. The gastric digestion was performed for 60 min, followed by 180 min of duodenal phase digestion.
Figure 4B:
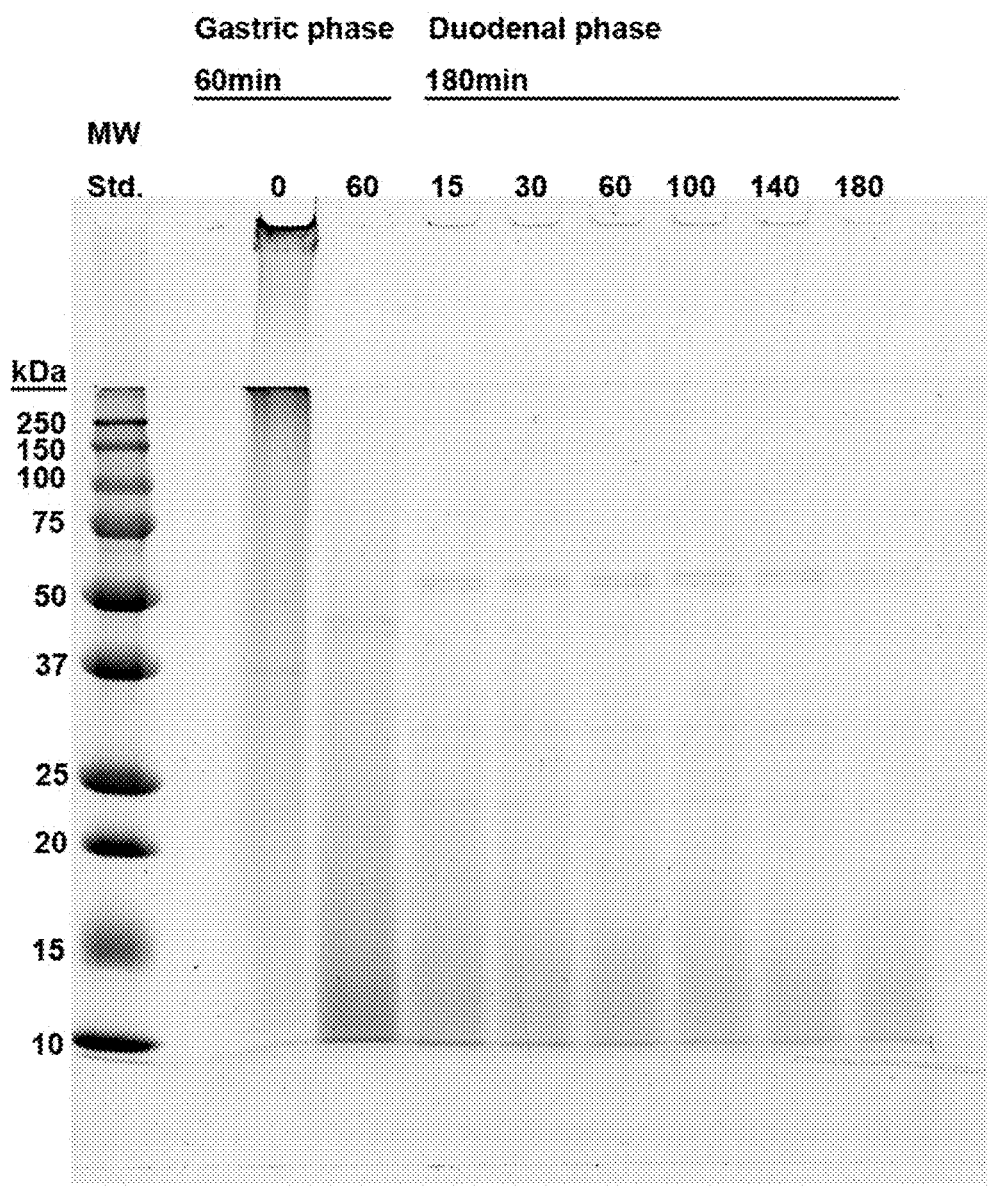
FIG. 4B. SDS-PAGE of peptides released from thermolysin-CNH-TG polymers during time course of in vitro digestion under simulated gastric and duodenal digestion conditions.

FIGS. 4A and 4B show the digestibility of native CN and thermolysin-CNH-TG polymers, respectively, in the two-step simulated gastric and duodenal phase digestion system. Native CN was readily digested to 10-15 kDa peptides during the gastric phase digestion and these peptides disappeared during the duodenal phase digestion. In the case of thermolysin-CNH-TG polymers, all the high MW polymers that could not enter the stacking and separating gels were digested completely to <60 kDa polypeptides during the 60 min gastric phase digestion. These polypeptides were further digested to <15 kDa peptides during the 180 min duodenal phase digestion. However, as in the case of WPI, these <15 kDa polypeptides appeared to be resistant to further break down to dipeptides and amino acids even after 180 min of duodenal phase digestion, indicating that these were the remnants of branched-chain polymers that no site-specific enzyme and endo- and exo-peptidases in pancreatin could digest. It is possible that a longer than 180 min incubation time with pancreatin could have further digested these limit polypeptides. However, since the gastro-intestinal transit time of food after intake is typically 3-4 h, it is unlikely that these limit polypeptides would be digested under normal in vivo conditions.

Figure 4C:
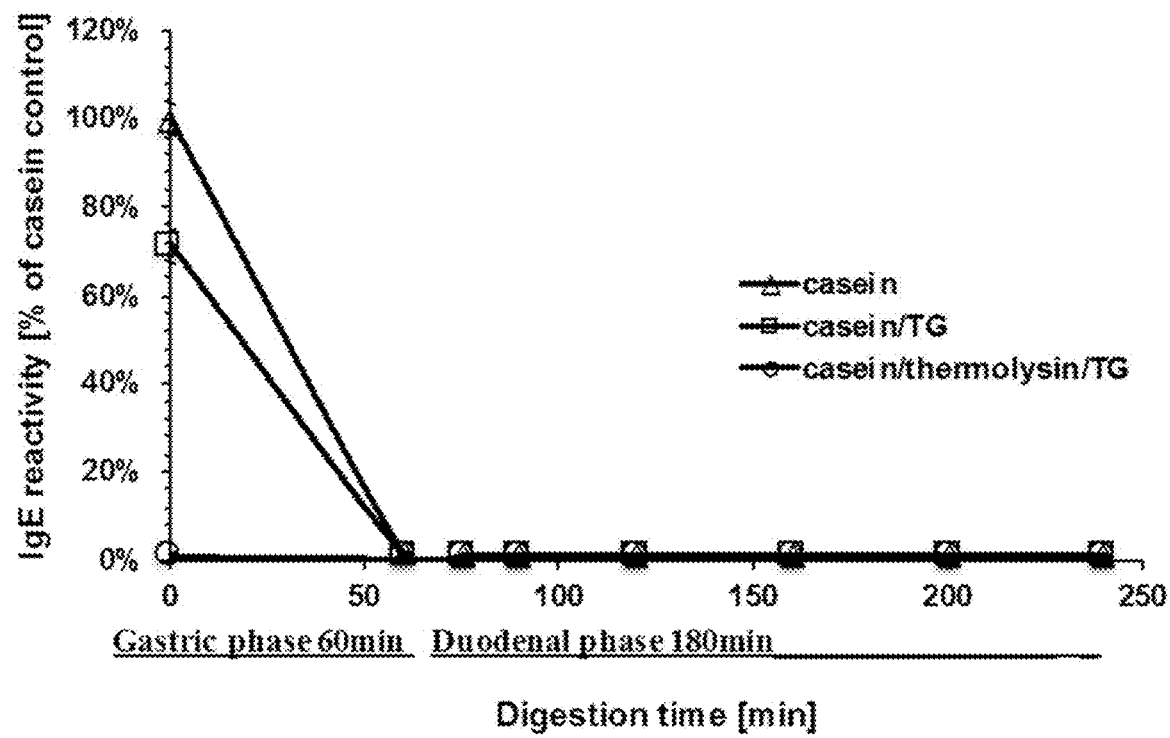
FIG. 4C. Immunoreactivity of peptides released during time course of simulated gastric and duodenal phase digestion of thermolysin-CNH-TG polymers.
Figure 5:
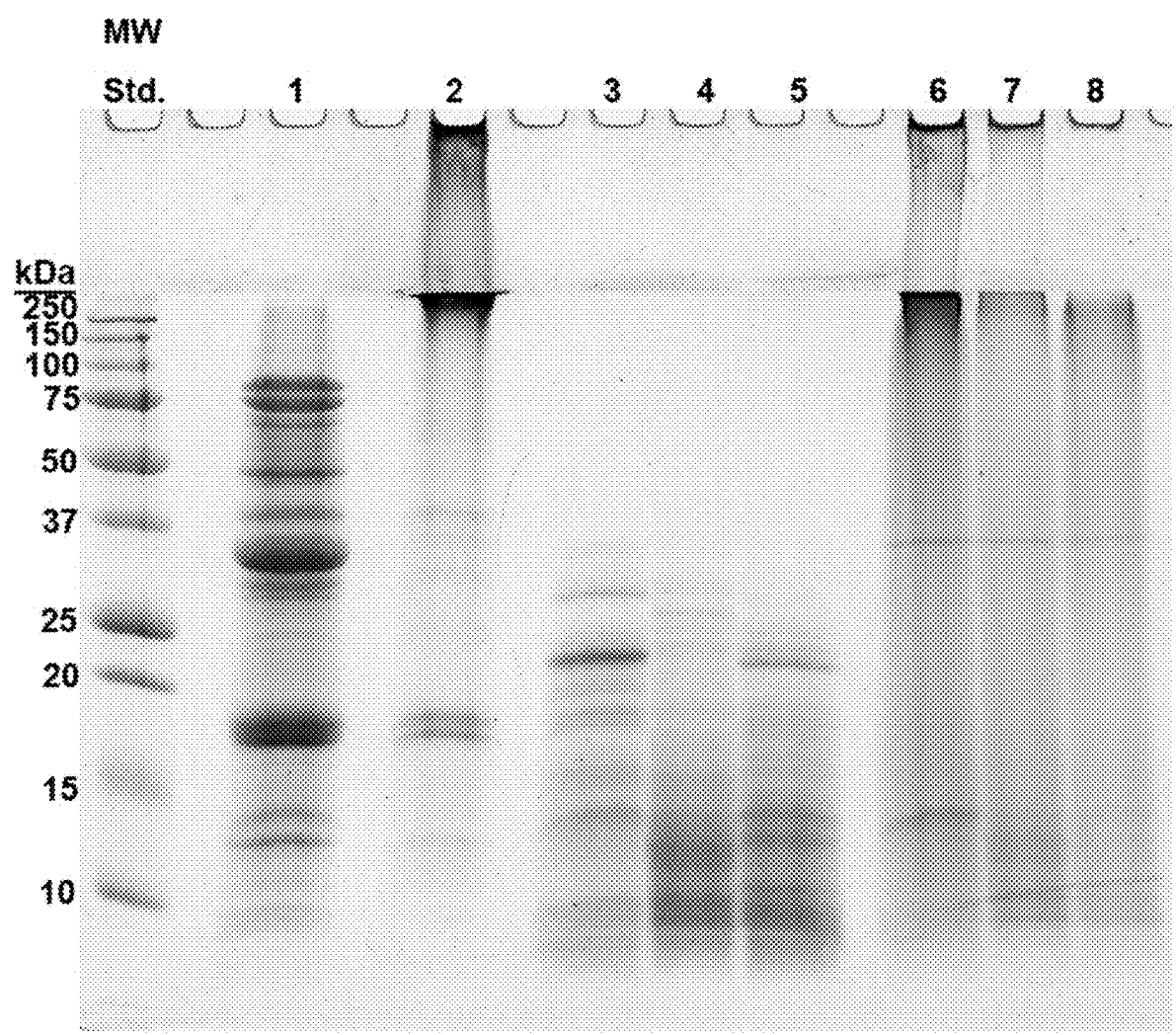
FIG. 5. SDS-PAGE of enzyme-treated soy protein products: Lane 1, soy protein isolate (SPI); Lane 2. SPI/TG; Lane 3, 10% SPI/thermolysin 200:1, 30 min; Lane 4, 5% denatured SPI/trypsin, 100:1, 30 min; Lane 5, 5% denatured SPI/chymotrypsin, 100:1, 30 min; Lane 6, 20% thermolysin hydrolysate/TG; Lane 7, 5% trypsin hydrolysate/TG; Lane 8, 5% chymotrypsin hydrolysate/TG.
Figure 6:
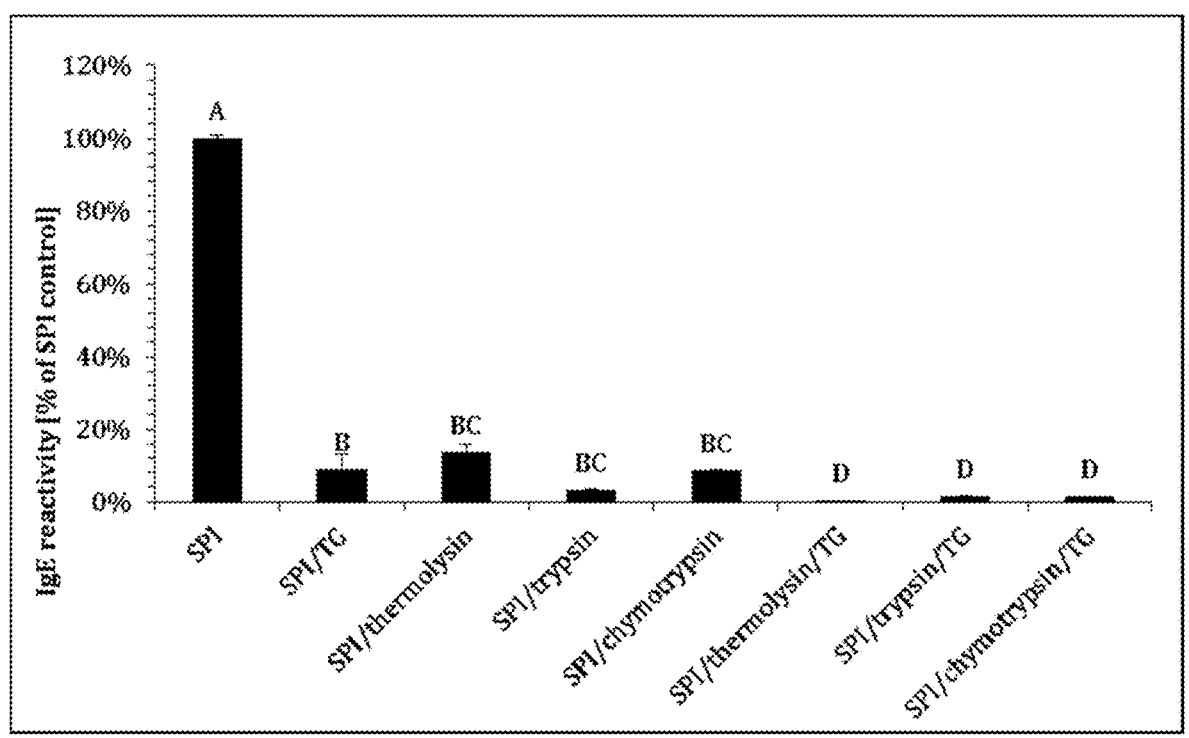
FIG. 6. Immunoreactivity of enzyme-treated soy protein products. Statistical analysis was performed using Tukey HSD. p<0.05 was considered statistically significant. Different letters on top of the columns depict statistical difference.
Figure 7:
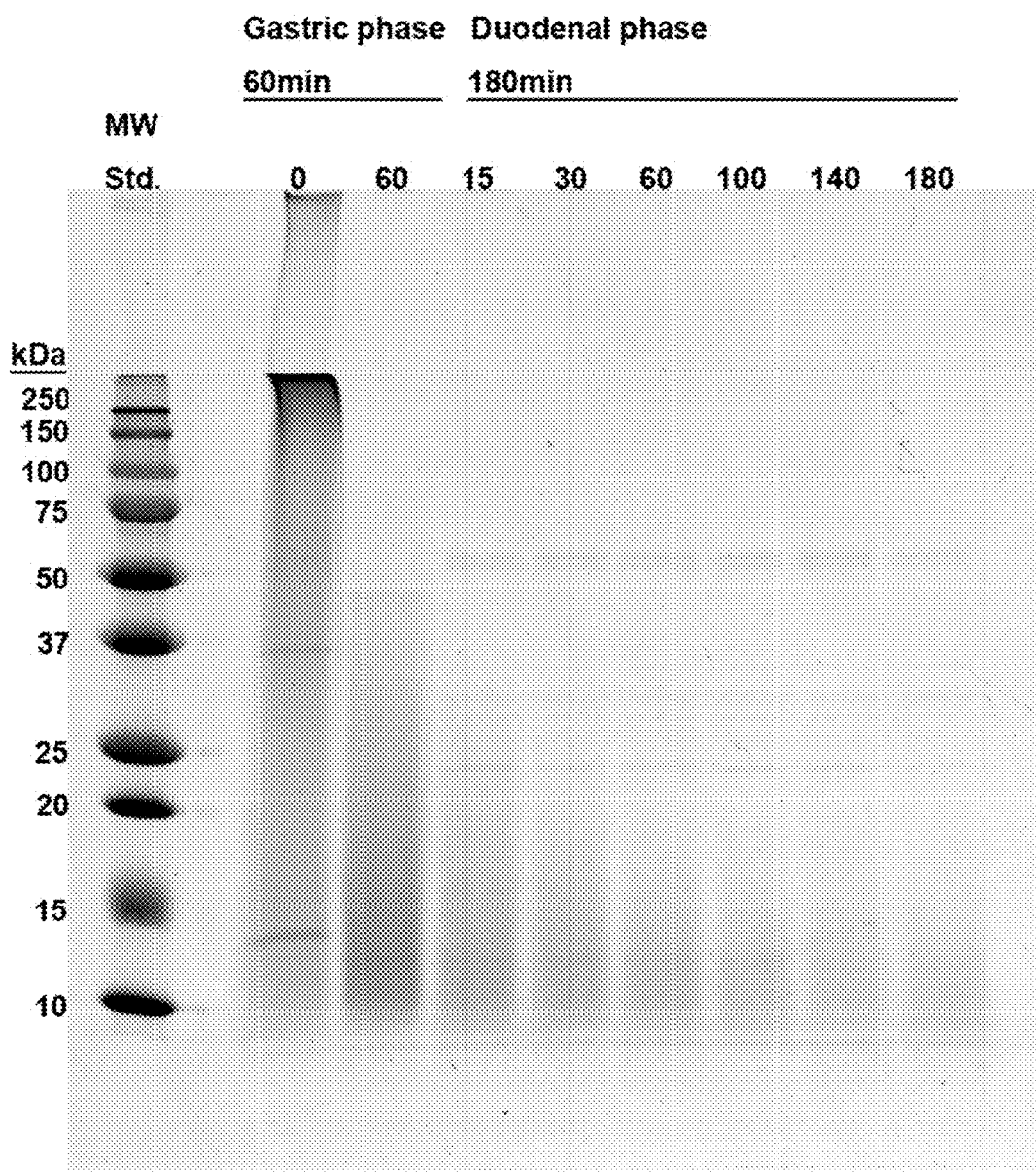
FIG. 7. SDS-PAGE of in vitro digested TG polymers of thermolysin hydrolysate of SPI.
Figure 8:
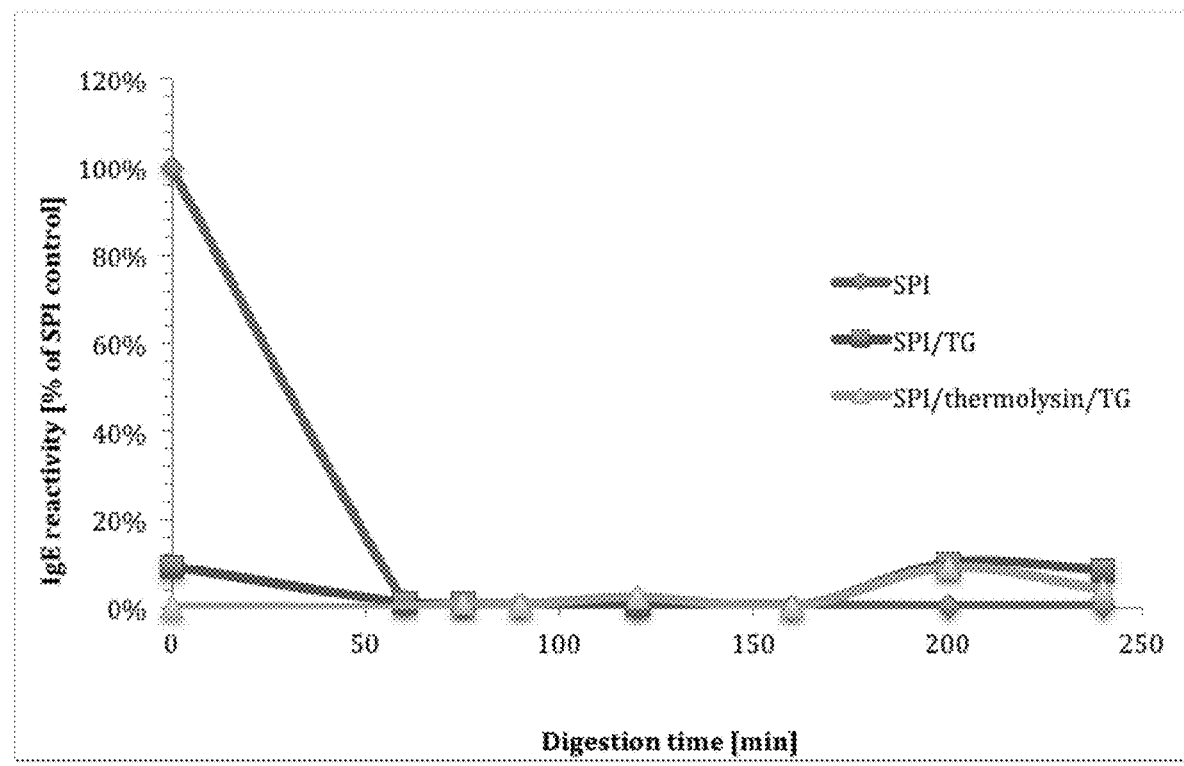
FIG. 8. IgE reactivity of in vitro digested TG polymers of thermolysin hydrolysate of SPI.

The immunoreactivity of peptides released during the time course of in vitro digestion of thermolysin-CNH-TG polymers is shown in FIG. 4C. The immunoreactivity of digested native casein and the thermolysin-CNH-TG polymers was almost zero throughout the 240 min digestion period, indicating that gastro-duodenal digestion of thermolysin-CNH-TG polymers did not release any antigenic peptides.

SPI Experiments

The experiments outlined above conducted on WPI and CN were conducted on SPI. The results of the experiments conducted on SPI were similar to those for the WPI and CN experiments (FIGS. 5-8).

Conclusion

Both caseins and whey proteins are known to be strongly allergenic (Baudon, Mougenot, & Didry, 1987; Docena et al., 1996). Casein hydrolysate has been found to be safe in infants allergic to cow's milk (Sampson, et al., 1991). However, partially hydrolyzed whey protein has been shown to trigger allergic symptoms in children with cow's milk allergy (Ragno et al., 1993). Those findings tentatively suggested that allergenicity of hydrolyzed milk proteins essentially stemmed from partially hydrolyzed whey protein components. The results of the current study, which is based on ELISA, agree with results of those earlier in vivo studies.

The results of the present study also strongly indicate that the immunoreactivity of hydrolyzed milk proteins, viz., whey proteins and casein, can be significantly reduced and/or eliminated using a two-step enzymatic process, namely initial partial hydrolysis using thermolysin, trypsin, or chymotrypsin, followed by repolymerization of the hydrolysate using TGase. Among the proteases, thermolysin is the most effective in disrupting allergenic epitopes in whey proteins. Upon repolymerization, the immunoreactivity of thermolysin-WPIH-TG polymers was the lowest (~5% of the control WPI), whereas the immunoreactivity of tryptic-WPIH-TG and chymotryptic-WPIH-TG polymers were at unacceptable levels of 35% and 45%, respectively. Likewise, the thermolysin-CN-TG polymers also did not have any immunoreactivity. In addition, digestion of the repolymerized CN and WPI hydrolysates under simulated gastro-duodenal conditions did not release IgE reactive peptides during the 240 min time course of digestion. This two-step enzymatic modification method is predicted not only to produce hypoallergenic protein polymers, but also to help in alleviating undesirable sensory properties, e.g., bitter flavor, associated with protein hydrolysates.

Findings for SPI were similar to those found for CN and WPI.

References

Agyare, K. K., & Damodaran, S. (2010). pH-stability and thermal properties of microbial transglutaminase-treated whey protein isolate. *Journal of Agricultural and Food Chemistry*, 58, 1946-1953.

Ahn, K. M., Han, Y. S., Nam, S. Y., Park, H. Y., Shin, M. Y., & Lee, S. I. (2003). Prevalence of soy protein hypersensitivity in cow's milk protein-sensitive children in Korea. *Journal of Korean Medical Science*, 18, 473-478.

Baudon, J. J., Mougenot, J. F., & Didry, J. R. (1987). Lymphoblastic stimulation test with food proteins in digestive intolerance to cow's milk and in infant diarrheas. *Journal of Pediatric Gastroenterology and Nutrition*, 6, 244-251.

Bindels, J. G., & Boerma, J. A. (1994). Hydrolysed cow's milk formulae. *Pediatric Allergy and Immunology*, 5, 189-190.

Buchert, J., Selinheimo, E., Kruus, K., Mattinen, M. L., Lantto, R., Autio, K., & Rastall, R. (2008). Using cross-linking enzymes to improve textural and other properties of food. *Novel enzyme technology for food applications*, Rastall, R., Ed.; Woodhead Publishing, Cambridge, UK, 2007; pp. 101-139.

Burks, A. W., Casteel, H. B., Fiedorek, S. C., Williams, L. W., & Pumphrey, C. L. (1994). Prospective oral food challenge study of two soybean isolates in patients with possible milk or soy protein enterocolitis. *Pedatric Allergy and Immunology*, 5, 40-45.

Businco, L., Dreborg, S., Einarsson, R., Giampietro, P. G., Host, A., Keller, K. M., Strobel, S, Wahn, U., Bjorksten, B., & Kjellman, M. N. (1993). Hydrolysed cow's milk formulae. Allergenicity and use in treatment and prevention: An ESPACI position paper. *Pediatric Allergy and Immunology*, 4, 101-111.

DeJong, G. A. H., & Koppelman, S. J. (2002). Transglutaminase catalyzed reactions: impact on food applications. *Journal of Food Science and Technology*, 67, 2798-2806.

Docena, G. H., Fernandez, R., Chirdo, F. G., & Fossati, C. A. (1996). Identification of casein as the major allergenic and antigenic protein of cow's milk. *Allergy*, 51, 412-416.

Dupont, D., Mandalari, G., Molle, D., Jardin, J., Léonil, J., Faulks, R. M., Wickham, M. S. J., Mills, E. N. C., & Mackie, A. R. (2010). Comparative resistance of food proteins to adult and infant in vitro digestion models. *Molecular Nutrition and Food Research*, 54, 767-780.

Exl, B. M., Fritsché, R. (2001). Cow's milk protein allergy and possible means for its prevention. *Nutrition*, 17, 642-651.

Fu, T. J., Abbott, U. R., & Hatzos, C. (2002). Digestibility of food allergens and nonallergenic proteins in simulated gastric fluid and simulated intestinal fluid A comparative study. *Journal of Agricultural and Food Chemistry*, 50, 7154-7160.

Halken, S., Hansen, K. S., Jacobsen, H. P., Estmann, A., Faelling, A. E., Hansen, L. G., Kier, S. R., Lassen, K., Lintrup, M., Mortensen, S., Ibsen, K. K., Osterballe, O., & Host, A. (2000). Comparison of a partially hydrolyzed infant formula with two extensively hydrolyzed formulas for allergy prevention: A prospective, randomized study. *Pediatric Allergy and Immunology*, 11, 149-161.

Han, X-Q., & Damodaran, S. (1996). Thermodynamic compatibility of substrate proteins affects their crosslinking by transglutaminase. *Journal of Agricultural and Food Chemistry*, 44, 1211-1217.

Leszczyńska, J., Łącka, A., & Bryszewska, M. (2006). The use of transglutaminase in the reduction of immunoreactivity of wheat flour. *Food and Agriculture Immunology*, 17, 105-113.

Li, Y., & Damodaran, S. (2016) In vitro Digestibility and IgE Reactivity of Enzymatically Cross-linked Heterologous Protein Polymers. *Food Chemistry*, 221,1151-1157.

Malandain H. (2005). Transglutaminases: a meeting point for wheat allergy, celiac disease, and food safety. *European Annals of Allergy and Clinical Immunology*, 37, 397-403.

Matoba, T., Hata, H. (1972). Relationship between bitterness of peptides and their chemical structures. *Agricultural Biological Chemistry*, 36, 1423-31.

Miller, K., Meredith, C., Selo, I., & Wal, J. M. (1999). Allergy to bovine β-lactoglobulin: specificity of immunoglobulin E generated in the Brown Norway rat to tryptic and synthetic peptides. *Clinical and Experimental Allergy*, 29, 1696-1704.

Ney, K. H. (1971). Prediction of bitterness of peptides from their amino acid composition. *Z Lebensm Unters Forsch*, 147:64-8.

Oldaeus, G., Anjou, K., Bjorksten, B., Moran, J. R., & Kjellman, N. I. M. (1997). Extensively and partially hydrolysed infant formulas for allergy prophylaxis. *Archives of Disease in Childhood*, 77, 4-10.

Olivier, C. E., Villas-Boas, M. B., Netto, F. M., & Zollner, R. D. L. (2012). Allergenicity of Bos d 5 in children with cow's milk allergy is reduced by transglutaminase polymerization. *Pediatric Allergy, Immunology, and Pulmonology*, 25, 30-33.

O'Loughlin, I. B., Murray, B. A., Kelly, P. M., FitzGerald, R. J., Brodkorb, A. (2012). Enzymatic hydrolysis of heat-induced aggregates of whey protein isolate. *Journal of Agricultural and Food Chemistry*, 60, 4895-4904.

O'Sullivan, D., & FitzGerald, R. J. (2012). Physicochemical properties and residual antigenicity of transglutaminase cross-linked sodium caseinate hydrolysates. *International Dairy Journal*, 23, 18-23.

Pahud, J. J., Monti, J. C., & Jos, R. (1985). Allergenicity of whey-protein—its modification by tryptic invitro hydrolysis of the protein. *Journal of Pediatric and Gastroentrology Nutrition*, 4, 408-413.

Palosuo, K., Varjonen, E., Nurkkala, J., Kalkkinen, N., Harvima, R., Reunala, T., & Alenius, H. (2003). Transglutaminase-mediated cross-linking of a peptic fraction of omega-5 gliadin enhances IgE reactivity in wheat-dependent, exercise-induced anaphylaxis. *Journal of Allergy and Clinical Immunology*, 111, 1386-1392.

Pedersen, M. H., Hansen, T. K., Sten, E., Seguro, K., Ohtsuka, T., Morita, A., Poulsen, L. K. (2004). Evaluation of the potential allergenicity of the enzyme microbial transglutaminase using the 2001 FAO/WHO Decision Tree. *Molecular Nutrition and Food Research*, 48, 434-440.

Ragno, V., Giampietro, P. G., Bruno, G., Businco, L. (1993). Allergenicity of milk protein hydrolysate formulas in children with cow's milk allergy. *European Journal of Pediatrics*, 152, 760-762.

Reddy, I. M., Kella, K. D., Kinsella, J. E. (1988). Structural and conformation basis of the resistance of beta-lactoglobulin to peptic and chymotryptic digestion. *Journal of Agricultural and Food Chemistry*, 36, 737-741.

Rosendal, A., & Barkholt, V. (2000). Detection of potentially allergenic material in 12 hydrolyzed milk formulas. *Journal of Dairy Science*, 83, 2200-2210.

Sampson, H. A., Bemhisel-Broadbent, J., Yang, E. & Scanlon, S. M. (1991). Safety of casein hydrolysate formula in children with cow milk allergy. *Journal of Pediatrics*, 118, 520-525.

Schagger, H., & Von Jagow, G. (1987). Tricine-sodium dodecyl sulfate-polyacrylamide gel electrophoresis for the separation of proteins in the range from 1 to 100 kDa. *Analytical Biochemistry*, 166, 368-379.

Stanic, D., Monogioudi, E., Dilek, E., Radosavljevic, J., Atanaskovic-Markovic, M., Vuckovic, O., Raija, L., Mattinen, M., Buchert, J., & Velickovic, T. C. (2010). Digestibility and allergenicity assessment of enzymatically crosslinked β-casein. *Molecular Nutrition and Food Research*, 54, 1273-1284.

Wróblewska, B., Karamać, M., Amarowicz, R., Szymkiewicz, A., Troszyńska, A., & Kubicka, E. (2004). Immunoreactive properties of peptide fractions of cow whey milk proteins after enzymatic hydrolysis. *International Journal of Food Science and Technology*, 39, 839-850.

Zeiger R S, Sampson H A, Bock S A, Burks W, Jr, Harden K, Noone S, Martin D, Leung S, Wilson G. (1999). Soy allergy in infants and children with IgE-associated cow's milk allergy. *Journal of Pediatrics*, 134, 614-622.

Example 2

Nanostructure and Functionality of Enzymatically Repolymerized Whey Protein Hydrolysate Summary Whey proteins (WPI) were polymerized with transglutaminase (TGase) before and after partially hydrolyzing the protein with thermolysin to produce protein nanoparticles/polymers. Electrophoresis and atomic force microscopy (AFM) were used to determine the size and structural characteristics of the polymers. The foaming and emulsifying properties of these nanoparticles were studied. The polymerized WPI (WPI-TG) produced more stable foams than the repolymerized WPI hydrolysate (WPIH-TG). In contrast, WPIH-TG produced better emulsions with better storage stability than WPI-TG emulsions. These differences were due to their structure and electrostatic properties: The WPI-TG particles were linear, less than 100 nm in size with lower net negative charge, whereas the WPIH-TG polymers were much larger and were highly negatively charged as judged from zeta potential. This suggested that while protein nanoparticles may provide Pickering stability to both emulsions and foams, strong lateral electrostatic repulsion between nanoparticles within the adsorbed film destabilizes foams but not emulsions.

Introduction

Dispersed systems, such as foams and emulsions, can be stabilized using soluble surfactants and by using hydrophilic nano- and micro-particles. While soluble surfactants, such as proteins and small molecule amphiphiles, stabilize dispersed systems by adsorbing to the air-water or oil-water interface and reducing the interfacial tension, nano- and micro-particles stabilize emulsions and foams through a phenomenon known as Pickering stabilization (Binks, 2002; Hunter, Pugh, Franks, & Jameson, 2008; Kalashnikova, Bizot, Cathala, & Capron, 2011). Studies have shown that chitin and cellulose nanocrystals, silica nanoparticles, hydrophobically modified starch particles, and spore particles were able to impart Pickering stabilization to oil-in-water emulsions (Tzoumaki, Moschakis, Kiosseoglou, & Biliaderis, 2011; Yusoff, & Murray, 2011; Kalashnikova, Bizot, Cathala, & Capron, 2011; Binks et al, 2011; Pichot, Spyropoulos, & Norton, 2009). This stabilizing effect of nanoparticles is simply related to binding of the particles to the oil droplet surface and forming a physical barrier against coalescence of the dispersed phase.

Soluble globular proteins are highly surface-active due to their amphiphilic nature, but they do not stabilize dispersed systems by the Pickering mechanism. Instead, they readily adsorb to fluid-fluid interfaces, reduce the interfacial tension, form a viscoelastic film at interfaces, and stabilize emulsions and foams against coalescence through a combination of electrostatic and steric repulsive forces (Damodaran, 2005). However, stable protein and protein-polysaccharide nanoparticles fabricated by using different methods (Dickinson, 2010; Turgeon, Smith, & Sanchez, 2007; Santipanichwong, Suphantharika, Weiss, & McClements, 2008)

might have the potential to impart Pickering stability, in addition to their surface activity and film forming ability, to foams and emulsions.

Protein nanoparticles are generally produced by thermal aggregation of proteins under controlled conditions (Lee et al, 2016; Matalanis, Jones, & McClements, 2011; Zhu and Damodaran, 1994). Such aggregates are formed via noncovalent interactions as well as via sulfhydryl-disulfide interchange interaction between denatured protein molecules. In these types of nano-aggregates, the charge characteristics of the primary protein molecules are not greatly altered as there is no net loss of amino and carboxyl groups. Protein nanoparticles or nano-structures also can be produced via enzymatic crosslinking of native and/or partially denatured proteins using enzymes such as transglutaminase (TGase) (Agyare & Damodaran, 2010). Since primary amino groups and glutamine residues are consumed in this crosslinking reaction, the protein nanoparticles produced by this method have greater negative charge density than the uncrosslinked protein molecule in the neutral pH range. Another appealing approach is to first enzymatically hydrolyze the protein and then enzymatically repolymerize the hydrolysate using TGase to produce a branched chain protein polymer/nanoparticle. Although peptide bond hydrolysis produces new α-amino and α-carboxyl groups, the positive charge on the α-amino group (pKa=7.8) is less than the negative charge on the α-carboxyl group (pKa=4.6) at pH 7.0. As a result, nanoparticles obtained with repolymerized protein hydrolysate would be more negatively charged than the nanoparticles obtained with polymerized intact protein. Even though the protein origin is same, the nanoparticles obtained by these two different routes might possess different functionality.

The major objective of the present study was to investigate the interfacial properties of enzymatically crosslinked whey protein nanoparticles. The hypothesis of this study was that polymerizing native and partially hydrolyzed whey proteins using TGase would produce highly negatively charged polydispersed nanoparticles. In addition to reducing interfacial tension, these nanoparticles could impart Pickering stabilization to foams and emulsions.

Materials and Methods
Materials

Whey protein isolate (WPI) was obtained from Davisco Foods International Inc., (Eden Prairie, Minn., USA). Thermolysin (Type X, 30-175 units/mg protein) was purchased from Sigma-Aldrich (St. Louis, Mo., USA). Microbial transglutaminase (TGase) used in this study (Activa-TI, 99% maltodextrin and 1% TGase, 100 units/g solid) was from Ajinomoto Food Ingredients (Eddyville, Iowa, USA). The enzyme was used without further purification.

Preparation of Branched-Chain WPI Polymers

To prepare crosslinked native WPI polymers, a 5% (w/w) WPI solution in deionized water containing 5 mM β-mercaptoethanol at pH 7.0 was treated with TGase at an enzyme to substrate ratio of 100 units/gram substrate. The polymerization reaction was carried out for 4 h at 37° C. and terminated by heating in boiling water for 8 min. The sample was then dialyzed using 6-8 kDa molecular weight cutoff membrane against water at pH 7.0 for 24 h to remove maltodextrin, followed by centrifugation at 7100 g for 10 min to remove any insoluble polymers. The solution was then lyophilized and stored at –20° C.

To prepare protein nanoparticles from WPI hydrolysate, first a 5% (w/w) WPI solution in deionized water, adjusted to pH 7.0, was preheated to 70° C. in a water bath for 30 min. Thermolysin was then added at an enzyme-to-substrate ratio of 1:6000 (w/w), and hydrolysis was carried out at 70° C. for 1 min. Hydrolysis was terminated by incubating in a boiling water bath for 8 min. The sample was lyophilized and stored at –20° C. To repolymerize the hydrolysate, a 5% w/w solution of the hydrolysate in water at pH 7.0 containing 5 mM 3-mercaptoethanol was treated with 100 units of TGase/gram substrate and incubated at 37° C. for 4 h. Subsequent heating in boiling water for 8 min terminated the polymerization reaction. The solution was then dialyzed using 6-8 kDa molecular weight cutoff membranes against water at pH 7.0 for 24 h to remove maltodextrin, salts, and any low molecular weight peptides. The dialyzed sample was then centrifuged at 7100 g for 10 min to remove any insoluble polymers. The solution was lyophilized and stored at –20° C. Several batches of the polymers were produced under identical experimental conditions; these samples showed similar molecular mass profiles in SDS-PAGE electrophoresis.

Determination of Degree of Hydrolysis (DH)

The degree of hydrolysis (DH) of thermolysin-digested WPI was determined by the pH-Stat method (Adler-Nissen, 1986) using a Mettler Toledo DL50 Autotritrator (Mettler Toledo, Greifensee, Switzerland). DH was calculated using the following equation:

$$DH=[V_{NaOH} \times N_{NaOH}]/(\alpha \times m \times h_{tot})] \times 100\%$$

where α was the degree of dissociation of α-amino groups, m was the mass of protein (g), and $h_{tot}$ was the total number of peptide bonds in the protein (meq/g protein). The concentration of NaOH used was 0.05N. The α value depended on temperature and pH, which were maintained at 70° C. and 7.0, respectively. The corresponding α value and $h_{tot}$ for WPI were 0.6 and 8.8, respectively (Adler-Nissen, 1986). In these experiments, the hydrolysis conditions were chosen such that the DH of the hydrolysate was only about ~1%.

Electrophoresis

SDS-PAGE of protein samples under reducing and non-reducing conditions was performed as described previously (Agyare & Damodaran, 2010) using a 12.5% acrylamide separating and a 4.5% acrylamide stacking slab gel.

Apparatus for Measuring Foaming Properties

Evaluation of foaming capacity and foam stability was carried out in a Laplace pressure apparatus. The apparatus used for this purpose is described in detail elsewhere (Yu & Damodaran (1991a). The physical principle behind this method is the Laplace pressure: According to Laplace, the pressure inside a foam bubble is greater than the pressure outside and this difference is given by $$\Delta P=2\gamma/r \quad (1)$$

where γ is the surface tension and r is the radius of the bubble. On the basis of this, the equation of state of foam in a closed environment can be shown to be, $$3V\Delta P+2\gamma\Delta A=0 \quad (2)$$

where ΔP and ΔA are the change in pressure and interfacial area, respectively, and V is the volume of the apparatus. According to equation 2, any change in the interfacial area of the foam, i.e. as a result of breakage of foam with time, will cause a corresponding increase in the pressure inside the closed vessel. The total initial interfacial area ($A_0$) at time t=0 can be obtained from total change in pressure inside the closed vessel at infinite time when the entire foam has collapsed. Thus, at $t=t_\infty$, $$A_0=3V\Delta P_\infty/2\gamma \quad (3)$$

The interfacial area of the foam at any time t during foam decay ($A_t$) is given by $$A_t = 3V(\Delta P_\infty - P_t)/2\gamma. \quad (4)$$

Since foam decay is assumed to follow first order kinetics, and since two distinct macroscopic processes, viz., liquid drainage and disproportionation (Oswald ripening), are involved in foam decay, the kinetics of foam decay can be expressed as a biphasic first order process, $$A_t/A_0 = Q_g \exp(-k_g t) + Q_d \exp(-k_d t), \quad (5)$$

where $k_g$ and $k_d$ are first-order rate constants for the gravitational drainage and disproportionation processes, respectively (Yu & Damodaran, 1991a). While $A_o$ provides information on the ability of a protein to create foam, i.e. foamability, the kinetics of foam decay provides information on foam stability. The rate constants are determined from nonlinear curve fitting of the foam decay data to equation 5.

The foaming properties of native WPI and enzyme modified WPI were studied using the Laplace pressure apparatus exactly as described elsewhere (Yu & Damodaran, 1991a, b). Briefly, 20 mL of protein solution (5% w/w) in 20 mM phosphate buffer was preequilibrated in a water bath at 25° C. for one hour before being loaded into the fritted glass tube of the apparatus housed in an environmental incubator maintained at 25° C. Nitrogen gas was bubbled through the protein solution at a rate of 20 mL/min until the foam rose to a premarked point at the top of the foam column. Closing all valves then closed the system. An in-built pressure transducer in the apparatus monitored the time-dependent increase of pressure inside the foam column. The pressure was then converted to interfacial area of the foam using equation 4. The surface tension γ of the protein solution was determined using the Whilhelmy plate method (Xu & Damodaran, 1992).

Emulsion Preparation and Analysis

Emulsions were prepared with 1% (w/w) protein solution in 20 mM phosphate buffer (pH 7.0) and 20% (v/v) soybean oil for a total volume of 3.5 mL. Coarse emulsions were prepared by sonication using a Branson Sonifier 450 (BRANSON Ultrasonics Corp., CT, USA). The coarse emulsions were then homogenized in a high-pressure homogenizer (EmulsiFlex-B3, Avestin, Inc., Ottawa, Canada) at an operating hydraulic pressure of 152 MPa with three passes. Emulsions were stored at room temperature in the dark and the particle size distribution was determined over the course of one month.

Emulsion droplet size distributions were measured using a 90Plus/BI-MAS particle sizer (Brookhaven Instruments Corp., NY, USA). Emulsions were diluted 1500-fold using deionized water prior to the measurement. The rate of change of emulsion interfacial area, as calculated from Multimodal Size Distribution (MSD) charts for diameter-by-volume (d32) data, was used to determine emulsion stability during storage over one month. Zeta potential of emulsion droplets in deionized water and in 0.1 M NaCl was measured using the same instrument.

Surface Tension

Surface pressure of the protein solution was measured by the Wilhelmy plate method using an LB trough (KSV 2000, KSV Instruments Ltd., Finland) as described elsewhere (Xu & Damodaran, 1992). In a typical experiment, 100 mL of $10^{-4}$% (w/v) protein solution in 10 mM phosphate buffered saline solution (I=0.1M), pH 7.0, was poured into a Teflon trough. The surface was vacuum aspirated with a clean fine glass capillary to create a clean new aqueous surface. The surface pressure development was recorded over a 24 h period without stirring the bulk phase. Preliminary experiments indicated that a $10^{-4}$% (w/v) bulk concentration of WPI was sufficient to form a saturated monolayer at the air-water interface at equilibrium.

pH-Turbidity Measurement

The pH versus apparent solubility profiles of native and enzyme modified WPI samples were determined by measuring the turbidity of 0.1% protein dispersion in the pH range 2 to 10 (Liu, Elmer, Low, & Nickerson, 2010; Nath, Patrickios, & Hatton, 1995). The turbidity of the solutions was measured as absorbance at 500 nm using a UV-visible spectrophotometer (Shimadzu UV-P1601 PC, Shimadzu Corp., Kyoto, Japan).

Atomic Force Microscopy

Topographical images of native and polymerized WPI samples were obtained using a BioScope Catalyst atomic force microscope (Bruker Corporation, Santa Barbara, Calif.) operated in peak force tapping (PFT) mode. Protein solutions were diluted to 10 ppb in water at pH 7.0. Two μL of the solution was drop-deposited onto a freshly cleaved mica surface that had been fixed with 0.01% w/v poly-L-lysine solution and washed to remove any salts. The slides were air dried until no liquid was visible on the mica. The topographical image data were analyzed using NanoScope Analysis software (version 1.40, Bruker Corporation, Santa Barbara, Calif.).

Statistical Analysis

Analytical replicates were performed at least two times to report means and standard deviations where appropriate. Statistical analysis was conducted using JMP Statistical Discovery™ from SAS. P-values less than 0.05 were considered statistically significant.

Results and Discussion

The rationale for selecting thermolysin as opposed to other proteases for making WPI hydrolysate (WPIH) was that this enzyme hydrolyzes peptide bonds at the N-side of hydrophobic amino acid residues. This mode of cleavage is expected to disrupt the hydrophobic sequences/segments in the protein as well as release peptides with lysine and glutamine residues mostly in the inner parts of released peptides. The degree of hydrolysis (DH) was intentionally limited to ~1%, as extensive digestion of WPI would have produced considerable amount of short peptides with no Lys and/or Gln residues available for the TGase-catalyzed repolymerization reaction.

SDS-PAGE Analysis of Crosslinked Proteins

Figure 9A:
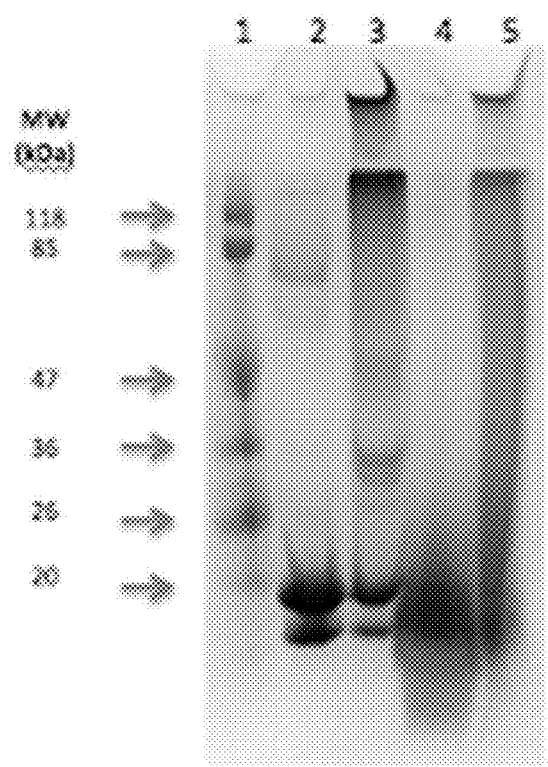
FIGS. 9A and 9B. SDS-PAGE of enzyme-modified WPI under reducing (FIG. 9A) and non-reducing (FIG. 9B) conditions.
Figure 9B:
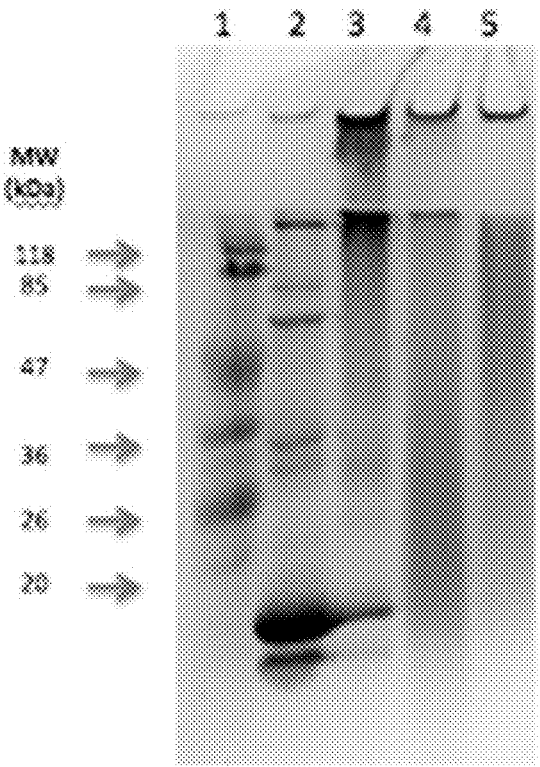

The SDS-PAGE profiles of untreated WPI, WPIH, TGase-treated WPI (WPI-TG), and TGase-treated WPIH (WPIH-TG) under reducing and non-reducing conditions are shown in FIGS. 9A and 9B. Bands of β-LG with molecular weight (MW) of 18.3 kDa and α-LA with MW of 14.4 kDa were visible in the control WPI (FIG. 9A, lane 2). The WPI-TG sample contained high MW polymers that were unable to penetrate the stacking and separating gels under reducing conditions (FIG. 9A, lane 3). It has been previously shown that α-LA was a better substrate for TGase than β-LG (Damodaran & Agyare, 2013), and therefore it is reasonable that a considerable amount of β-LG remained in the monomeric state after 4 h of polymerization (FIG. 9A, lane 3). The WPIH sample produced a smeared band with polypeptides below the size of β-LG (FIG. 9A, lane 4). As shown in FIG. 9A, lane 5, the WPIH-TG sample contained high MW polymers that were unable to penetrate the stacking and separating gels in addition to a broad size distribution of polymers in the separating gel. Since enzyme-treated WPI samples were subsequently heat treated to inactivate the enzymes, it is very likely that some of the polymers in these samples might be S-S crosslinked polymers in addition to TGase crosslinked polymers (Zhu & Damodaran, 1994). To assess this possibility, SDS-PAGE of these samples was run under non-reducing conditions and the results are shown in FIG. 9B. A comparison of lanes 3 in FIGS. 9A and 9B indicates that a majority of polymers in the WPI-TG sample were TGase crosslinked polymers. Comparison of lanes 4 and 5 in FIGS. 9A and 9B suggest that S-S crosslinked polymers were also present in the WPIH and WPIH-TG samples, as revealed from increased intensity of bands in the >20 kDa region in the non-reducing SDS-PAGE gel. Nevertheless, the amount of TGase crosslinked polymers that could not pass through the stacking and separating gels was high in both WPI-TG and WPIH-TG samples. Furthermore, since functionality tests on these samples were done under non-reducing conditions, the MW profiles shown in FIG. 9B, lanes 3-5 better represent the actual size distribution of these crosslinked protein polymers.

Atomic Force Microscopy

The topographical images of native and crosslinked WPI are shown in FIGS. 10A-10C2. Native WPI existed as tiny spherical particles (FIG. 10A), which were about 2-3 nm in diameter expected for β-LG and α-LA at pH 7.0. Few large aggregates were also seen, but those might be disulfide crosslinked and/or hydrophobically aggregated particles formed during isolation and spray drying of commercial WPI.

The WPI-TG sample contained a heterogeneous mixture of mostly linear strands of crosslinked WPI with about 4 nm in height and less than 100 nm in length (FIGS. 10B1 and 10B2). The overall shape of these particles in solution cannot be surmised from AFM images, as it is possible that protein nanoparticles may deform or flatten when dried for AFM (Saricay, Dhayal, Wierenga, & de Vries, 2012). A close-up view revealed distinct linear polymers both in individual and in aggregated states. On the other hand, the WPIH-TG particles were much larger than the WPI-TG particles, and they contained both spherical clusters as well as linear polymers with about 10 nm in height/diameter and the length ranging from 50 nm to more than 100 nm (FIGS. 10C1 and 10C2).

pH-Turbidity

Figure 11:
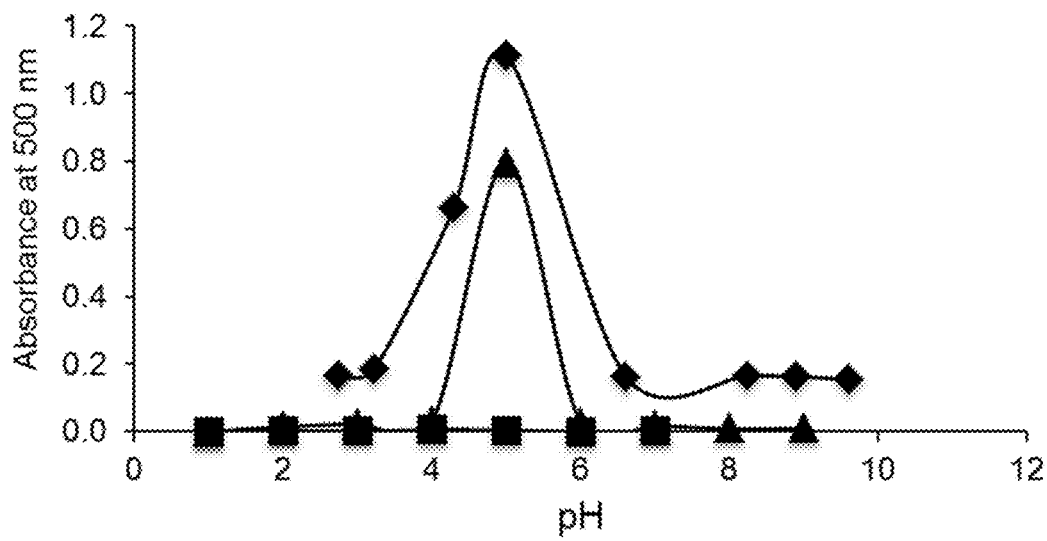
FIG. 11. pH-turbidity profile of native WPI (square, ■), WPI-TG (triangle, ▲), and WPIH-TG (diamond, ♦) samples in deionized water. The protein concentration was 0.1% (w/v).
Figure 12:
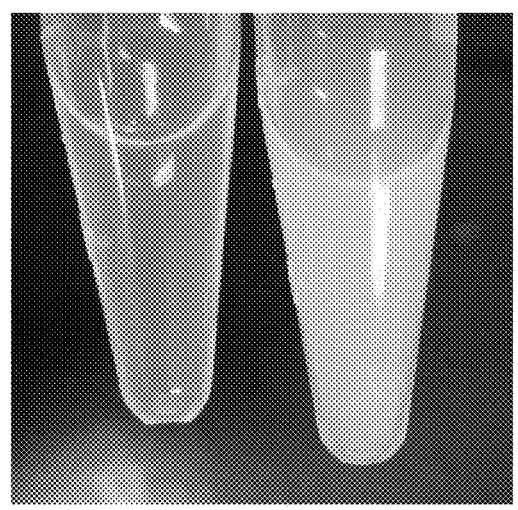
FIG. 12. Visual appearance of WPI-TG and WPIH-TG solutions (5% w/w) at pH 7.0 after centrifugation at 5000 g for 10 min.

The native WPI showed excellent solubility in the pH range 2.0-10.0 (FIG. 11). In contrast, both WPI-TG and WPIH-TG polymers exhibited typical pH-turbidity profiles with minimum solubility (or maximum turbidity) at about pH 5.0 to 5.3. This loss of solubility near the isoelectric point of whey proteins was likely the result of denaturation during the heating step to inactivate the protease. However, it has been previously reported that even in the absence of the heating step, incubation of β-LG with TGase caused alterations in the hydrophobic-to-hydrophilic balance of the protein surface due to crosslinking per se, which caused precipitation of β-LG at around pH 4.0 to 5.0 (Damodaran & Agyare, 2013). The WPIH-TG solution remained as a translucent colloidal solution at pH>7.0 even after centrifugation at 5000 g for 10 min (FIG. 12), which indicated that the large molecular weight WPIH-TG polymers were truly in a stable colloidal state. The WPI-TG solutions were also translucent, but more transparent than WPIH-TG in the pH range 3.0>pH>7.0. The slight turbidity seen in the WPI-TG solution at pH 7.0 might be due to ~100 nm size crosslinked polymers. The difference in the appearances of WPI-TG and WPIH-TG solutions essentially reflects differences in the size distribution of the crosslinked polymers in these samples (see FIGS. 10B1, 10B2, 10C1, and 10C2).

Foaming Properties

Preliminary experiments indicated that sufficient foam to fill the foam column (92 mL) of the Laplace pressure apparatus was not possible with a 1% (w/w) solution of native WPI. Thus, a 5% (w/w) protein concentration was used in all experiments. The kinetics of surface area decay of native WPI, WPI-TG, WPIH and WPIH-TG foams are presented in FIG. 13A. The decay of these foams generally followed nonlinear first order kinetics, which suggested apparent involvement of at least two kinetic phases as described by equation 5. These two processes represent gravitational drainage of liquid from the lamella and disproportionation of gas bubbles due to inter-bubble gas diffusion, which are fundamental processes in foam decay (Yu & Damodaran, 1991a). Therefore, regardless of biphasic or monophasic first order kinetics, it is reasonable to assume that both events occur during foam decay. Since inter-bubble gas diffusion would be significant only below a critical film thickness, the first kinetic phase can be attributed mostly to gravitational drainage (Yu & Damodaran, 1991a, b). The rate constants of drainage and disproportionation were calculated as described by Yu and Damodaran (1991, a, b). These values are given in Table 1.

TABLE 1

Foaming properties of native and various enzyme-modified WPI samples.

| Sample | $k_g$ (min$^{-1}$) | $k_d$ (min$^{-1}$) | Foaming time(s) | $A_0 \times 10^{-3}$ (cm$^2$) | Equilibrium surface pressure (mN/m)[1] |
|---|---|---|---|---|---|
| NativeWPI | 0.0075 ± 0.0007[B] | 0.0064 ± 0.0010[B] | 44.7 ± 5.0[A] | 19.7 ± 5.3[A] | 18.8 ± 0.3371[A] |
| WPI-TG | 0.0045 ± 0[B] | 0.0116 ± 0.0068[A] | 32 ± 0[B] | 19.5 ± 0.06[A] | 23.5 ± 0.3536[B] |
| WPI-H | 0.009 ± 0.0011[A] | 0.0249 ± 0.0025[A] | 28.3 ± 4.7[B] | 17.4 ± 0.4[A] | 16.4 ± 0.5132[C] |
| WPI-H-TG | 0.0101 ± 0.0014[A] | 0.0187 ± 0.0047[A] | 25.0 ± 3.0[B] | 18.1 ± 2.2[A] | 14.6 ± 0.7095[D] |

[A-D]Different letters denote statistical difference within each column.
[1]The equilibrium surface pressure of a $10^{-4}$% solution after 24 h.
$k_g$ and $k_d$ are gravitational drainage and disproportionation rate constants, respectively.
$A_0$ is the total initial surface area of the foam.

Native WPI followed a monophasic first order kinetics, suggesting that the macroscopic events of liquid drainage and disproportionation were happening simultaneously and the rate constants of each were equal in magnitude. In contrast, the foam of WPI-TG, which had crosslinked polymer particles in the size range of <100 nm (FIGS. 10B1 and 10B2), exhibited a convex-type biphasic first order decay. The WPI-TG foam was more stable than the native WPI foam for a period of 100 min and then collapsed thereafter, indicating that liquid drainage was the rate-limiting step in this foam. The gravitational drainage rate constant $k_g$ of WPI foam was almost twice that of WPI-TG foam (Table 1), indicating that the large linear polymer particles in WPI-TG (FIGS. 10B1 and 10B2) were responsible for retarding the gravitational drainage rate. The transformation from a linear (native WPI) to convex-type first order decay behavior (WPI-TG) reflects that the crosslinked protein nanoparticles impart a fundamental change to physical properties of the WPI-TG interfacial film. This might be related to the Pickering effect of large polymers/nanoparticles in addition to their inherent surface activity.

Figure 13A:
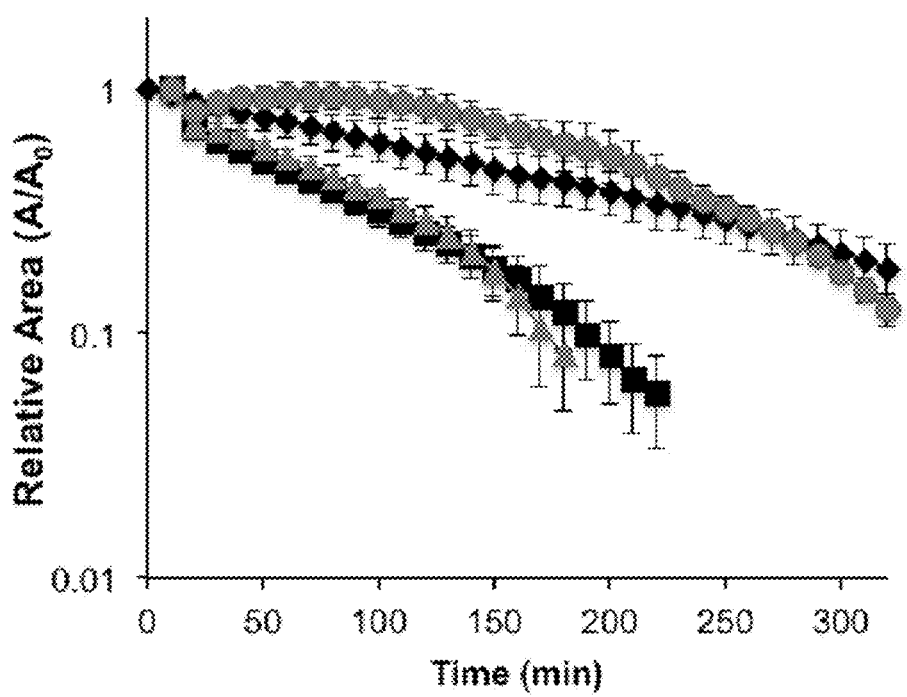
FIG. 13A. Interfacial area decay of foams of native WPI (diamond, ♦), WPI-TG (circle, ▲), WPIH (triangle, ▲), and WPIH-TG (square, ■) samples. The protein solutions (5% w/w) were made in 20 mM phosphate buffer, pH 7.0. The error bars represent standard deviation of replicates.

In contrast, in the case of WPIH and WPIH-TG foams while they also exhibited convex-type biphasic first order decay, they collapsed rapidly from the start (FIG. 13A). It should be noted that while the particle size of crosslinked polymers in WPI-TG was <100 nm, it was >100 nm in WPIH-TG polymers (FIGS. 10B1, 10B2, 10C1, and 10C2). Therefore, one would expect a greater Pickering effect in WPIH-TG-stabilized foam. One of the possible reasons for this dichotomy could be that, as discussed below (Emulsion stability section), the WPIH and WPIH-TG particles are more highly negatively charged than the WPI-TG polymers owing to newly created (as a result of partial hydrolysis of WPI) C-terminal carboxyl groups of the peptide fragments in these polymers. As a result, strong lateral electrostatic repulsive interactions between adsorbed WPIH-TG (and WPIH) particles within the interfacial film might rupture/destabilize the foam film, resulting in a faster rate of collapse. This charge-related destabilizing effect might be far more detrimental than any Pickering stabilization imparted by these particles. Thus, it appears that it is not just the size, but also the electrostatic properties of the particles also play a role in Pickering-stabilized foams.

The foaming time and initial interfacial area ($A_0$) of foams are presented in Table 1. Foamability is defined here as the initial total surface area $A_0$ of the foam, as calculated from $\Delta P_\infty$ using equation 3. In general, longer foaming time corresponded with larger interfacial area. Bubbling of native WPI solution produced the finest and most uniform distribution of bubbles, giving the appearance of denser foam with larger $A_0$. On the other hand, WPI-TG, WPIH, and WPIH-TG foams visually appeared to be polydispersed bubbles of varying sizes. The large bubbles visually observed in the WPIH and WPIH-TG foams also appeared more polyhedral in shape than the native WPI and WPI-TG foams. Even though native WPI and WPI-TG appeared to have produced higher initial interfacial areas, no statistically significant difference in $A_0$ was found between any of the samples despite qualitative differences (Table 1). Compared to native WPI, foaming times were shorter for WPI-TG, WPIH, and WPIH-TG samples. It should be noted that even though the stability of WPI-TG foam was better than native WPI (FIG. 13A), the foamability (i.e. $A_0$ value) of WPI was about the same as that of WPI-TG (Table 1). This suggests that the molecular properties that govern these two aspects of foam are quite different: While foamability does not greatly depend on the molecular size, high molecular weight polymers seem to possess the molecular characteristics needed for foam stability. However, among high molecular weight polymers, highly negatively charged polymers, e.g., WPIH and WPIH-TG polymers (see Emulsion stability section), appear to destabilize foams (FIG. 13A).

Figure 13B:
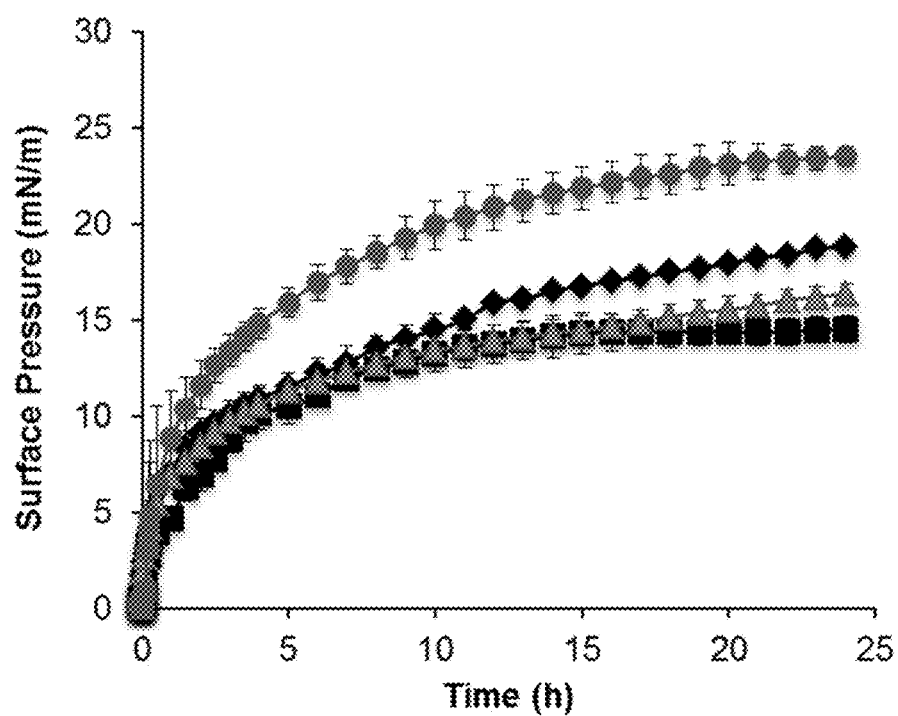
FIG. 13B. Kinetics of adsorption of native WPI (diamond, ♦), WPI-TG (circle, ▲), WPIH (triangle, ▲), and WPIH-TG (square, ■) at the air-water interface from a bulk phase (10 mM phosphate buffer, I=0.1M, pH 7.0) containing $10^{-4}$% (w/v) protein concentration.

Highly surface-active proteins produce smaller mean bubble size and thus large $A_0$ (Yu & Damodaran, 1991a, b; Zhu and Damodaran, 1994). The surface activities of native and enzyme-modified WPI were determined by studying the kinetics of adsorption at the air-water interface. FIG. 13B shows time-dependent increase of surface pressure at the air-water interface during adsorption of these proteins from a quiescent bulk solution containing 1.5 µg/mL protein concentration. The relative rates of surface pressure development as well as the final surface pressure after 24 h of adsorption followed the order WPI-TG>native WPI>WPIH>WPIH-TG. Surface pressure development was fastest for WPI-TG even though the size of polymers in this sample was larger than the native WPI (FIG. 13B), which should have decreased its rate of diffusion. This suggests that properties other than molecular mass, potentially its conformational rearrangement at the interface, might contribute its high surface activity. The relative order of surface activity of native WPI and enzyme-modified WPI samples correlated well with relative rates of foam decay, especially liquid drainage rates of these foams (Table 1).

The differences among the foaming properties of the treated WPI samples are inherently related to differences in their structural complexities, molecular/particle surface characteristics, and film-forming ability at the air/water interface (Damodaran, 2005). For instance, the better interfacial adsorption and foaming properties of WPI-TG might be related to its mostly linear crosslinked polymer structure observed in the AFM image (FIGS. 10B1 and 10B2). Such a structure might allow it to more effectively adsorb and reduce the interfacial tension than native WPI and WPIH-TG. On the other hand, the highly crosslinked state, the large particle size (FIGS. 10C1 and 10C2), and high negative charge of WPIH-TG particles (see Emulsion stability section) may restrict its adsorption and film-forming ability at the air-water interface.

Emulsion Stability

Figure 14:
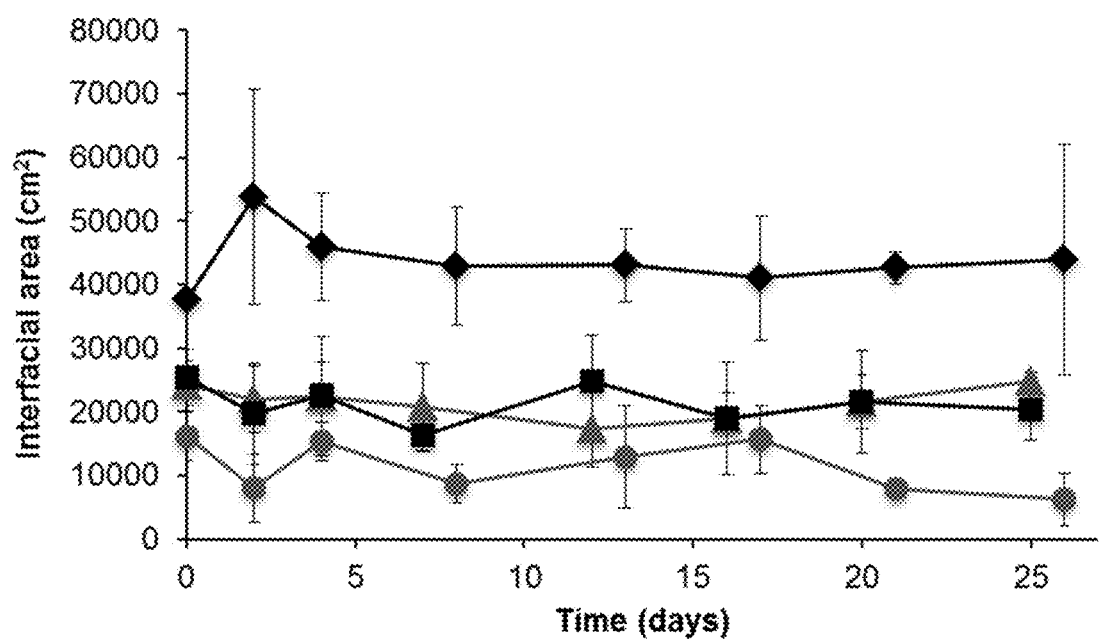
FIG. 14. Change in interfacial area of WPI (diamond, ♦), WPI-TG (circle, ●), WPIH (triangle, ▲), and WPIH-TG (square, ■) emulsions over one-month storage at room temperature. The emulsions were prepared using 1% (w/w) protein solution in 20 mM phosphate buffer, pH 7.0 and an oil volume fraction of 20% (v/v).
Figure 15A:
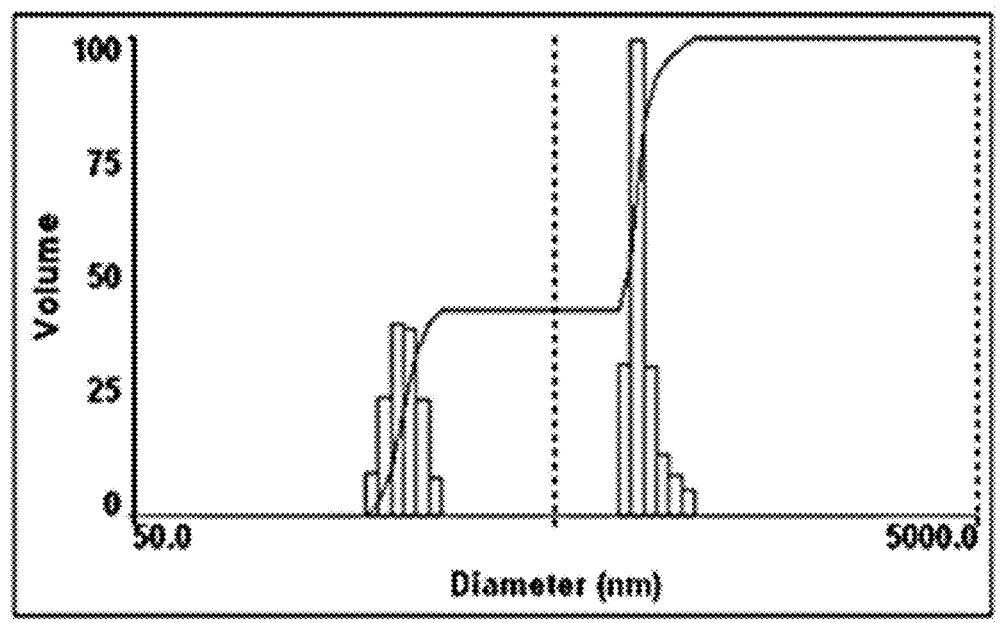
FIGS. 15A-15H. Multimodal size distribution charts displaying change in particle size distribution of emulsions of WPI (FIGS. 15A and 15B), WPI-TG (FIGS. 15C and 15D), WPIH (FIGS. 15E and 15F), and WPIH-TG (FIGS. 15G and 15H) on day 1 (FIGS. 15A, 15C, 15E, and 15G) and on day 27 (FIGS. 15B, 15D, 15F, and 15H).
Figure 15B:
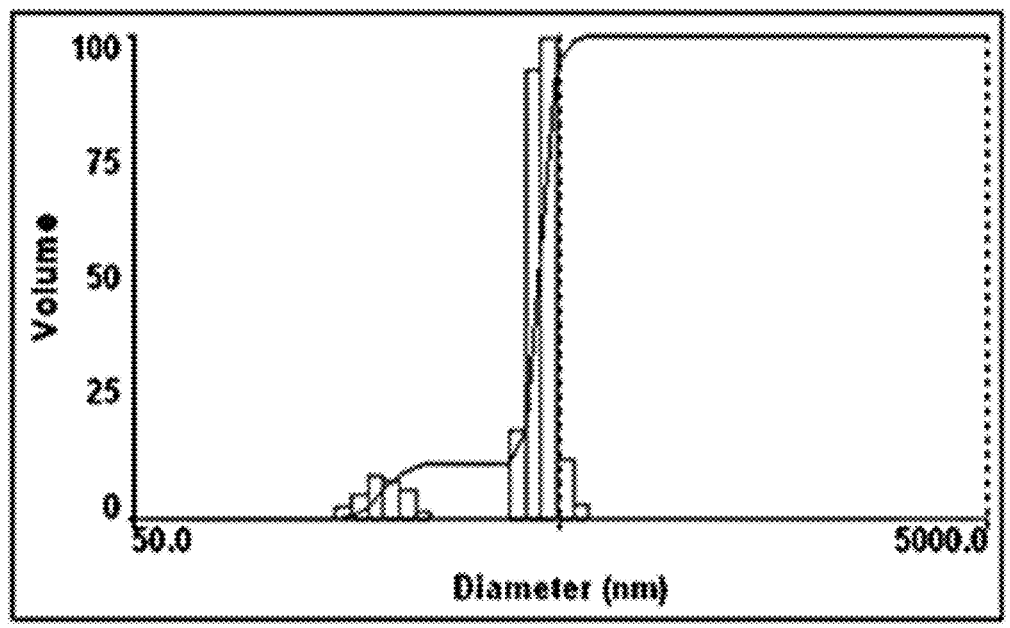
Figure 15C:
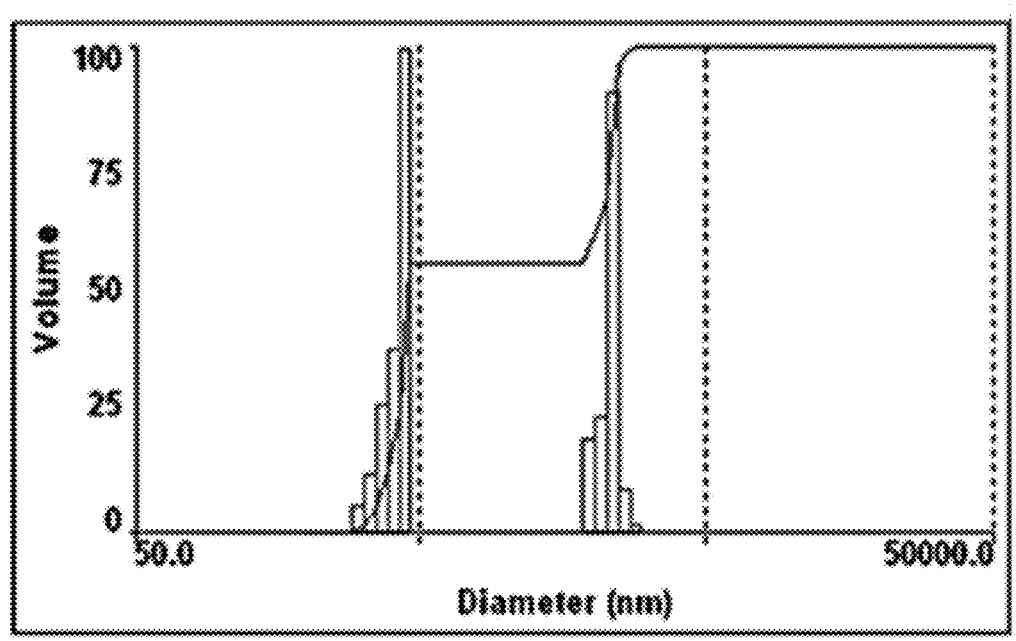
Figure 15D:
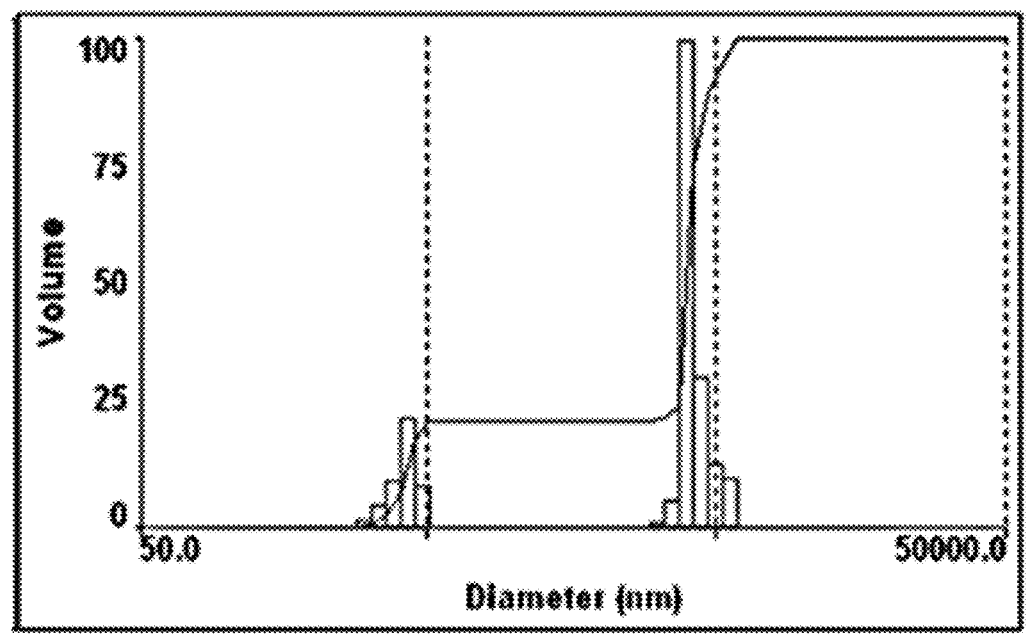
Figure 15E:
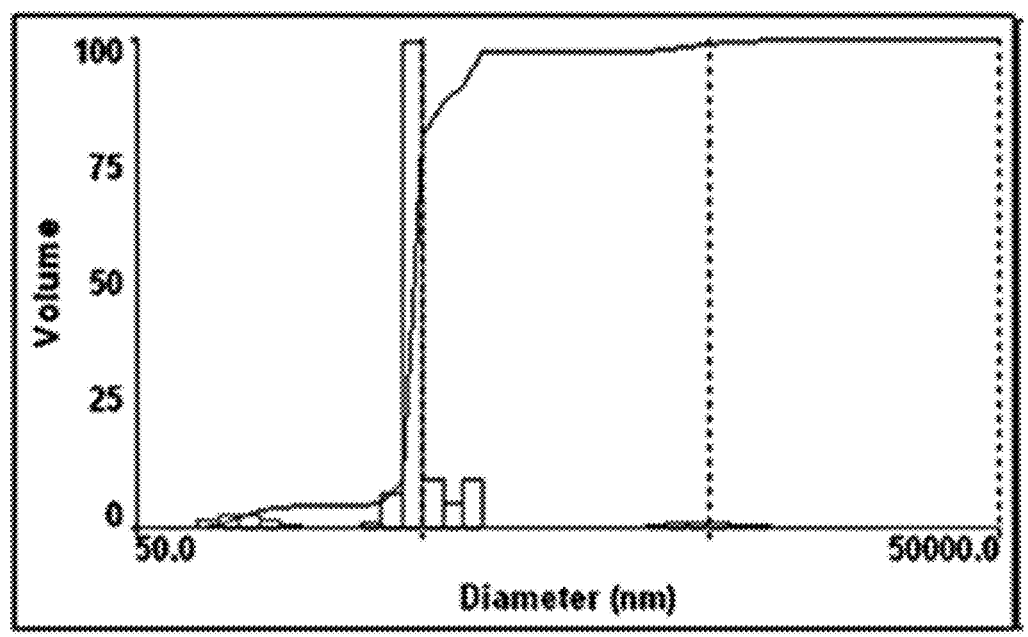
Figure 15F:
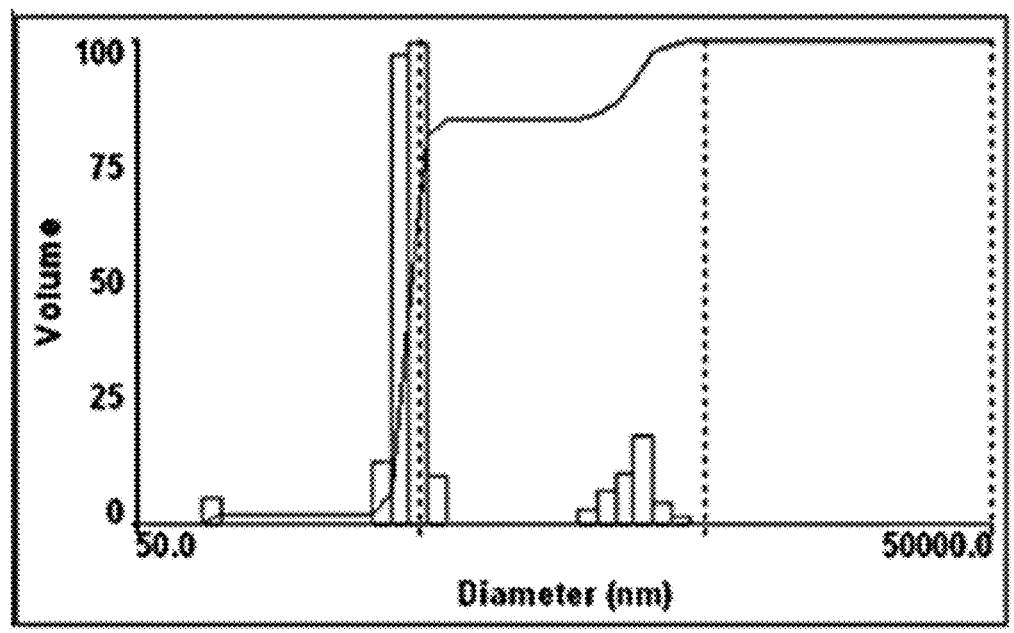
Figure 15G:
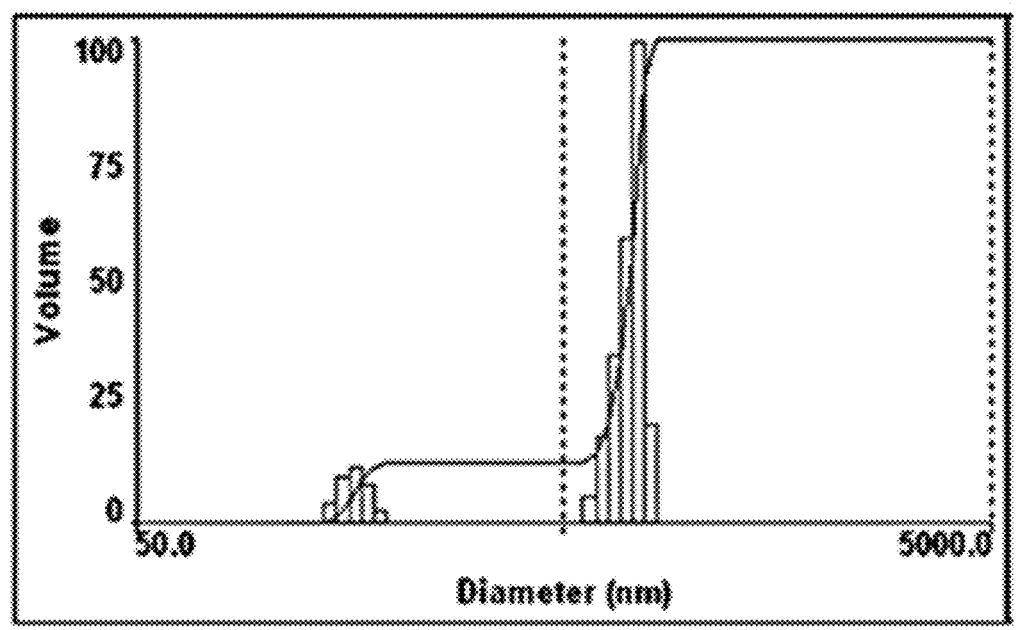
Figure 15H:
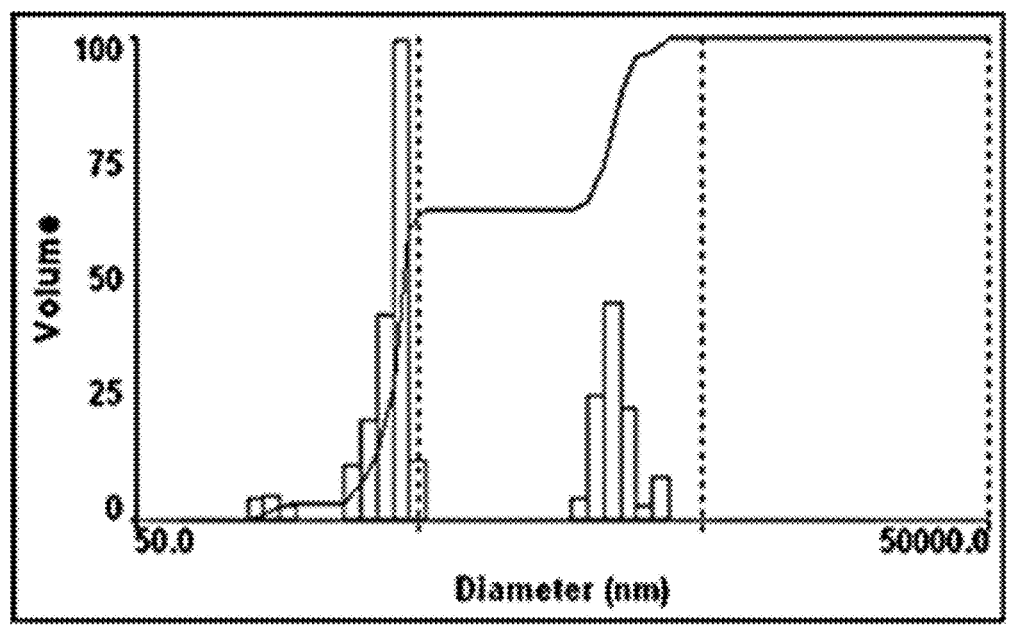

Native WPI produced the most stable emulsion with the highest interfacial area (FIG. 14). In contrast, WPI-TG exhibited poor emulsifying ability as judged from much lower emulsion interfacial area. It seems that native WPI most efficiently adsorbed to the oil-water interface and created the smallest droplet size distribution, whereas WPI-TG created the largest droplet size distribution, and the WPIH and WPIH-TG samples were intermediate with no significant difference between them. All these emulsions displayed bimodal and trimodal droplet size distributions immediately after formation as well as after 27 days of storage at room temperature (FIGS. 15A-15H). The larger droplet size distribution and lower interfacial area of emulsions made using enzyme-modified WPI might be due to their large polymer size, which might reduce the effective concentration of protein available for adsorbing to or coating of oil droplets during homogenization. In other words, unlike in native WPI-stabilized emulsion, only a small percentage of the protein mass of polymerized WPI might be physically at the oil-water interface and the rest might be suspended into the aqueous phase due their large size.

Visual appearances of these emulsions were different: Native WPI and WPIH emulsions appeared smooth and did not stick to the sides of the storage vial. Both WPI-TG and WPIH-TG emulsions appeared to have undergone aggregation/flocculation during high-pressure homogenization. With the exception of WPI-TG emulsion, regardless of their initial interfacial area, all other emulsions were essentially stable over a period of 27 days (FIG. 14). The interfacial area of the WPI-TG emulsion however decreased from 16000 $cm^2$/mL on day one to about 6200 $cm^2$/mL on day 27, which represented a 60% reduction of interfacial area. It is likely that the large colloidal-sized WPIH-TG polymers might impart Pickering stabilization of the emulsion. However, it is not clear why this Pickering stabilization was not very effective in the case of WPI-TG emulsions. It is likely that the magnitude of the Pickering effect might not be great enough to overcome potentially weak mechanical and electrostatic properties of the WPI-TG film.

Since the TGase-catalyzed crosslinking reaction consumes positively charged lysine residues and other primary amine groups, the TGase treated WPI samples would be more negatively charged than native WPI at pH 7.0. However, as shown in Table 2, the zeta potential of WPI stabilized emulsion was more negative than the WPI-TG stabilized emulsion. This suggests that the amount of WPI-TG adsorbed per unit area of the emulsion droplet was lesser than the amount of WPI adsorbed on the emulsion droplet. On the other hand, the zeta potential of emulsions stabilized by WPIH and WPIH-TG was more negative than the native WPI and WPI-TG stabilized emulsions in deionized water at pH 7.0 (Table 2), but the difference was very low in 0.1 M NaCl solution. This is quite reasonable because even though hydrolysis of a peptide bond releases one α-carboxyl and one α-amine group, the net charge on the α-amine group (pKa=7.8) at pH 7.0 would be less than the net charge on the carboxyl group (pKa=4.6). Furthermore, some of the newly released α-amino groups might have participated in the crosslinking reaction and therefore the overall charge of WPIH (which is in the S-S crosslinked state) and WPIH-TG polymers would be much higher than the native WPI and WPI-TG samples. After 27 days of storage, the negative zeta potential of all samples increased slightly with the exception of native WPI, which decreased (Table 2). This might be due to some compositional changes, i.e. the ratio of low molecular weight and high molecular wright polymers, in the interfacial film with time.

greater than 100 nm in size. The results of foaming and emulsification studies showed that while highly branched and highly negatively charged WPIH-TG polymers possessed reasonably good emulsifying properties, their foaming properties were poor. On the other hand, the WPI-TG polymers with comparatively lower negative charge density possessed excellent foaming properties, but poor emulsifying properties compared to native WPI and WPIH-TG. These results suggested that while protein nanoparticles impart Pickering stabilization to foam, high zeta potential of the particles destabilize foams. On the other hand, both high zeta potential and Pickering effect of highly branched polymers promote emulsion stability. The results demonstrated that highly stable and non-gelling emulsions could be made with WPIH-TG polymers; on the other hand, the foaming properties of WPI could be improved by polymerizing native WPI using TGase. Since TGase treated WPI hydrolysate exhibits no immunoreactivity (Damodaran and Li, 2017), emulsions and foams produced using WPIH-TG are predicted to be hypoallergenic.

References

Adler-Nissen, J. (1986). Enzymatic hydrolysis of food proteins. New York; Elsevier Applied Science Publishers.

Agyare, K. K., & Damodaran, S. (2010). pH-stability and thermal properties of microbial transglutaminase-treated whey protein isolate. *Journal of Agricultural and Food Chemistry*, 58, 1946-1953.

TABLE 2

Zeta Potential of emulsion droplets made with native WPI and enzyme-modified WPI samples at day 1 and after storage for 27 days at room temperature.

| Sample | Zeta potential (mV) in Deionized water pH 7 | | Zeta potential (mV) in Deionized water, pH 7, I = 0.1M | |
|---|---|---|---|---|
| | Day 1 | Day 27 | Day 1 | Day 27 |
| Native WPI | $-34.01 \pm 3.94^A$ | $-27.48 \pm 7.85^A$ | $-26.76 \pm 3.03^A$ | $-23.89 \pm 7.89^A$ |
| WPI-TG | $-32.98 \pm 1.08^A$ | $-36.7 \pm 9.52^A$ | $-19.92 \pm 1.72^B$ | $-25.72 \pm 1.23^A$ |
| WPIH | $49.96 \pm 6.74^B$ | $-59.86 \pm 3.51^C$ | $-28.19 \pm 1.94^A$ | $-30.45 \pm 1.73^B$ |
| WPIH-TG | $-58.4 \pm 5.18^{BC}$ | $-62.26 \pm 3.08^C$ | $-30.44 \pm 2.21^B$ | $-31.65 \pm 1.44^B$ |

$^{A\text{-}C}$Different letters denote statistical difference within each column.

After two-months of storage, the WPI and WPI-TG emulsions, which had much lower zeta potential than WPIH and WPIH-TG emulsions (Table 2), became a gel, indicating that protein-protein interactions between adsorbed protein films of emulsion particles in these emulsions created an extended network structure over a period of time. This inter-particle interaction might also involve sulfhydryl-disulfide interchange reaction between protein films of emulsion particles (Damodaran & Anand, 1997). In contrast, the WPIH and WPIH-TG emulsions, which had high zeta potential, remained fluid, indicating that the large highly negatively charged WPIH and WPIH-TG polymers/particles imparted strong electrostatic and steric repulsion (possibly via the Pickering mechanism) between emulsion droplets over long period of time and prevented formation of any three dimensional network structure between the droplets.

Conclusions

In the present study, nanoparticles of WPI were prepared by enzymatic (TGase) crosslinking of native protein, and also by repolymerizing partially hydrolyzed WPI using TGase. As judged from AFM images, the shape of WPI-TG particles was mostly linear and less than 100 nm in length, whereas WPIH-TG particles were mostly spherical and Binks, B. P. (2002). Particles as surfactants—similarities and differences. *Current Opinion in Colloid and Interface Science*, 7, 21-41.

Binks, B. P., Boa, A. N., Kibble, M. A., Mackenzie, G., & Rocher, A. (2011). Sporopollenin capsules at fluid interfaces: particle-stabilized emulsions and liquid marbles. *Soft Matter*, 7, 4017-4024.

Damodaran, S. (2005). Protein Stabilization of Emulsions and Foams. *Journal of Food Science*, 70, 54-65.

Damodaran, S., & Agyare, K. K. (2013). Effect of microbial transglutaminase treatment on thermal stability and pH-solubility of heat-shocked whey protein isolate. *Food Hydrocolloids*, 30, 12-18.

Damodaran, S., & Anand, K. (1997) Sulfhydryl-disulfide interchange-induced interparticle polymerization in whey protein-stabilized emulsions and its relation to emulsion stability. *Journal of Agricultural and Food Chemistry*, 45, 3813-3820.

Damodaran, S. and Li, Y. (2017) A Two-step Enzymatic Modification Method to Reduce IgE Reactivity of Milk Proteins. *Food Chemistry*, 237, 724-732.

Dickinson, E. (2010). Food emulsions and foams: stabilization by particles. *Current Opinion in Colloid and Interface Science*, 15, 40-49.

Hunter, T. N., Pugh, R. J., Franks, G. V. & Jemeson, G. J. (2008). The role of particles in stabilizing foams and emulsions. *Advances in Colloid and Interface Science*, 137, 57-81.

Kalashnikova, I., Bizot, H., Cathala, B., & Capron, I. (2011). New Pickering emulsions stabilized by bacterial cellulose nanocrystals. *Langmuir*, 27, 7471-7479.

Lee, H., Yildiz, G., dos Santos, L. C., Jiang, S., Andrade, J. E., Engeseth, N. J., & Feng, H. (2016). Soy protein nano-aggregates with improved functional properties prepared by sequential pH treatment and ultrasonication. *Food Hydrocolloids*, 55, 200-209.

Liu, S., Elmer, C., Low, N. H., & Nickerson, M. T. (2010) Effect of pH on the functional behavior of pea protein isolate-gum Arabic complexes. *Food Research International*, 43, 489-495.

Matalanis, A., Jones, O. G., & McClements, D. J. (2011). Structures biopolymer-based delivery systems for encapsulation, protection, and release of lipophilic compounds. *Food Hydrocolloids*, 25, 1865-1880.

Nath, S., Patrickios, C. S., & Hatton, T. A. (1995) Turbidimetric titration study of the interaction of proteins with acrylic polyampholytes. *Biotechnol Progress*, 11, 99-103

Pichot, R., Spyropoulos, F., & Norton, I. T. (2009). Mixed emulsifier stabilized emulsions: investigation of the effect of monoolein and hydrophilic silica particle mixtures on the stability against coalescence. *Journal of Colloid and Interface Science*, 329, 284-291.

Santipanichwong, R., Suphantharika, M., Weiss, J., & McClements, D. J. (2008) Core-shell biopolymer nanoparticles produced by electrostatic deposition of beet pectin onto heat-denatured β-lactoglobulin aggregates. *Journal of Food Science*, 73, N23-N30.

Saricay, Y., Dhayal, S. K., Wierenga, P. A., & de Vries, R. (2012). Protein cluster formation during enzymatic crosslinking of globular proteins. *Fraraday Discussions*, 158, 51-63.

Tatsumi, R., & Hattori, A. (1995). Detection of giant myofibrillar proteins connectin and nebulin by electrophoresis in 2% polyacrylamide slab gels strengthened with agarose. *Analytical Biochemistry*, 224, 28-31.

Turgeon, S. L., Schmitt, C., & Sanchez, C. (2007). Protein-polysaccharide complexes and conjugates. *Current Opinion in Colloid and Interface Science*, 12, 166-178.

Tzoumaki, M. V., Moschakis, T., Kiosseoglou, V., & Biliaderis, C. G. (2011). Oil-in-w2ater emulsions stabilized by chitin nanocrystal particles. *Food Hydrocolloids*, 25, 1521-1529.

Xu, S., & Damodaran, S. (1992) The Role of Chemical Potential in the Adsorption of Lysozyme at the Air-Water Interface. *Langmuir*, 8, 2021-2027.

Yu, M-A., & Damodaran, S. (1991a). Kinetics of protein foam destabilization: evaluation of a method using bovine serum albumin. *Journal of Agricultural and Food Chemistry*, 39, 1555-1562.

Yu, M-A., & Damodaran, S. (1991b). Kinetics of destabilization of soy protein foams. *Journal of Agricultural and Food Chemistry*, 39, 1563-1567.

Yusoff, A., & Murray, B. S. (2011). Modified starch granules as particle-stabilizers of oil-in-water emulsions. *Food Hydrocolloids*, 25, 42-55.

Zhu, H.; Damodaran, S. (1994). Heat-induced conformational changes in whey protein isolate and its relation to foaming properties. *Journal of Agricultural and Food Chemistry*, 42, 846-855.

Zhu, H. and Damodaran, S. (1994) Proteose peptones and physical factors affect foaming properties of whey protein isolate. *Journal of Food Science*, 59, 554-560.

EXEMPLARY EMBODIMENTS OF THE INVENTION

Embodiment 1. A method of processing protein comprising: hydrolyzing the protein with a proteolytic agent to generate hydrolyzed peptides; and, optionally, crosslinking the hydrolyzed peptides with a transglutaminase to generate crosslinked peptides.

Embodiment 2. The method of embodiment 1, comprising the crosslinking.

Embodiment 3. The method of any one of embodiments 1-2, wherein the proteolytic agent comprises a thermolysin.

Embodiment 4. The method of any one of embodiments 1-3, wherein the hydrolyzing comprises partially hydrolyzing the protein and wherein the hydrolyzed peptides are partially hydrolyzed peptides.

Embodiment 5. The method of embodiment 4, wherein the partially hydrolyzing comprises hydrolyzing the protein to a degree of hydrolysis of from about 0.1% to about 10%.

Embodiment 6. The method of any one of embodiments 4-5, wherein at least about 30% of total mass of the partially hydrolyzed peptides comprises peptides having a size of from about 3-10 kDa.

Embodiment 7. The method of any one of embodiments 1-6, wherein the protein comprises an allergenic protein.

Embodiment 8. The method of any one of embodiments 1-7, wherein the protein comprises at least one of milk protein, soy protein, peanut protein, and grain protein.

Embodiment 9. The method of any one of embodiments 1-8, wherein the protein comprises at least one of whey protein isolate and casein.

Embodiment 10. The method of any one of embodiments 1-9, wherein the protein comprises at least one of β-lactoglobulin and β-casein.

Embodiment 11. The method of any one of embodiments 1-10, wherein the protein comprises at least one of soy protein isolate and soy protein concentrate.

Embodiment 12. The method of any one of embodiments 1-11, wherein the protein comprises gluten.

Embodiment 13. The method of any one of embodiments 1-12, wherein the protein comprises an allergenic protein, and wherein the hydrolyzing is performed under conditions effective for the hydrolyzed peptides to have reduced allergenicity with respect to the protein.

Embodiment 14. The method of any one of embodiments 1-13, wherein the protein comprises an allergenic protein, and wherein the crosslinking is performed under conditions effective for the crosslinked peptides to have reduced allergenicity with respect to the hydrolyzed peptides.

Embodiment 15. The method of any one of embodiments 1-14, wherein the protein comprises an allergenic protein, and wherein the hydrolyzing and the crosslinking are performed under conditions effective for the crosslinked peptides to have reduced allergenicity with respect to the protein.

Embodiment 16. The method of any one of embodiments 13-15, wherein the reduced allergenicity comprises reduced IgE immunoreactivity.

Embodiment 17. The method of any one of embodiments 1-16, wherein the protein comprises whey protein, and wherein the hydrolyzing is performed under conditions effective for the hydrolyzed peptides to have IgE immunoreactivity less than 25% of IgE immunoreactivity of the protein.

Embodiment 18. The method of any one of embodiments 1-17, wherein the protein comprises whey protein, and wherein the crosslinking is performed under conditions effective for the crosslinked peptides to have IgE immunoreactivity less than 50% of IgE immunoreactivity of the hydrolyzed peptides.

Embodiment 19. The method of any one of embodiments 1-18, wherein the protein comprises whey protein, and wherein the hydrolyzing and the crosslinking are performed under conditions effective for the crosslinked peptides to have IgE immunoreactivity less than 10% of IgE immunoreactivity of the protein.

Embodiment 20. The method of any one of embodiments 1-19, further comprising generating an emulsion with the hydrolyzed peptides and/or the crosslinked peptides.

Embodiment 21. A product made by the method of any one of embodiments 1-20.

Embodiment 22. The product of embodiment 21, wherein the product comprises an emulsion.

Embodiment 23. The product of embodiment 21, wherein the product comprises a foam.

Embodiment 24. The product of any one of embodiments 21-23, wherein the product comprises a food product.

What is claimed is:

1. A method of processing a composition comprising protein, the method comprising:
   hydrolyzing at least some of the protein in the composition with a thermolysin to generate a hydrolysate comprising hydrolyzed peptides with a size of 3-10 kDa, wherein the protein in the composition comprises β-lactoglobulin; and
   crosslinking at least some of the hydrolyzed peptides in the hydrolysate with a transglutaminase to generate a crosslinked peptide composition comprising crosslinked peptides.

2. The method of claim 1, wherein the hydrolysate has a degree of hydrolysis of from 0.1% to 10%.

3. The method of claim 1, wherein at least 30% of total mass of peptides in the hydrolysate consists of peptides having a size of 3-10 kDa.

4. The method of claim 1, wherein the protein in the composition further comprises β-lactalbumin.

5. The method of claim 1, wherein the crosslinked peptide composition has reduced β-lactoglobulin-specific IgE immunoreactivity with respect to the composition.

6. The method of claim 1, wherein the crosslinked peptide composition has reduced β-lactoglobulin-specific IgE immunoreactivity with respect to the hydrolysate.

7. The method of claim 1, wherein the hydrolysate has β-lactoglobulin-specific IgE immunoreactivity less than 25% of β-lactoglobulin-specific IgE immunoreactivity of the composition.

8. The method of claim 1, wherein the crosslinked peptide composition has β-lactoglobulin-specific IgE immunoreactivity less than 50% of β-lactoglobulin-specific IgE immunoreactivity of the hydrolysate.

9. The method of claim 1, wherein the crosslinked peptide composition has β-lactoglobulin-specific IgE immunoreactivity less than 10% of β-lactoglobulin-specific IgE immunoreactivity of the composition.

10. The method of claim 9, wherein:
    the hydrolysate has β-lactoglobulin-specific IgE immunoreactivity less than 25% of β-lactoglobulin-specific IgE immunoreactivity of the composition; and
    the crosslinked peptide composition has β-lactoglobulin-specific IgE immunoreactivity less than 50% of β-lactoglobulin-specific IgE immunoreactivity of the hydrolysate.

11. The method of claim 1, wherein:
    the crosslinked peptide composition has reduced β-lactoglobulin-specific IgE immunoreactivity with respect to the hydrolysate; and
    the crosslinked peptide composition has β-lactoglobulin-specific IgE immunoreactivity less than 10% of β-lactoglobulin-specific IgE immunoreactivity of the composition.

12. The method of claim 11, wherein the composition is a composition isolated from whey.

13. A method of processing a composition comprising protein, the method comprising:
    hydrolyzing at least some of the protein in the composition with a thermolysin to generate a hydrolysate, wherein the protein in the composition comprises β-lactoglobulin; and
    crosslinking at least some of the hydrolyzed peptides in the hydrolysate with a transglutaminase to generate a crosslinked peptide composition comprising crosslinked peptides.

14. The method of claim 13, wherein:
    the crosslinked peptide composition has reduced β-lactoglobulin-specific IgE immunoreactivity with respect to the composition; and
    the crosslinked peptide composition has reduced β-lactoglobulin-specific IgE immunoreactivity with respect to the hydrolysate.

15. The method of claim 14, wherein the protein in the composition further comprises β-lactalbumin.

16. The method of claim 15, wherein:
    the crosslinked peptide composition has β-lactoglobulin-specific IgE immunoreactivity less than 10% of β-lactoglobulin-specific IgE immunoreactivity of the composition; and
    at least 30% of total mass of peptides in the hydrolysate consists of peptides having a size of 3-10 kDa.

17. The method of claim 16, wherein the hydrolysate has a degree of hydrolysis of from 0.1% to 10%.

18. The method of claim 15, wherein the composition is a composition isolated from whey.

19. The method of claim 18, wherein:
    the crosslinked peptide composition has β-lactoglobulin-specific IgE immunoreactivity less than 10% of β-lactoglobulin-specific IgE immunoreactivity of the composition; and
    at least 30% of total mass of peptides in the hydrolysate consists of peptides having a size of 3-10 kDa.

20. The method of claim 19, wherein the hydrolysate has a degree of hydrolysis of from 0.1% to 10%.

* * * * *

```
SEQUENCE LISTING

<160> NUMBER OF SEQ ID NOS: 4

<210> SEQ ID NO 1
<211> LENGTH: 20
<212> TYPE: PRT
<213> ORGANISM: Bos taurus

<400> SEQUENCE: 1

Ser Leu Ala Met Ala Ala Ser Asp Ile Ser Leu Leu Asp Ala Gln Ser
1               5                   10                  15

Ala Pro Leu Arg
            20

<210> SEQ ID NO 2
<211> LENGTH: 20
<212> TYPE: PRT
<213> ORGANISM: Bos taurus

<400> SEQUENCE: 2

Val Tyr Val Glu Glu Leu Lys Pro Thr Pro Glu Gly Asp Leu Glu Ile
1               5                   10                  15

Leu Leu Gln Lys
            20

<210> SEQ ID NO 3
<211> LENGTH: 10
<212> TYPE: PRT
<213> ORGANISM: Bos taurus

<400> SEQUENCE: 3

Met Glu Asn Ser Ala Glu Pro Glu Gln Ser
1               5                   10

<210> SEQ ID NO 4
<211> LENGTH: 15
<212> TYPE: PRT
<213> ORGANISM: Bos taurus

<400> SEQUENCE: 4

Arg Leu Ser Phe Asn Pro Thr Gln Leu Glu Glu Gln Cys His Ile
1               5                   10                  15
```